US011543416B2

(12) United States Patent
Lebert et al.

(10) Patent No.: US 11,543,416 B2
(45) Date of Patent: *Jan. 3, 2023

(54) METHOD FOR QUANTIFYING THERAPEUTIC ANTIBODIES

(71) Applicant: Promise Advanced Proteomics, Grenoble (FR)

(72) Inventors: Dorothée Lebert, Le Gua (FR); Guillaume Picard, Mont-Saxonnex (FR)

(73) Assignee: PROMISE PROTEOMICS, Grenoble (FR)

(*) Notice: Subject to any disclaimer, the term of this patent is extended or adjusted under 35 U.S.C. 154(b) by 655 days.

This patent is subject to a terminal disclaimer.

(21) Appl. No.: 15/773,195

(22) PCT Filed: Nov. 4, 2016

(86) PCT No.: PCT/EP2016/076740
§ 371 (c)(1),
(2) Date: May 3, 2018

(87) PCT Pub. No.: WO2017/077081
PCT Pub. Date: May 11, 2017

(65) Prior Publication Data
US 2019/0011455 A1 Jan. 10, 2019

(30) Foreign Application Priority Data
Nov. 6, 2015 (EP) .................... 15306767

(51) Int. Cl.
G01N 33/53 (2006.01)
G01N 33/68 (2006.01)
G01N 33/50 (2006.01)
C12N 9/64 (2006.01)

(52) U.S. Cl.
CPC ....... G01N 33/6857 (2013.01); C12N 9/6491 (2013.01); G01N 33/502 (2013.01); G01N 33/6848 (2013.01); C12Y 304/24003 (2013.01); C12Y 304/24023 (2013.01); C12Y 304/24024 (2013.01); C12Y 304/24035 (2013.01); G01N 2458/15 (2013.01)

(58) Field of Classification Search
None
See application file for complete search history.

(56) References Cited

FOREIGN PATENT DOCUMENTS

| WO | WO 2006/131013 | 12/2006 |
| WO | WO 2011/056590 | 5/2011 |

OTHER PUBLICATIONS

Hainsworth, J.D., et al. Rituximab with or without bevacizumab for the treatment of patients with relapsed follicular lymphoma. Clinical Lymphoma, Myeloma & Leukemia, 2014, 14(4):277-283.*
Bendtzen et al., *Enzyme Immunoassays and Radioimmunoassays for Quantification of Anti-TNF Biopharmaceuticals and Anti-Drug Antibodies*, Enzyme Immunoassays and Radioimmunoassays 83-101 (2011).
Duan et al., *Nano-scale Liquid Chromatography/Mass Spectrometry and On-the-fly Orthogonal Array Optimization for Quantification of Therapeutic Monoclonal Antibodies and the Application in Preclinical Analysis*, 1251 J. Chromatogr. A. 63-73 (Aug. 2012).
Dubois et al., *Immunopurification and Mass Spectrometric Quantification of the Active Form of a Chimeric Therapeutic Antibody in Human Serum*, 80 Anal. Chem. 1737-1745 1745 (2008).
Fernández Ocaña et al., *Clinical Pharmacokinetic Assessment of an Anti-MAdCAM Monoclonal Antibody Therapeutic by LC-MS/MS*, 84 Analytical Chemistry 5959-5967 (2012).
Heudi et al., *Towards Absolute Quantification of Therapeutic Monoclonal Antibody in Serum by LC-MS/MS Using Isotope-Labeled Antibody Standard and Protein Cleavage Isotope Dilution Mass Spectrometry*, 80(11) Anal. Chem. 4200-4207 (2008).
Kleinnijenhuis et al., *A generic sample preparation approach for LC-MS/MS bioanalysis of therapeutic monoclonal antibodies in serum applied to Infliximab*, 1(1) Journal of Applied Bioanalysis 26-34 (Jan. 2015).
Lebert et al., *Absolute and multiplex quantification of antibodies in serum using PSAQ™ standards and LC-MS/MS*, 7(10) Bioanalysis 1237-1251 (2015).
Lesur et al., *Accelerated tryptic digestion for the analysis of biopharmaceutical monoclonal antibodies in plasma by liquid chromatography with tandem mass spectrometric detection*, 1217 Journal of Chromatography A. 57-64 (2010).
Liu et al., *Quantitation of a recombinant monoclonal antibody in monkey serum by liquid chromatograph-mass spectrometry*, 414 Analytical Biochemistry 147-153 (2011).
Peng et al., *Development and Validation of LC-MS/MS Method for the Quantitation of Infliximab in Human Serum*, 78 Chromatographia 521-531 (2015).
Ungar et al., *Significance of low level infliximab in the absence of anti-infliximab antibodies*, 21(6) World J. Gastroenterol 1907-1914 (Feb. 14, 2015).
Vande Casteele et al., *Detection of infliximab levels and anti-infliximab antibodies: a comparison of three different assays*, 36 Aliment Pharmacol 765-771 (2012).
Wang et al., *Development and validation of a homogeneous mobility shift assay for the measurement of infliximab and antibodies-to-infliximab levels in patent serum*, 382 Journal of Immunological Methods 177-188 (2012).
Willrich et al., *Quantitation of infliximab using clonotypic peptides and selective reaction monitoring by LC-MS/MS*, 28 International Immunopharmacology 513-520 (2015).

(Continued)

Primary Examiner — Michael D Pak
(74) Attorney, Agent, or Firm — Buchanan Ingersoll & Rooney PC

(57) ABSTRACT

The present invention relates to a method for quantifying a therapeutic antibody in a sample of a human individual comprising a step of adding to a test sample which may contain therapeutic antibodies to be quantified a known amount of two or more labeled forms of said therapeutic antibodies.

17 Claims, 3 Drawing Sheets
Specification includes a Sequence Listing.

(56) References Cited

OTHER PUBLICATIONS

Xu et al., *A multiplexed hybrid LC-MS/MS pharmacokinetic assay to measure two co-administered monoclonal antibodies in a clinical study*, 6(13) Bioanalysis 1781-1794 (2014).

Zhang et al., *Generic Automated Method for Liquid Chromatography—Multiple Reaction Monitoring Mass Spectrometry Based Monoclonal Antibody Quantification for Preclinical Pharmacokinetic Studies*, 86 Anal. Chem. 8776-8784 (2014).

\* cited by examiner

SEQUENCE LISTING

<160> NUMBER OF SEQ ID NOS: 87

<210> SEQ ID NO 1
<211> LENGTH: 16
<212> TYPE: PRT
<213> ORGANISM: Artificial Sequence
<220> FEATURE:
<223> OTHER INFORMATION: Infliximab tryptic peptide

<400> SEQUENCE: 1

Leu Glu Glu Ser Gly Gly Gly Leu Val Gln Pro Gly Gly Ser Met Lys
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Infliximab tryptic peptide

<400> SEQUENCE: 2

Gly Leu Glu Trp Val Ala Glu Ile Arg
1               5

<210> SEQ ID NO 3
<211> LENGTH: 13
<212> TYPE: PRT
<213> ORGANISM: Artificial Sequence
<220> FEATURE:
<223> OTHER INFORMATION: Infliximab tryptic peptide

<400> SEQUENCE: 3

Ser Ile Asn Ser Ala Thr His Tyr Ala Glu Ser Val Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Infliximab trypric peptide

<400> SEQUENCE: 4

Ser Ala Val Tyr Leu Gln Met Thr Asp Leu Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Infliximab tryptic peptide

<400> SEQUENCE: 5

Thr Glu Asp Thr Gly Val Tyr Tyr Cys Ser Arg
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Infliximab tryptic peptide

<400> SEQUENCE: 6

Asp Ile Leu Leu Thr Gln Ser Pro Ala Ile Leu Ser Val Ser Pro Gly
1               5                   10                  15

Glu Arg

<210> SEQ ID NO 7
<211> LENGTH: 15
<212> TYPE: PRT
<213> ORGANISM: Artificial Sequence
<220> FEATURE:

<223> OTHER INFORMATION: Infliximab tryptic peptide

<400> SEQUENCE: 7

Ala Ser Gln Phe Val Gly Ser Ser Ile His Trp Tyr Gln Gln Arg
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Infliximab tryptic peptide

<400> SEQUENCE: 8

Tyr Ala Ser Glu Ser Met Ser Gly Ile Pro Ser Arg
1               5                   10

<210> SEQ ID NO 9
<211> LENGTH: 19
<212> TYPE: PRT
<213> ORGANISM: Artificial Sequence
<220> FEATURE:
<223> OTHER INFORMATION: Etanercept tryptic peptide

<400> SEQUENCE: 9

Leu Pro Ala Gln Val Ala Phe Thr Pro Tyr Ala Pro Glu Pro Gly Ser
1               5                   10                  15

Thr Cys Arg

<210> SEQ ID NO 10
<211> LENGTH: 13
<212> TYPE: PRT
<213> ORGANISM: Artificial Sequence
<220> FEATURE:
<223> OTHER INFORMATION: Etanercept tryptic peptide

<400> SEQUENCE: 10

Glu Tyr Tyr Asp Gln Thr Ala Gln Met Cys Cys Ser Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Etanercept tryptic peptide

<400> SEQUENCE: 11

Cys Ser Ser Asp Gln Val Glu Thr Gln Ala Cys Thr Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Etanercept tryptic peptide

<400> SEQUENCE: 12

Ile Cys Thr Cys Arg Pro Gly Trp Tyr Cys Ala Leu Ser Lys
1               5                   10

<210> SEQ ID NO 13
<211> LENGTH: 6
<212> TYPE: PRT
<213> ORGANISM: Artificial Sequence

```
<220> FEATURE:
<223> OTHER INFORMATION: Etanercept tryptic peptide

<400> SEQUENCE: 13

Leu Cys Ala Pro Leu Arg
1               5

<210> SEQ ID NO 14
<211> LENGTH: 16
<212> TYPE: PRT
<213> ORGANISM: Artificial Sequence
<220> FEATURE:
<223> OTHER INFORMATION: Etanercept tryptic peptide

<400> SEQUENCE: 14

Ser Met Ala Pro Gly Ala Val His Leu Pro Gln Pro Val Ser Thr Arg
1               5                   10                  15

<210> SEQ ID NO 15
<211> LENGTH: 37
<212> TYPE: PRT
<213> ORGANISM: Artificial Sequence
<220> FEATURE:
<223> OTHER INFORMATION: Etanercept tryptic peptide

<400> SEQUENCE: 15

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
                20                  25                  30

Gly Asp Glu Pro Lys
            35

<210> SEQ ID NO 16
<211> LENGTH: 24
<212> TYPE: PRT
<213> ORGANISM: Artificial Sequence
<220> FEATURE:
<223> OTHER INFORMATION: Adalimumab tryptic peptide

<400> SEQUENCE: 16

Gly Leu Glu Trp Val Ser Ala Ile Thr Trp Asn Ser Gly His Ile Asp
1               5                   10                  15

Tyr Ala Asp Ser Val Glu Gly Arg
                20

<210> SEQ ID NO 17
<211> LENGTH: 27
<212> TYPE: PRT
<213> ORGANISM: Artificial Sequence
<220> FEATURE:
<223> OTHER INFORMATION: Adalimumab tryptic peptide

<400> SEQUENCE: 17

Val Ser Tyr Leu Ser Thr Ala Ser Ser Leu Asp Tyr Trp Gly Gln Gly
1               5                   10                  15

Thr Leu Val Thr Val Ser Ser Ala Ser Thr Lys
                20                  25

<210> SEQ ID NO 18
<211> LENGTH: 29
<212> TYPE: PRT
<213> ORGANISM: Artificial Sequence
<220> FEATURE:
<223> OTHER INFORMATION: Adalimumab tryptic peptide
```

<400> SEQUENCE: 18

Gln Ala Pro Gly Lys Gly Leu Glu Trp Val Ser Ala Ile Thr Trp Asn
1               5                   10                  15

Ser Gly His Ile Asp Tyr Ala Asp Ser Val Glu Gly Arg
            20                  25

<210> SEQ ID NO 19
<211> LENGTH: 6
<212> TYPE: PRT
<213> ORGANISM: Artificial Sequence
<220> FEATURE:
<223> OTHER INFORMATION: Adalimumab tryptic peptide

<400> SEQUENCE: 19

Ala Ser Gln Gly Ile Arg
1               5

<210> SEQ ID NO 20
<211> LENGTH: 12
<212> TYPE: PRT
<213> ORGANISM: Artificial Sequence
<220> FEATURE:
<223> OTHER INFORMATION: Adalimumab tryptic peptide

<400> SEQUENCE: 20

Asn Tyr Leu Ala Trp Tyr Gln Gln Lys Pro Gly Lys
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Adalimumab tryptic peptide

<400> SEQUENCE: 21

Leu Leu Ile Tyr Ala Ala Ser Thr Leu Gln Ser Gly Val Pro Ser Arg
1               5                   10                  15

<210> SEQ ID NO 22
<211> LENGTH: 29
<212> TYPE: PRT
<213> ORGANISM: Artificial Sequence
<220> FEATURE:
<223> OTHER INFORMATION: Adalimumab tryptic peptide

<400> SEQUENCE: 22

Phe Ser Gly Ser Gly Ser Gly Thr Asp Phe Thr Leu Thr Ile Ser Ser
1               5                   10                  15

Leu Gln Pro Glu Asp Val Ala Thr Tyr Tyr Cys Gln Arg
            20                  25

<210> SEQ ID NO 23
<211> LENGTH: 10
<212> TYPE: PRT
<213> ORGANISM: Artificial Sequence
<220> FEATURE:
<223> OTHER INFORMATION: Adalimumab tryptic peptide

<400> SEQUENCE: 23

Ala Pro Tyr Thr Phe Gly Gln Gly Thr Lys
1               5                   10

<210> SEQ ID NO 24

```
<211> LENGTH: 19
<212> TYPE: PRT
<213> ORGANISM: Artificial Sequence
<220> FEATURE:
<223> OTHER INFORMATION: Certolizumab tryptic peptide

<400> SEQUENCE: 24

Leu Ser Cys Ala Ala Ser Gly Tyr Val Phe Thr Asp Tyr Gly Met Asn
1               5                   10                  15

Trp Val Arg

<210> SEQ ID NO 25
<211> LENGTH: 22
<212> TYPE: PRT
<213> ORGANISM: Artificial Sequence
<220> FEATURE:
<223> OTHER INFORMATION: Certolizumab tryptic peptide

<400> SEQUENCE: 25

Gly Leu Glu Trp Met Gly Trp Ile Asn Thr Tyr Ile Gly Glu Pro Ile
1               5                   10                  15

Tyr Ala Asp Ser Val Lys
            20

<210> SEQ ID NO 26
<211> LENGTH: 9
<212> TYPE: PRT
<213> ORGANISM: Artificial Sequence
<220> FEATURE:
<223> OTHER INFORMATION: Certolizumab tryptic peptide

<400> SEQUENCE: 26

Phe Thr Phe Ser Leu Asp Thr Ser Lys
1               5

<210> SEQ ID NO 27
<211> LENGTH: 11
<212> TYPE: PRT
<213> ORGANISM: Artificial Sequence
<220> FEATURE:
<223> OTHER INFORMATION: Certolizumab tryptic peptide

<400> SEQUENCE: 27

Ser Thr Ala Tyr Leu Gln Met Asn Ser Leu Arg
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Certolizumab tryptic peptide

<400> SEQUENCE: 28

Ala Ser Gln Asn Val Gly Thr Asn Val Ala Trp Tyr Gln Gln Lys Pro
1               5                   10                  15

Gly Lys

<210> SEQ ID NO 29
<211> LENGTH: 16
<212> TYPE: PRT
<213> ORGANISM: Artificial Sequence
<220> FEATURE:
<223> OTHER INFORMATION: Certolizumab tryptic peptide

<400> SEQUENCE: 29
```

```
Ala Leu Ile Tyr Ser Ala Ser Phe Leu Tyr Ser Gly Val Pro Tyr Arg
1               5                   10                  15
```

<210> SEQ ID NO 30
<211> LENGTH: 42
<212> TYPE: PRT
<213> ORGANISM: Artificial Sequence
<220> FEATURE:
<223> OTHER INFORMATION: Certolizumab tryptic peptide

<400> SEQUENCE: 30

```
Phe Ser Gly Ser Gly Ser Gly Thr Asp Phe Thr Leu Thr Ile Ser Ser
1               5                   10                  15

Leu Gln Pro Glu Asp Phe Ala Thr Tyr Tyr Cys Gln Gln Tyr Asn Ile
                20                  25                  30

Tyr Pro Leu Thr Phe Gly Gln Gly Thr Lys
                35                  40
```

<210> SEQ ID NO 31
<211> LENGTH: 19
<212> TYPE: PRT
<213> ORGANISM: Artificial Sequence
<220> FEATURE:
<223> OTHER INFORMATION: Golimumab tryptic peptide

<400> SEQUENCE: 31

```
Leu Ser Cys Ala Ala Ser Gly Phe Ile Phe Ser Ser Tyr Ala Met His
1               5                   10                  15

Trp Val Arg
```

<210> SEQ ID NO 32
<211> LENGTH: 20
<212> TYPE: PRT
<213> ORGANISM: Artificial Sequence
<220> FEATURE:
<223> OTHER INFORMATION: Golimumab tryptic peptide

<400> SEQUENCE: 32

```
Gln Ala Pro Gly Asn Gly Leu Glu Trp Val Ala Phe Met Ser Tyr Asp
1               5                   10                  15

Gly Ser Asn Lys
                20
```

<210> SEQ ID NO 33
<211> LENGTH: 31
<212> TYPE: PRT
<213> ORGANISM: Artificial Sequence
<220> FEATURE:
<223> OTHER INFORMATION: Golimumab tryptic peptide

<400> SEQUENCE: 33

```
Gly Ile Ala Ala Gly Gly Asn Tyr Tyr Tyr Tyr Gly Met Asp Val Ile
1               5                   10                  15

Ser Ser Gln Gly Thr Thr Val Thr Val Ser Ser Ala Ser Thr Lys
                20                  25                  30
```

<210> SEQ ID NO 34
<211> LENGTH: 15
<212> TYPE: PRT
<213> ORGANISM: Artificial Sequence
<220> FEATURE:
<223> OTHER INFORMATION: Golimumab tryptic peptide

<400> SEQUENCE: 34

```
Ala Ser Gln Ser Val Tyr Ser Tyr Leu Ala Trp Tyr Gln Gln Lys
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Golimumab tryptic peptide

<400> SEQUENCE: 35

Leu Leu Ile Tyr Asp Ala Ser Asn Arg
1               5

<210> SEQ ID NO 36
<211> LENGTH: 30
<212> TYPE: PRT
<213> ORGANISM: Artificial Sequence
<220> FEATURE:
<223> OTHER INFORMATION: Golimumab tryptic peptide

<400> SEQUENCE: 36

Phe Ser Gly Ser Gly Ser Gly Thr Asp Phe Thr Leu Thr Ile Ser Ser
1               5                   10                  15

Leu Glu Pro Glu Asp Phe Ala Val Tyr Tyr Cys Gln Gln Arg
            20                  25                  30

<210> SEQ ID NO 37
<211> LENGTH: 13
<212> TYPE: PRT
<213> ORGANISM: Artificial Sequence
<220> FEATURE:
<223> OTHER INFORMATION: Golimumab tryptic peptide

<400> SEQUENCE: 37

Ser Asn Trp Pro Pro Phe Thr Phe Gly Pro Gly Thr Lys
1               5                   10

<210> SEQ ID NO 38
<211> LENGTH: 239
<212> TYPE: PRT
<213> ORGANISM: Artificial Sequence
<220> FEATURE:
<223> OTHER INFORMATION: Infliximab IdeS proteolytic peptide (VH+CH1)

<400> SEQUENCE: 38

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly
225                 230                 235

<210> SEQ ID NO 39
<211> LENGTH: 214
<212> TYPE: PRT
<213> ORGANISM: Artificial Sequence
<220> FEATURE:
<223> OTHER INFORMATION: Infliximab IdeS proteolytic peptide (VL+CL)

<400> SEQUENCE: 39

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Met Ser Gly Ile Pro Ser Arg Phe Ser Gly
50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 256
<212> TYPE: PRT
<213> ORGANISM: Artificial Sequence
```

<220> FEATURE:
<223> OTHER INFORMATION: Etanercept IdeS proteolytic peptide

<400> SEQUENCE: 40

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255
```

<210> SEQ ID NO 41
<211> LENGTH: 240
<212> TYPE: PRT
<213> ORGANISM: Artificial Sequence
<220> FEATURE:
<223> OTHER INFORMATION: Adalimumab IdeS proteolytic peptide (VH+CH1)

<400> SEQUENCE: 41

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                    85                  90                  95
Ala Lys Val Ser Tyr Leu Ser Thr Ala Ser Ser Leu Asp Tyr Trp Gly
                100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

<210> SEQ ID NO 42
<211> LENGTH: 214
<212> TYPE: PRT
<213> ORGANISM: Artificial Sequence
<220> FEATURE:
<223> OTHER INFORMATION: Adalimumab IdeS proteolytic peptide(VL+CL)

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 43
<211> LENGTH: 229
<212> TYPE: PRT
<213> ORGANISM: Artificial Sequence
<220> FEATURE:
<223> OTHER INFORMATION: Certolizumab IdeS proteolytic peptide (VH+CH1)

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225
```

<210> SEQ ID NO 44
<211> LENGTH: 214
<212> TYPE: PRT
<213> ORGANISM: Artificial Sequence
<220> FEATURE:
<223> OTHER INFORMATION: Certolizumab IdeS proteolytic peptide (VL+CL)

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 246
<212> TYPE: PRT
<213> ORGANISM: Artificial Sequence
<220> FEATURE:
<223> OTHER INFORMATION: Golimumab IdeS proteolytic peptide (VH+CH1)

<400> SEQUENCE: 45

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Ile Ala Ala Gly Gly Asn Tyr Tyr Tyr Tyr Gly
            100                 105                 110

Met Asp Val Ile Ser Ser Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205
```

```
Ile Cys Asn Val Asn His Lys Pro Ser Asn Thr Lys Val Asp Lys Lys
    210                 215                 220
Val Glu Pro Lys Ser Cys Asp Lys Thr His Thr Cys Pro Pro Cys Pro
225                 230                 235                 240
Ala Pro Glu Leu Leu Gly
                245
```

<210> SEQ ID NO 46
<211> LENGTH: 215
<212> TYPE: PRT
<213> ORGANISM: Artificial Sequence
<220> FEATURE:
<223> OTHER INFORMATION: Golimumab IdeS proteolytic peptide (VL+CL)

<400> SEQUENCE: 46

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Tyr Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Pro
                85                  90                  95
Phe Thr Phe Gly Pro Gly Thr Lys Val Asp Ile Lys Arg Thr Val Ala
            100                 105                 110
Ala Pro Ser Val Phe Ile Phe Pro Pro Ser Asp Glu Gln Leu Lys Ser
    115                 120                 125
Gly Thr Ala Ser Val Val Cys Leu Leu Asn Asn Phe Tyr Pro Arg Glu
130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
    195                 200                 205
Ser Phe Asn Arg Gly Glu Cys
    210                 215
```

<210> SEQ ID NO 47
<211> LENGTH: 11
<212> TYPE: PRT
<213> ORGANISM: Artificial Sequence
<220> FEATURE:
<223> OTHER INFORMATION: Trastuzumab tryptic peptide

<400> SEQUENCE: 47

```
Leu Ser Cys Ala Ala Ser Gly Phe Asn Ile Lys
1               5                   10
```

<210> SEQ ID NO 48
<211> LENGTH: 8
<212> TYPE: PRT
<213> ORGANISM: Artificial Sequence

```
<220> FEATURE:
<223> OTHER INFORMATION: Trastuzumab tryptic peptide

<400> SEQUENCE: 48

Asp Thr Tyr Ile His Trp Val Arg
1               5

<210> SEQ ID NO 49
<211> LENGTH: 9
<212> TYPE: PRT
<213> ORGANISM: Artificial Sequence
<220> FEATURE:
<223> OTHER INFORMATION: Trastuzumab tryptic peptide

<400> SEQUENCE: 49

Ile Tyr Pro Thr Asn Gly Tyr Thr Arg
1               5

<210> SEQ ID NO 50
<211> LENGTH: 9
<212> TYPE: PRT
<213> ORGANISM: Artificial Sequence
<220> FEATURE:
<223> OTHER INFORMATION: Trastuzumab tryptic peptide

<400> SEQUENCE: 50

Phe Thr Ile Ser Ala Asp Thr Ser Lys
1               5

<210> SEQ ID NO 51
<211> LENGTH: 18
<212> TYPE: PRT
<213> ORGANISM: Artificial Sequence
<220> FEATURE:
<223> OTHER INFORMATION: Trastuzumab tryptic peptide

<400> SEQUENCE: 51

Ala Ser Gln Asp Val Asn Thr Ala Val Ala Trp Tyr Gln Gln Lys Pro
1               5                   10                  15

Gly Lys

<210> SEQ ID NO 52
<211> LENGTH: 16
<212> TYPE: PRT
<213> ORGANISM: Artificial Sequence
<220> FEATURE:
<223> OTHER INFORMATION: Trastuzumab tryptic peptide

<400> SEQUENCE: 52

Leu Leu Ile Tyr Ser Ala Ser Phe Leu Tyr Ser Gly Val Pro Ser Arg
1               5                   10                  15

<210> SEQ ID NO 53
<211> LENGTH: 37
<212> TYPE: PRT
<213> ORGANISM: Artificial Sequence
<220> FEATURE:
<223> OTHER INFORMATION: Trastuzumab tryptic peptide

<400> SEQUENCE: 53

Ser Gly Thr Asp Phe Thr Leu Thr Ile Ser Ser Leu Gln Pro Glu Asp
1               5                   10                  15

Phe Ala Thr Tyr Tyr Cys Gln Gln His Tyr Thr Thr Pro Pro Thr Phe
                20                  25                  30

Gly Gln Gly Thr Lys
```

```
<210> SEQ ID NO 54
<211> LENGTH: 19
<212> TYPE: PRT
<213> ORGANISM: Artificial Sequence
<220> FEATURE:
<223> OTHER INFORMATION: Rituximab tryptic peptide

<400> SEQUENCE: 54

Gln Val Gln Leu Gln Gln Pro Gly Ala Glu Leu Val Lys Pro Gly Ala
1               5                   10                  15

Ser Val Lys

<210> SEQ ID NO 55
<211> LENGTH: 15
<212> TYPE: PRT
<213> ORGANISM: Artificial Sequence
<220> FEATURE:
<223> OTHER INFORMATION: Rituximab tryptic peptide

<400> SEQUENCE: 55

Ala Ser Gly Tyr Thr Phe Thr Ser Tyr Asn Met His Trp Val Lys
1               5                   10                  15

<210> SEQ ID NO 56
<211> LENGTH: 20
<212> TYPE: PRT
<213> ORGANISM: Artificial Sequence
<220> FEATURE:
<223> OTHER INFORMATION: Rituximab tryptic peptide

<400> SEQUENCE: 56

Gly Leu Glu Trp Ile Gly Ala Ile Tyr Pro Gly Asn Gly Asp Thr Ser
1               5                   10                  15

Tyr Asn Gln Lys
            20

<210> SEQ ID NO 57
<211> LENGTH: 7
<212> TYPE: PRT
<213> ORGANISM: Artificial Sequence
<220> FEATURE:
<223> OTHER INFORMATION: Rituximab tryptic peptide

<400> SEQUENCE: 57

Ala Thr Leu Thr Ala Asp Lys
1               5

<210> SEQ ID NO 58
<211> LENGTH: 24
<212> TYPE: PRT
<213> ORGANISM: Artificial Sequence
<220> FEATURE:
<223> OTHER INFORMATION: Rituximab tryptic peptide

<400> SEQUENCE: 58

Ser Ser Ser Thr Ala Tyr Met Gln Leu Ser Ser Leu Thr Ser Glu Asp
1               5                   10                  15

Ser Ala Val Tyr Tyr Cys Ala Arg
            20

<210> SEQ ID NO 59
<211> LENGTH: 27
<212> TYPE: PRT
```

```
<213> ORGANISM: Artificial Sequence
<220> FEATURE:
<223> OTHER INFORMATION: Rituximab tryptic peptide

<400> SEQUENCE: 59

Ser Thr Tyr Tyr Gly Gly Asp Trp Tyr Phe Asn Val Trp Gly Ala Gly
1               5                   10                  15

Thr Thr Val Thr Val Ser Ala Ala Ser Thr Lys
            20                  25

<210> SEQ ID NO 60
<211> LENGTH: 18
<212> TYPE: PRT
<213> ORGANISM: Artificial Sequence
<220> FEATURE:
<223> OTHER INFORMATION: Rituximab tryptic peptide

<400> SEQUENCE: 60

Gln Ile Val Leu Ser Gln Ser Pro Ala Ile Leu Ser Ala Ser Pro Gly
1               5                   10                  15

Glu Lys

<210> SEQ ID NO 61
<211> LENGTH: 6
<212> TYPE: PRT
<213> ORGANISM: Artificial Sequence
<220> FEATURE:
<223> OTHER INFORMATION: Rituximab tryptic peptide

<400> SEQUENCE: 61

Val Thr Met Thr Cys Arg
1               5

<210> SEQ ID NO 62
<211> LENGTH: 36
<212> TYPE: PRT
<213> ORGANISM: Artificial Sequence
<220> FEATURE:
<223> OTHER INFORMATION: Rituximab tryptic peptide

<400> SEQUENCE: 62

Ala Ser Ser Ser Val Ser Tyr Ile His Trp Phe Gln Gln Lys Pro Gly
1               5                   10                  15

Ser Ser Pro Lys Pro Trp Ile Tyr Ala Thr Ser Asn Leu Ala Ser Gly
            20                  25                  30

Val Pro Val Arg
        35

<210> SEQ ID NO 63
<211> LENGTH: 16
<212> TYPE: PRT
<213> ORGANISM: Artificial Sequence
<220> FEATURE:
<223> OTHER INFORMATION: Rituximab tryptic peptide

<400> SEQUENCE: 63

Phe Ser Gly Ser Gly Ser Gly Thr Ser Tyr Ser Leu Thr Ile Ser Arg
1               5                   10                  15

<210> SEQ ID NO 64
<211> LENGTH: 26
<212> TYPE: PRT
<213> ORGANISM: Artificial Sequence
<220> FEATURE:
<223> OTHER INFORMATION: Rituximab tryptic peptide
```

<400> SEQUENCE: 64

Val Glu Ala Glu Asp Ala Ala Thr Tyr Tyr Cys Gln Gln Trp Thr Ser
1               5                   10                  15

Asn Pro Pro Thr Phe Gly Gly Gly Thr Lys
            20                  25

<210> SEQ ID NO 65
<211> LENGTH: 19
<212> TYPE: PRT
<213> ORGANISM: Artificial Sequence
<220> FEATURE:
<223> OTHER INFORMATION: Bevacizumab tryptic peptide

<400> SEQUENCE: 65

Leu Ser Cys Ala Ala Ser Gly Tyr Thr Phe Thr Asn Tyr Gly Met Asn
1               5                   10                  15

Trp Val Arg

<210> SEQ ID NO 66
<211> LENGTH: 22
<212> TYPE: PRT
<213> ORGANISM: Artificial Sequence
<220> FEATURE:
<223> OTHER INFORMATION: Bevacizumab tryptic peptide

<400> SEQUENCE: 66

Gly Leu Glu Trp Val Gly Trp Ile Asn Thr Tyr Thr Gly Glu Pro Thr
1               5                   10                  15

Tyr Ala Ala Asp Phe Lys
            20

<210> SEQ ID NO 67
<211> LENGTH: 9
<212> TYPE: PRT
<213> ORGANISM: Artificial Sequence
<220> FEATURE:
<223> OTHER INFORMATION: Bevacizumab tryptic peptide

<400> SEQUENCE: 67

Phe Thr Phe Ser Leu Asp Thr Ser Lys
1               5

<210> SEQ ID NO 68
<211> LENGTH: 11
<212> TYPE: PRT
<213> ORGANISM: Artificial Sequence
<220> FEATURE:
<223> OTHER INFORMATION: Bevacizumab tryptic peptide

<400> SEQUENCE: 68

Ser Thr Ala Tyr Leu Gln Met Asn Ser Leu Arg
1               5                   10

<210> SEQ ID NO 69
<211> LENGTH: 29
<212> TYPE: PRT
<213> ORGANISM: Artificial Sequence
<220> FEATURE:
<223> OTHER INFORMATION: Bevacizumab tryptic peptide

<400> SEQUENCE: 69

Tyr Pro His Tyr Tyr Gly Ser Ser His Trp Tyr Phe Asp Val Trp Gly
1               5                   10                  15

Gln Gly Thr Leu Val Thr Val Ser Ser Ala Ser Thr Lys
            20                  25

<210> SEQ ID NO 70
<211> LENGTH: 24
<212> TYPE: PRT
<213> ORGANISM: Artificial Sequence
<220> FEATURE:
<223> OTHER INFORMATION: Bevacizumab tryptic peptide

<400> SEQUENCE: 70

Val Thr Ile Thr Cys Ser Ala Ser Gln Asp Ile Ser Asn Tyr Leu Asn
1               5                   10                  15

Trp Tyr Gln Gln Lys Pro Gly Lys
            20

<210> SEQ ID NO 71
<211> LENGTH: 16
<212> TYPE: PRT
<213> ORGANISM: Artificial Sequence
<220> FEATURE:
<223> OTHER INFORMATION: Bevacizumab tryptic peptide

<400> SEQUENCE: 71

Val Leu Ile Tyr Phe Thr Ser Ser Leu His Ser Gly Val Pro Ser Arg
1               5                   10                  15

<210> SEQ ID NO 72
<211> LENGTH: 42
<212> TYPE: PRT
<213> ORGANISM: Artificial Sequence
<220> FEATURE:
<223> OTHER INFORMATION: Bevacizumab tryptic peptide

<400> SEQUENCE: 72

Phe Ser Gly Ser Gly Ser Gly Thr Asp Phe Thr Leu Thr Ile Ser Ser
1               5                   10                  15

Leu Gln Pro Glu Asp Phe Ala Thr Tyr Tyr Cys Gln Gln Tyr Ser Thr
            20                  25                  30

Val Pro Trp Thr Phe Gly Gln Gly Thr Lys
            35                  40

<210> SEQ ID NO 73
<211> LENGTH: 450
<212> TYPE: PRT
<213> ORGANISM: Artificial Sequence
<220> FEATURE:
<223> OTHER INFORMATION: Infliximab, heavy chain

<400> SEQUENCE: 73

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
            35                  40                  45

Ala Glu Ile Arg Ser Lys Ser Ile Asn Ser Ala Thr His Tyr Ala Glu
        50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

```
Tyr Cys Ser Arg Asn Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 74
<211> LENGTH: 214
<212> TYPE: PRT
<213> ORGANISM: Artificial Sequence
<220> FEATURE:
<223> OTHER INFORMATION: Infliximab, light chain

<400> SEQUENCE: 74
```

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
            35                  40                  45

Lys Tyr Ala Ser Glu Ser Met Ser Gly Ile Pro Ser Arg Phe Ser Gly
        50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 75
<211> LENGTH: 451
<212> TYPE: PRT
<213> ORGANISM: Artificial Sequence
<220> FEATURE:
<223> OTHER INFORMATION: Adalimumab, heavy chain

<400> SEQUENCE: 75

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 76
<211> LENGTH: 214
<212> TYPE: PRT
<213> ORGANISM: Artificial Sequence
<220> FEATURE:
<223> OTHER INFORMATION: Adalimumab, light chain

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
            35                  40                  45
```

```
Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210

<210> SEQ ID NO 77
<211> LENGTH: 467
<212> TYPE: PRT
<213> ORGANISM: Artificial Sequence
<220> FEATURE:
<223> OTHER INFORMATION: Etanercept

<400> SEQUENCE: 77

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190
```

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 78
<211> LENGTH: 229
<212> TYPE: PRT
<213> ORGANISM: Artificial Sequence
<220> FEATURE:
<223> OTHER INFORMATION: Certolizumab, heavy chain

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                 85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Val Glu Pro Lys Ser Cys Asp Lys Thr
    210                 215                 220

His Thr Cys Ala Ala
225

<210> SEQ ID NO 79
<211> LENGTH: 214
<212> TYPE: PRT
<213> ORGANISM: Artificial Sequence
<220> FEATURE:
<223> OTHER INFORMATION: Certolizumab, light chain

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 80
<211> LENGTH: 457
<212> TYPE: PRT
<213> ORGANISM: Artificial Sequence
<220> FEATURE:
<223> OTHER INFORMATION: Golimumab, heavy chain

<400> SEQUENCE: 80

Gln Val Gln Leu Val Glu Ser Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Ile Ser Ser Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
    435                 440                 445

Lys Ser Leu Ser Leu Ser Pro Gly Lys
    450                 455

<210> SEQ ID NO 81
<211> LENGTH: 215
<212> TYPE: PRT
<213> ORGANISM: Artificial Sequence
<220> FEATURE:
<223> OTHER INFORMATION: Golimumab, light chain

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 82
<211> LENGTH: 449
<212> TYPE: PRT
<213> ORGANISM: Artificial Sequence
<220> FEATURE:

<223> OTHER INFORMATION: Trastuzumab, heavy chain

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 83
<211> LENGTH: 214
<212> TYPE: PRT
<213> ORGANISM: Artificial Sequence
<220> FEATURE:
<223> OTHER INFORMATION: Trastuzumab, light chain

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 451
<212> TYPE: PRT
<213> ORGANISM: Artificial Sequence
<220> FEATURE:
<223> OTHER INFORMATION: Rituximab, heavy chain

<400> SEQUENCE: 84

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

-continued

```
Asn Met His Trp Val Lys Gln Thr Pro Gly Arg Gly Leu Glu Trp Ile
     35                  40                  45
Gly Ala Ile Tyr Pro Gly Asn Gly Asp Thr Ser Tyr Asn Gln Lys Phe
 50                  55                  60
Lys Gly Lys Ala Thr Leu Thr Ala Asp Lys Ser Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Ser Thr Tyr Tyr Gly Gly Asp Trp Tyr Phe Asn Val Trp Gly
             100                 105                 110
Ala Gly Thr Thr Val Thr Val Ser Ala Ala Ser Thr Lys Gly Pro Ser
         115                 120                 125
Val Phe Pro Leu Ala Pro Ser Ser Lys Ser Thr Ser Gly Gly Thr Ala
     130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
```

<210> SEQ ID NO 85
<211> LENGTH: 213
<212> TYPE: PRT
<213> ORGANISM: Artificial Sequence
<220> FEATURE:
<223> OTHER INFORMATION: Rituximab, light chain

<400> SEQUENCE: 85

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 86
<211> LENGTH: 453
<212> TYPE: PRT
<213> ORGANISM: Artificial Sequence
<220> FEATURE:
<223> OTHER INFORMATION: Bevacizumab, heavy chain

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80
```

-continued

```
Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450
```

<210> SEQ ID NO 87
<211> LENGTH: 214
<212> TYPE: PRT
<213> ORGANISM: Artificial Sequence
<220> FEATURE:
<223> OTHER INFORMATION: Bevacizumab, light chain

```
<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                      80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210
```

METHOD FOR QUANTIFYING THERAPEUTIC ANTIBODIES

CROSS-REFERENCE TO RELATED APPLICATIONS

This application is a U.S. National Stage Application pursuant to 35 U.S.C. § 371 of International Patent Application PCT/EP2016/076740, filed on Nov. 4, 2016, and published as WO 2017/077081 on May 11, 2017, which claims priority to European Patent Application 15306767, filed on Nov. 6, 2015, all of which are incorporated herein by reference in their entireties for all purposes.

FIELD OF THE INVENTION

This invention relates to the field of antibody quantification. It more precisely relates to the quantification of therapeutic antibodies in a biological sample.

BACKGROUND OF THE INVENTION

The analysis of plasma/serum samples generated from in vivo studies of therapeutic proteins, especially of therapeutic antibodies, is of interest in the biopharmaceutical industry.

Monoclonal antibodies (mAbs) are an upcoming group of therapeutic compounds used to treat various types of diseases. Monoclonal antibodies (mAbs) constitute a therapeutic class which knows the strongest current rate of development in the field of pharmaceutical biotechnology. There are to date more than 50 mAbs marketed in various fields such as oncology, immunology, ophthalmology and cardiology. Monoclonal antibodies have provided important medical results in the treatment of several major diseases including autoimmune, cardiovascular and infectious diseases, cancer and inflammation, clinical trials.

Antibody-based therapy for cancer has become established over the past 15 years and is now one of the most successful and important strategies for treating patients with hematological malignancies and solid tumors. The use of monoclonal antibodies for cancer therapy has achieved considerable success in recent years. Notably, antibody-drug conjugates are powerful new treatment options for lymphomas and solid tumours, and immunomodulatory antibodies have also recently achieved remarkable clinical success. The development of therapeutic antibodies requires a deep understanding of cancer serology, protein-engineering techniques, mechanisms of action and resistance, and the interplay between the immune system and cancer cells.

Among them, anti-TNF antibodies blocking the action of TNF alpha revolutionized therapy of TNF-related diseases such as Inflammatory Bowel Disease, lupus, ulcerative colitis, ankylosing spondylitis, psoriatic arthritis and rheumatoid arthritis. By neutralizing TNF activity, anti-TNF antibodies promote mucosal healing and induce long-term remissions in patients. The main anti-TNF antibodies that are currently authorized encompass Infliximab, Etanercept, Adalimumab, Certolizumab and Golimumab.

Given the polypeptide nature of therapeutic mAbs, their high degree of homology with the endogenous human IgGs and the low concentrations at which they are expected in the plasma environment, the determination of concentrations of therapeutic monoclonal antibodies in human plasma and human serum-derived samples is difficult. To establish the pharmacokinetic (PK) properties of mAbs in human samples, many clinical studies are executed. Samples of these studies are most often analyzed using immunoassays. Although immunoassays are very fast and sensitive, there are also some limitations.

The conventional ELISA approach has been used for over 25 years and has several limitations. The ELISA methods require high quality custom reagents that can take several months to generate and the assay optimization can take an additional number of months. Thus, ELISA has a long assay development time which is a limitation in both the early discovery stage and the development stage of protein-based drugs. Suitable ELISA reagents and assay conditions may not be possible in some cases due to the highly custom binding requirements for each protein therapeutic. Another limitation of ELISA is that reagents may bind non-specifically to plasma/serum proteins and matrix interference is a common phenomenon. Protein quantification by mass spectrometry on the other hand is highly specific and therefore matrix interference is rare compared to ELISA. Mass spectrometry methods of protein quantification, LC-MS/MS in particular, do not require custom reagents and generally yields faster assay development. In addition, mass spectrometry is less subject to matrix interferences and provides generic assay conditions which are highly specific and can be multiplexed and automated. The high specificity of mass spectrometry measures analyte concentration using intrinsic physical chemical properties of the analyte, i.e. mass and fragmentation pattern. The robust format allows ready lab-to-lab transfer, a significant advantage for approved antibody therapies. A general methodology for quantifying proteins by mass spectrometry is trypsin digestion of the intact protein. The resulting peptides are analyzed by mass spectrometry by introducing corresponding stable isotope labeled internal standards at a fixed concentration.

Liquid chromatography-tandem mass spectrometry is a powerful tool for protein analysis and quantitation in very complex matrices like plasma/serum samples. Since peptides resulting from the digestion of the protein of interest and other plasma/serum proteins may have the same or similar nominal mass, the second dimension of MS fragmentation often provides a unique fragment of a peptide of interest.

As it can be readily understood, methods for monitoring serum concentration of therapeutic antibodies shall be highly specific, sensitive, accurate and reproducible, so as to define the appropriate dosing adjustments that should be beneficial to a patient.

The present inventors have now identified that there is a need in the art for therapeutic antibodies quantification methods that would allow an accurate quantification of these antibodies in samples collected from patients subjected to antibody treatments, which quantification methods shall be useful irrespective of the kind of therapeutic antibody that has been administered to those patients and moreover, non-sensitive to the potential presence of other therapeutic antibodies previously administered. Notably, the present inventors have identified that there is a need for all-in-one simple methods allowing to quantify therapeutic antibodies in samples of treated patients, which methods would not require that the medical practitioners select a specific kit or method according to the specific therapeutic antibody that is expected to be contained in the patient samples.

SUMMARY OF THE INVENTION

The present invention relates to a method for quantifying a therapeutic antibody in a sample of a human individual comprising the steps of:

a) adding to a test sample which may contain therapeutic antibodies a known amount of two or more labeled forms of said therapeutic antibodies, whereby a pre-proteolysis sample is provided, b) subjecting the pre-proteolysis sample to an enzyme proteolysis, so as to provide a proteolysis sample comprising (i) proteolysis labeled peptides derived from the labeled therapeutic antibodies and (ii) proteolysis peptides derived from the therapeutic antibody contained in the test sample, c) determining by mass spectrometric analysis the ratio between (i) one or more selected proteolysis labeled peptides and (ii) one or more corresponding proteolysis peptides derived from the said therapeutic antibody, d) calculating from the ratio determined at step c) the amount of the said therapeutic antibody in the test sample.

In some embodiments, the two or more therapeutic antibodies consist of anti-TNF therapeutic antibodies. According to some aspects of these embodiments, the therapeutic anti-TNF antibodies are selected in a group comprising Infliximab, Etanercept, Adalimumab, Certolizumab and Golimumab.

In some embodiments, the two or more therapeutic antibodies consist of anti-cancer therapeutic antibodies. According to some aspects of these embodiments, the therapeutic anti-cancer antibodies are selected in a group comprising Trastuzumab, Rituximab and Bevacizumab.

In some embodiments of the method, step b) comprises the following steps:
b1) a step of enzyme proteolysis in denaturing conditions, and
b2) a step of enzyme proteolysis in non-denaturing conditions.

In some embodiments of the method, enzyme proteolysis is performed at step b) by using trypsin.

According to some aspects of these embodiments of the method, the one or more selected proteolysis peptides are selected in a group comprising:
for Infliximab, peptides of the amino acid sequences of SEQ ID NO. 1 to 8,
for Etanercept, peptides of the amino acid sequences of SEQ ID NO. 9 to 15,
for Adalimumab, peptides of the amino acid sequences of SEQ ID NO. 16 to 23,
for Certolizumab, peptides of the amino acid sequences of SEQ ID NO. 24 to 30, and
for Golimumab, peptides of the amino acid sequences of SEQ ID NO. 31 to 37,
for Trastuzumab, peptides of the amino acid sequences of SEQ ID NO. 47-53,
for Rituximab, peptides of the amino acid sequences of SEQ ID NO. 54-64, and
for Bevacizumab, peptides of the amino acid sequences of SEQ ID NO. 65-72.

In some other embodiments of the method, enzyme proteolysis is performed at step b) by incubating the pre-proteolysis sample with a hinge-targeting protease, such as an Immunoglobulin-degrading enzyme from *Streptococcus* (ideS).

According to some aspects of these other embodiments of the method, the one or more selected proteolysis peptides are selected in a group comprising:
for Infliximab, peptides of the amino acid sequences of SEQ ID NO. 38 and 39,
for Etanercept, a peptide of the amino acid sequence of SEQ ID NO. 40,
for Adalimumab, the peptides of the amino acid sequences of SEQ ID NO. 41 and 42,
for Certolizumab, the peptides of the amino acid sequences of SEQ ID NO. 43 and 44, and
for Golimumab, the peptides of the amino acid sequences of SEQ ID NO. 45 and 46.

According to some embodiments of the method, step a) comprises the following steps:
a1) adding to a test sample which may contain therapeutic antibodies to be quantified a known amount of two or more labeled forms of said therapeutic antibodies, whereby a non-concentrated pre-proteolysis sample is provided, and
a2) enriching the non-concentrated pre-proteolysis sample in antibodies, whereby a pre-proteolysis sample is provided.

In some embodiments of step a1), the said therapeutic antibodies consist of anti-TNF therapeutic antibodies. According to some aspects of these embodiments, the said anti-TNF antibodies are selected in a group comprising Infliximab, Etanercept, Adalimumab, Certolizumab and Golimumab In some preferred embodiments of the method, the test sample is a human sample from an individual who has been administered with an anti-TNF antibody selected in a group comprising Infliximab, Etanercept, Adalimumab, Certolizumab and Golimumab.

In some other embodiments of step a1), the said therapeutic antibodies consist of anti-cancer antibodies. According to some aspects of these embodiments, the said anti-cancer antibodies are selected in a group comprising Trastuzumab, Rituximab and Bevacizumab.

In some preferred embodiments of the method, the test sample is a human sample from an individual who has been administered with an anti-cancer antibody selected in a group comprising Trastuzumab, Rituximab and Bevacizumab.

The present invention also relates to kits for quantifying therapeutic antibodies comprising two or more stable Isotopically Labeled therapeutic antibodies.

In particular, the present invention also relates to kits that are useful for performing the anti-TNF antibodies quantification method that is described herein.

Thus, the present invention also relates to kits comprising two or more stable Isotopically Labeled therapeutic antibodies; for quantifying therapeutic antibodies in a human individual or a sample of a human individual.

The present invention also pertains to kits comprising two or more stable Isotopically Labeled therapeutic antibodies; for quantifying therapeutic anti-TNF antibodies in a human individual or a sample of a human individual.

This present invention also concerns to kits comprising two or more stable Isotopically Labeled therapeutic antibodies; for quantifying therapeutic anti-cancer antibodies in a human individual or a sample of a human individual.

Ordinate: Measured concentration of Infliximab as expressed in µg/mL. Abscissa: expected concentration of Infliximab as expressed in µg/mL.

Figure 2:
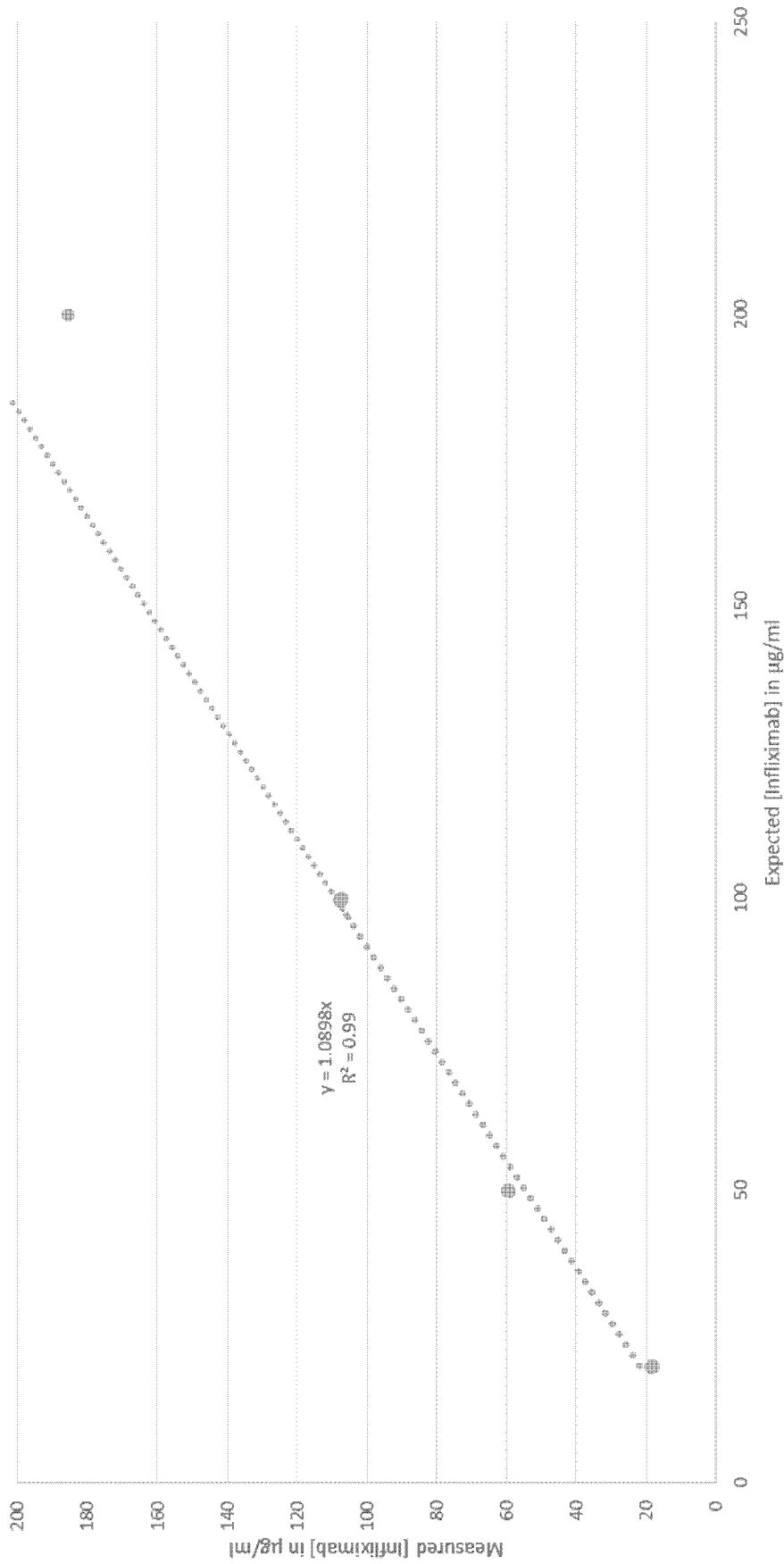

FIG. 2: Evaluation of the maximum concentration of anti-TF antibodies which can be present in a test sample without affecting antigen-capture when using the MSIA method.

Ordinate: Measured concentration of Infliximab as expressed in µg/mL. Abscissa: expected concentration of Infliximab as expressed in µg/mL.

Figure 3:
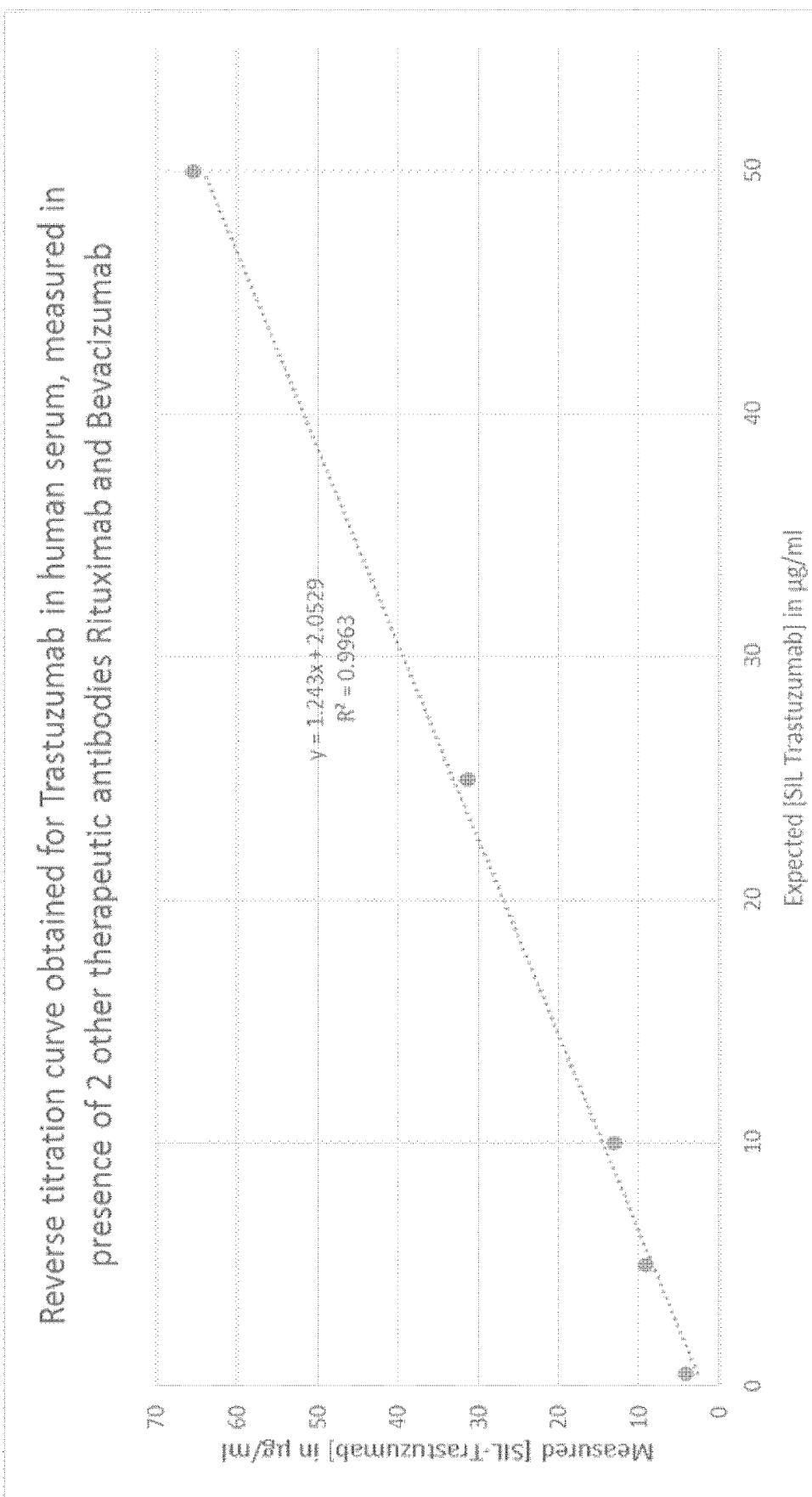

FIG. 3: Titration curve obtained for Trastuzumab in human serum measured in the presence of two distinct therapeutic antibodies, namely Rituximab and Bevacizumab.

Ordinate: Measured concentration of Trastuzumab as expressed in µg/mL. Abscissa: expected concentration of Trastuzumab as expressed in µg/mL.

DETAILED DESCRIPTION OF THE INVENTION

This invention provides a method for quantifying a therapeutic antibody in samples of human individuals that are treated with therapeutic antibodies, which method allows a precise quantification of these therapeutic antibodies, irrespective of the identity of the therapeutic antibody that is contained in the said sample to be tested.

The availability of the therapeutic antibody quantification method that is described herein now provides the practitioners with a single method that may be used generally with samples of any human individual who receives a therapeutic treatment with antibodies, without taking care of the kind of therapeutic antibody that has been administered to the said human individual.

Notably, in medical care units where some patients receive a treatment with a first anti-TNF antibody (e.g. Infliximab) and where some other patients receive a treatment with a second anti-TNF antibody (e.g. Etanercept), the use of the antibody quantification method described herein no more requires a selection of an anti-TNF antibody-specific quantification method as it is the case according to the present usual practice.

Also, in specialized medical care units, e.g. in cancer-specialized care units, where a plurality of anti-cancer antibody treatments are performed, depending on the kind of cancers that are treated, the use of the antibody quantification method described herein neither requires a selection of an anti-cancer antibody specific quantification method, nor a selection of an antibody specific sample preparation protocol as it is the case according to the usual practice.

Further, in situations wherein a patient's treatment is erroneously documented, e.g. in situations wherein the said patient is deemed having received a first therapeutic antibody (e.g. (i) Infliximab or (ii) Trastuzumab) but has actually received a second antibody (e.g. (i) Golimumab or (ii) Rituximab), the antibody quantification method described herein nevertheless allows (i) determining which therapeutic antibody (e.g. (i) the specific anti-TNF antibody used or (ii) the specific anti-cancer antibody used) the said patient has actually received and (ii) quantifying the therapeutic antibody that has been administered to the said patient, despite the erroneous information provided to the test laboratory relating to the therapeutic antibody actually used.

Still further, in situations wherein the patient is subjected to a combination therapy by being administered with more than one therapeutic antibody, the determination of the global circulating amount of therapeutic antibodies, irrespective of the identity and of the number of therapeutic antibodies that are used, may be performed globally by using the therapeutic antibody quantification method that is described herein.

Yet further, in situations wherein the patient received a first treatment based on a first therapeutic antibody (e.g. a first anti-TNF antibody) and then a second treatment based on a second therapeutic antibody (e.g. a second anti-TNF antibody), it follows that during a period of time subsequent to the said switch of treatment, both therapeutic antibodies will be present in the patient's body fluids, mainly in the patient's plasma. In these situations, the therapeutic antibody quantification method described herein allows quantification of the whole therapeutic antibodies in the said patient and also allows quantifying the respective amounts (e.g. plasma concentration) of each of the therapeutic antibodies administered.

The present invention provides a method for quantifying one or more therapeutic antibodies in human test samples, the said method allowing the quantification of said therapeutic antibodies, even when the nature of the antibodies that were administered to the tested patients is not precisely known.

For performing the quantification method described herein, the labeled forms of two or more therapeutic antibodies, i.e. the two labeled therapeutic antibodies, are labeled forms of therapeutic antibodies that are susceptible to be present in the human sample to be tested.

Illustratively, for quantifying therapeutic antibodies susceptible to be contained in human samples originating form medical care units hosting patients treated with anti-TNF antibodies and wherein a plurality of therapeutic anti-TNF antibodies are currently used for various treatments, then two or more of the labeled forms of the said therapeutic anti-TNF antibodies are added at step a) of the quantification method. Illustratively, for quantifying therapeutic anti-TNF antibodies in human samples originating from medical care units that make use of either Infliximab, Etanercept and Adalimumab, then the labeled forms of Infliximab, Etanercept and Adalimumab are added at step a) of the quantification method. Indeed, a higher number of labeled therapeutic antibodies, e.g. a higher number of labeled therapeutic anti-TNF antibodies, may be added at step a) of the method, e.g. the five therapeutic anti-TNF antibodies Infliximab, Etanercept, Adalimumab, Certolizumab and Golimumab. Such embodiments of the quantification method enable to perform the same embodiment of the quantification method described herein, e.g. with addition of five therapeutic anti-TNF antibodies, for quantifying anti-TNF antibodies in human samples provided by a plurality of medical care units making use of distinct anti-TNF antibodies, such as (i) a first medical care unit that performs treatments with Infliximab or Adalimumab, (ii) a second medical care unit that performs treatments with Etanercept, Adalimumab or Golimumab and (iii) a third medical care unit that performs treatments with Infliximab, Certolizumab and Golimumab. As it is illustrated, the therapeutic antibody quantification method described herein may be performed within the premises of a testing platform unit that centralizes the testing of human samples originating from a plurality of medical care units.

Further illustratively, for quantifying therapeutic antibodies susceptible to be contained in human samples originating form medical care units hosting patients treated with anti-cancer antibodies and wherein a plurality of therapeutic anti-cancer antibodies are currently used for various treatments, then two or more of the labeled forms of the said therapeutic anti-cancer antibodies are added at step a) of the quantification method. Illustratively, for quantifying therapeutic anti-cancer antibodies in human samples originating from medical care units that make use of either Trastuzumab, Rituximab and Bevacizumab, then the labeled forms of Trastuzumab, Rituximab and Bevacizumab are added at step a) of the quantification method. Indeed, a higher number of labeled therapeutic antibodies, e.g. a higher number of labeled therapeutic anti-cancer antibodies, may be added at step a) of the method, e.g. the three therapeutic anti-cancer antibodies Trastuzumab, Rituximab and Bevacizumab.

Still illustratively, for quantifying therapeutic antibodies susceptible to be contained in human samples originating form medical care units hosting patients treated with anti-TNF antibodies and anti-cancer antibodies and wherein a plurality of therapeutic anti-TNF antibodies and therapeutic anti-cancer antibodies are currently used for various treatments (e.g. for cancer treatments and rheumatoid arthritis for example), then two or more of the labeled forms of the said therapeutic antibodies are added at step a) of the quantification method. Illustratively, for quantifying therapeutic antibodies in human samples originating from medical care units that make use of either Trastuzumab, Rituximab and Infliximab, then the labeled forms of Trastuzumab, Rituximab and Infliximab are added at step a) of the quantification method. Indeed, a higher number of labeled therapeutic antibodies, e.g. a higher number of labeled therapeutic anti-TNF antibodies and of anti-cancer antibodies, may be added at step a) of the method, e.g. the eight therapeutic antibodies Trastuzumab, Rituximab, Bevacizumab, Infliximab, Etanercept, Adalimumab, Certolizumab and Golimumab.

Thus, according to the therapeutic antibody quantification method described herein, a test sample "which may contain therapeutic antibodies" means a human sample which is expected to comprise at least one therapeutic antibody to be quantified by an embodiment of the quantification method wherein two or more labeled therapeutic antibodies are added at step a) and wherein at least a labeled form of the said at least one therapeutic antibody, included in the said two or more labeled therapeutic antibodies, are added at step a). Thus, step a) comprises adding a known amount of two or more labeled forms of therapeutic antibodies to a test sample which is suspected to contain one or more therapeutic antibodies and wherein one or more of the said labeled forms of therapeutic antibodies include a labeled form of the one or more therapeutic antibodies expected to be contained in the said test sample.

As used herein, "a" or "at least one" encompasses "one", or "more than one"; which encompasses a "plurality of therapeutic antibodies", such as two, or more than two, which may encompass, three, four, five, or even more than five therapeutic antibodies.

Accordingly, the therapeutic antibody quantification methods described herein are suitable for quantifying a therapeutic antibody in a sample of a human individual, which encompasses the quantification of at least one therapeutic antibody in a sample of a human individual; which encompasses the quantification of two or more (a plurality) of therapeutic antibodies in a sample of a human individual.

Thus, the invention relates to a method for quantifying two or more therapeutic antibodies in a sample of a human individual, as defined above, in which the test sample may contain two or more of said therapeutic antibodies to be quantified.

As used herein, the expression "comprises" or "comprising" encompasses also "consists of" or "consisting of".

As used herein, a "therapeutic antibody" refers to an antibody that is suitable for use as a medicament, and which may consist either of a whole antibody or a fragment thereof; which includes any fragment selected from a group comprising: human antibodies, humanized antibodies, synthetic antibodies, and chimeric antibodies. Most therapeutic antibodies are monoclonal antibodies, in particular of the IgG type. Fragments thereof may be selected from the group consisting of: Fab, F(ab')2, scFv, Fc, pFc, Heavy chain and Light chain.

In some specific embodiments, this invention relates to a method for quantifying a therapeutic antibody in a sample of a human individual that has received a therapeutic treatment with a therapeutic antibody, including an anti-TNF and/or an anti-cancer therapeutic antibody.

According to some aspects of these embodiments, the said two or more anti-TNF therapeutic antibodies are selected in a group comprising Infliximab, Etanercept, Adalimumab, Certolizumab and Golimumab.

In some other specific embodiments, relates to a method for quantifying a therapeutic antibody in a sample of a human individual that has received a therapeutic treatment with an anti-cancer therapeutic antibody. According to some aspects of these embodiments, the said two or more anti-cancer therapeutic antibodies are selected in a group comprising Trastuzumab, Rituximab and Bevacizumab.

The quantification method that is described herein allows the quantification of two or more therapeutic antibodies, irrespective of the identity of the said therapeutic antibodies. The therapeutic antibodies to be quantified by the method described herein may be any antibodies of therapeutic interest, e.g. any therapeutic antibody that is the subject of a marketing authorization, at the time of performing the said therapeutic antibody quantification method.

Illustratively, the therapeutic antibody quantification method described herein may be performed for two or more antibodies selected in a group comprising Abagovomab, Abatacept, Abciximab, Abituzumab, Abrilumab, Actoxumab, Adalimumab, Adecatumab, Aducanumab, Aflibercept, Afutuzymab, Alacizumab, Alefacept, Alemtuzumab, Alirocumab, Altumomab, Amatixumab, Anatumomab, Anetumab, Anifromumab, Anrukinzumab, Apolizumab, Arcitumomab, Ascrinvacumab, Aselizumab, Atezolizumab, Atinumab, Altizumab, Atorolimumab, Bapineuzumab, Basiliximab, Bavituximab, Bectumomab, Begelomab, Belatacept, Belimumab, Benralizumab, Bertilimumab, Besilesomab, Bevacizumab, Bezlotoxumab, Biciromab, Bimagrumab, Bimekizumab, Bivatuzumab, Blinatumomab, Blosozumab, Bococizumab, Brentuximab, Briakimumab, Brodalumab, Brolucizumab, Bronticizumab, Canakinumab, Cantuzumab, Caplacizumab, Capromab, Carlumab, Catumaxomab, Cedelizumab, Certolizumab, Cetixumab, Citatuzumab, Cixutumumab, Clazakizumab, Clenoliximab, Clivatuzumab, Codrituzumab, Coltuximab, Conatumumab, Concizumab, Crenezumab, Dacetuzumab, Daclizumab, Dalotuzumab, Dapirolizumab, Daratumumab, Dectrekumab, Demcizumab, Denintuzumab, Denosumab, Derlotixumab, Detumomab, Dinutuximab, Diridavumab, Dorlinomab, Drozitumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab, Enlimomab, Enoblituzumab, Enokizumab, Enoticumab, Ensituximab, Epitumomab, Epratuzomab, Erlizumab, Ertumaxomab, Etanercept, Etaracizumab, Etrolizumab, Evinacumab, Evolocumab, Exbivirumab, Fanolesomab, Faralimomab, Farletuzomab, Fasimumab, Felvizumab, Fezkimumab, Ficlatuzumab, Figitumumab, Firivumab, Flanvotumab, Fletikumab, Fontolizumab, Foralumab, Foravirumab, Fresolimumab, Fulramumab, Futuximab, Galiximab, Ganitumab, Gantenerumab, Gavilimomab, Gemtuzumab, Gevokizumab, Girentuximab, Glembatumumab, Golimumab, Gomiliximab, Guselkumab, Ibalizumab, Ibritumomab, Icrucumab, Idarucizumab, Igovomab, Imalumab, Imciromab, Imgatuzumab, Inclacumab, Indatuximab, Indusatumab, Infliximab, Intetumumab, Inolimomab, Inotuzumab, Ipilimumab, Iratumumab, Isatuximab, Itolizumab, Ixekizumab, Keliximab, Labetuzumab, Lambrolizumab, Lampalizumab, Lebrikizumab, Lemalesomab, Lenzilumab, Lerdelimumab, Lexatumumab, Libivirumab, Lifastuzumab, Ligelizumab, Lilotomab, Lintuzumab, Lirilumab, Lodelcizumab, Lokivetmab, Lorvotuzumab, Lucatumumab, Lulizumab, Lumiliximab, Lumretuzumab, Mapatumumab, Margetuximab, Maslimomab, Mavrilimumab, Matuzumab, Mepolizumab, Metelimumab, Milatuzumab, Minetumomab, Mirvetuximab, Mitumomab, Mogamulizumab, Morolimumab, Motavizumab, Moxetumomab, Muromonab-CD3, Nacolomab, Namilumab, Naptumomab, Namatumab, Natalizumab, Nebacumab, Necitumumab, Nemolizumab, Nerelimomab, Nesvacumab, Nimotuzumab, Nivolumab, Nofetumomab, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab, Oregovomab, Orticumab, Otelixizumab, Oltertuzumab, Oxelumab, Ozanezumab, Ozoralizumab, Pagibaximab, Palivizumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab, Pintumomab, Polatuzumab, Ponezumab, Priliximab, Pritumumab, Quilizumab, Racotumomab, Radretumab, Rafivirumab, Ralpancizumab, Ramucirumab, Ranibizumab, Raxibacumab, Refanezumab, Regavirumab, Reslizumab, Rilonacept, Rilotumumab, Rinucumab, Rituximab, Robatumumab, Roledumab, Romosozumab, Rontalizumab, Rovelizumab, Ruplizumab, Sacituzumab, Samalizumab, Sarilumab, Satumomab, Secukimumab, Seribantumab, Setoxaximab, Sevirumab, Sibrotuzumab, Sifalimumab, Siltuximab, Siplizumab, Sirukumab, Sofituzumab, Solanezumab, Solitomab, Sonepcizumab, Sontuzumab, Stamulumab, Sulesomab, Suvizumab, Tabalumab, Tacatuzumab, Tadocizumab, Talizumab, Tanezumab, Taplitumomab, Tarextumab, Tefibazumab, Telimomab aritox, Tenatumomab, Teneliximab, Teplizumab, Tesidolumab, TGN 1412, Ticlimumab, Tildrakizumab, Tigatuzumab, TNX-650, Tocilizumab, Toralizumab, Tosatoxumab, Tositumomab, Tovetumab, Tralokimumab, Trastuzumab, TRBS07, Tregalizumab, Tremelimumab, Trevogrumab, Tucotuzumab, Tuvirumab, Ublituximab, Ulocuplumab, Urelumab, Urtoxazumab, Ustekimumab, Vandortuzumab, Vantictumab, Vanucizumab, Vapaliximab, Varlimumab, Vatelizumab, Vedolizumab, Veltuzumab, Vepalimomab, Vesencumab, Visilizumab, Volocixumab, Vorsetuzumab, Votumumab, Zalutumumab, Zanolimumab, Zatuximab, Ziralimumab, Ziv-Aflibercept, and Zolimomab.

In some embodiments, the therapeutic antibody quantification method described herein may be performed for two or more antibodies selected in a group comprising Infliximab, Etanercept, Adalimumab, Certolizumab, Golimumab, Trastuzumab, Rituximab and Bevacizumab.

In some embodiments, the therapeutic antibody quantification method described herein may be performed for two or more antibodies selected in a group comprising Infliximab, Etanercept, Adalimumab, Certolizumab and Golimumab.

In some embodiments, the therapeutic antibody quantification method described herein may be performed for two or more antibodies selected in a group comprising Trastuzumab, Rituximab and Bevacizumab.

Infliximab Etanercept, Adalimumab, Certolizumab and Golimumab are polypeptides, the respective sequences of which are described hereunder.

-For Infliximab:
(Heavy chain, SEQ ID NO. 73)
EVKLEESGGGLVQPGGSMKLSCVASGFIFSNHWMNWVRQSPEKGLEWVAE

IRSKSINSATHYAESVKGRFTISRDDSKSAVYLQMTDLRTEDTGVYYCSR

NYYGSTYDYWGQGTTLTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK (Light chain, SEQ ID NO. 74)
DILLTQSPAILSVSPGERVSFSCRASQFVGSSIHWYQQRTNGSPRLLIKY

ASESMSGIPSRFSGSGSGTDFTLSINTVESEDIADYYCQQSHSWPFTFGS

GTNLEVKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

-For Adalimumab:
(Heavy chain, SEQ ID NO. 75)
EVQLVESGGGLVQPGRSLRLSCAASGFTFDDYAMHWVRQAPGKGLEWVSA

ITWNSGHIDYADSVEGRFTISRDNAKNSLYLQMNSLRAEDTAVYYCAKVS

YLSTASSLDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K (Light chain, SEQ ID NO. 76)
DIQMTQSPSSLSASVGDRVTITCRASQGIRNYLAWYQQKPGKAPKLLIYA

ASTLQSGVPSRFSGSGSGTDFTLTISSLQPEDVATYYCQRYNRAPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

-For Etanercept:
(SEQ ID NO. 77)
LPAQVAFTPYAPEPGSTCRLREYYDQTAQMCCSKCSPGQHAKVFCTKTSD

TVCDSCEDSTYTQLWNWVPECLSCGSRCSSDQVETQACTREQNRICTCRP

GWYCALSKQEGCRLCAPLRKCRPGFGVARPGTETSDVVCKPCAPGTFSNT

TSSTDICRPHQICNVVAIPGNASMDAVCTSTSPTRSMAPGAVHLPQPVST

RSQHTQPTPEPSTAPSTSFLLPMGPSPPAEGSTGDEPKSCDKTHTCPPCP

APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHE
ALHNHYTQKSLSLSPGK

-For Certolizumab:
(Heavy chain, SEQ ID NO. 78)
EVQLVESGGGLVQPGGSLRLSCAASGYVFTDYGMNWVRQAPGKGLEWMGW
INTYIGEPIYADSVKGRFTFSLDTSKSTAYLQMNSLRAEDTAVYYCARGY
RSYAMDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCAA (Light chain, SEQ ID NO. 79)
DIQMTQSPSSLSASVGDRVTITCKASQNVGTNVAWYQQKPGKAPKALIYS
ASFLYSGVPYRFSGSGSGTDFTLTISSLQPEDFATYYCQQYNIYPLTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC -For Golimumab:
(Heavy chain, SEQ ID NO. 80)
QVQLVESGGGVVQPGRSLRLSCAASGIFSSYAMHWVRQAPGNGLEWVAF
MSYDGSNKKYADSVKGRFTISRDNSKNTLYLQMNSLRAEDTAVYYCARDR
GIAAGGNYYYYGMDVISSQGTTVTVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LSLSPGK (Light chain, SEQ ID NO. 81)
EIVLTQSPATLSLSPGERATLSCRASQSVYSYLAWYQQKPGQAPRLLIYD
ASNRATGIPARFSGSGSGTDFTLTISSLEPEDFAVYYCQQRSNWPPFTFG
PGTKVDIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Trastuzumab, Rituximab and Bevacizumab are polypeptides, the respective sequences of which are described hereunder.

-For Trastuzumab:
(Heavy chain, SEQ ID NO. 82)
EVQLVESGGGLVQPGGSLRLSCAASGFNIKDTYIHWVRQAPGKGLEWVAR
IYPTNGYTRYADSVKGRFTISADTSKNTAYLQMNSLRAEDTAVYYCSRWG
GDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPG (Light chain, SEQ ID NO. 83)
DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC -For Rituximab:
(Heavy chain, SEQ ID NO. 84)
QVQLQQPGAELVKPGASVKMSCKASGYTFTSYNMHWVKQTPGRGLEWIGA
IYPGNGDTSYNQKFKGKATLTADKSSSTAYMQLSSLTSEDSAVYYCARST
YYGGDWYFNVWGAGTTVTVSAASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG
K (Light chain, SEQ ID NO. 85)
QIVLSQSPAILSASPGEKVTMTCRASSSVSYIHWFQQKPGSSPKPWIYAT
SNLASGVPVRFSGSGSGTSYSLTISRVEAEDAATYYCQQWTSNPPTFGGG
TKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC -For Bevacizumab:
(Heavy chain, SEQ ID NO. 86)
EVQLVESGGGLVQPGGSLRLSCAASGYTFTNYGMNWVRQAPGKGLEWVGW
INTYTGEPTYAADFKRRFTFSLDTSKSTAYLQMNSLRAEDTAVYYCAKYP
HYYGSSHWYFDVWGQGTLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLS
PGK (Light chain, SEQ ID NO. 87)
DIQMTQSPSSLSASVGDRVTITCSASQDISNYLNWYQQKPGKAPKVLIYF
TSSLHSGVPSRFSGSGSGTDFTLTISSLQPEDFATYYCQQYSTVPWTFGQ -continued

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

This invention pertains to such a therapeutic antibody quantification method, which method makes use of a LC-MS/MS quantification technique.

Generally, for performing the therapeutic antibody quantification method described herein, two or more reference therapeutic antibodies (also termed "Internal Standard compounds" herein) are added to a test sample, before subjecting the resulting sample (also termed a "pre-proteolysis sample" to enzyme proteolysis, so as to provide a "proteolysis sample" comprising (i) proteolysis peptides derived from the reference therapeutic antibodies and (ii) proteolysis peptides derived from the therapeutic antibody contained in the test sample. At a further step of the method, the amount of the therapeutic antibodies that were initially contained in the test sample is determined by a mass spectrometry method, which includes the calculation of a ratio between (i) one or more selected proteolysis peptides derived from the reference therapeutic antibodies and (ii) one or more corresponding proteolysis peptides derived from the said therapeutic antibodies susceptible to be initially contained in the test sample.

Indeed, for performing the therapeutic antibody quantification method described herein, it is essential that (i) a given proteolysis peptide derived from a reference therapeutic antibody (Internal Standard compound) and (ii) the corresponding proteolysis peptide derived from the therapeutic antibody initially contained in the test sample be distinguished by the respective spectrometry signals that are generated by these peptides, so as to enable the calculation of a ratio between (i) the said proteolysis peptide derived from the said reference therapeutic antibody and (ii) the said corresponding proteolysis peptide derived from the therapeutic antibody initially contained in the test sample.

In preferred embodiments of the therapeutic antibody quantification method described herein, these proteolysis peptides may be distinguished by mass spectrometry by using a Internal Standard compound consisting of a labeled therapeutic antibody, and most preferably a Stable Isotopically Labeled (SIL) therapeutic antibody.

Indeed, the therapeutic antibody quantification method described herein is specifically designed for quantifying the amount (e.g. the concentration) of therapeutic antibodies contained in body fluids from a patient treated with such therapeutic antibodies, i.e. non-labeled therapeutic antibodies, so that the reference therapeutic antibodies are most preferably labeled therapeutic antibodies, and most preferably Stable Isotopically Labeled (SIL) therapeutic antibodies, as it is fully illustrated throughout the entire present specification.

The present invention concerns a method for quantifying a therapeutic antibody in a sample of a human individual comprising the steps of:
  a) adding to a test sample which may contain therapeutic antibodies to be quantified a known amount of two or more labeled forms of said therapeutic antibodies, whereby a pre-proteolysis sample is provided,
  b) subjecting the pre-proteolysis sample to an enzyme proteolysis, so as to provide a proteolysis sample comprising (i) proteolysis labeled peptides derived from the labeled therapeutic antibodies and (ii) proteolysis peptides derived from the therapeutic antibody contained in the test sample,
  c) determining by mass spectrometric analysis the ratio between (i) one or more selected proteolysis labeled peptides and (ii) one or more corresponding proteolysis peptides derived from the said therapeutic antibody,
  d) calculating from the ratio determined at step c) the amount of the said therapeutic antibody in the test sample.

In some embodiments of step a), the said therapeutic antibodies consist of anti-TNF therapeutic antibodies. According to some aspects of these embodiments, the said anti-TNF antibodies are selected in a group comprising Infliximab, Etanercept, Adalimumab, Certolizumab and Golimumab In some preferred embodiments of the method, the test sample is a human sample from an individual who has been administered with an anti-TNF antibody selected in a group comprising Infliximab, Etanercept, Adalimumab, Certolizumab and Golimumab.

In some other embodiments of step a), the said therapeutic antibodies consist of anti-cancer antibodies. According to some aspects of these embodiments, the said anti-cancer antibodies are selected in a group comprising Trastuzumab, Rituximab and Bevacizumab.

In some preferred embodiments of the method, the test sample is a human sample from an individual who has been administered with an anti-cancer antibody selected in a group comprising Trastuzumab, Rituximab and Bevacizumab.

The inventors have shown that a precise quantification of therapeutic antibodies in a human sample, which may be also termed "test sample" herein, may be allowed through the design of a method wherein the amount of therapeutic antibodies, if present in the said sample, is determined by a mass spectrometry analysis making use of two or more labeled forms of said therapeutic antibodies as Internal Standards of a LC-MS/MS quantification method. This is notably illustrated in the examples herein by the quantification of anti-TNF antibodies and of anti-cancer antibodies in human samples, especially in human serum samples.

The inventors have shown herein that the method that they have conceived allows a sensitive, specific and reproducible quantification of therapeutic antibodies in human samples, which encompasses human plasma samples and human serum samples. These advantages of the quantification method described herein are highly noticeable since most of the therapeutic antibodies to be quantified consist of humanized antibodies or "full human" antibodies which share most of their amino acid sequences with the antibodies which are naturally found in the human body fluids, including the antibodies which are found in the human serum or the human plasma. This situation represented a high technical challenge for selecting relevant specific and unique antibody-derived peptides to be monitored by spectrometry, which are not otherwise found naturally in human body fluids, including human serum or human plasma.

Illustratively, Infliximab is a murine-human chimeric anti-TNF antibody and thus contains mostly human amino acid sequences which are found in human antibodies. Infliximab is a genetically engineered chimeric murine/human monoclonal antibody directed against the TNF-alpha antigen. The antibody is an IgG1 kappa immunoglobulin containing murine light- and heavy-chain variable region sequences and human constant region sequences. It means that the amino acid sequences found in the constant regions are common to human IgG, amino acid sequences of the variable regions.

Etanercept is a recombinant dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. The only amino acid sequences that differ from human protein sequences are found in the linker region.

Adalimumab is a human monoclonal antibody against TNF-alpha, produced by recombinant DNA technology using a mammalian cell expression system. Tiny amino acid differences are found in the variable region compared to sequences of human IgG.

Certolizumab pegol is a recombinant Fab' antibody fragment against tumor necrosis factor alpha which is conjugated to an approximately 40 kDa polyethylene glycol. Tiny amino acid differences are found in the variable region of the Fab' compared to sequences of human IgG.

Golimumab is a human IgG1κ monoclonal antibody derived from immunizing genetically engineered mice with human TNFα. Tiny amino acid differences are found in the variable region compared to sequences of human IgG.

Trastuzumab is a humanized monoclonal antibody of the IgG1 isotype directed against the human HER2/Neu receptor.

Rituximab is a murine-human chimeric monoclonal antibody directed against the CD20 receptor and thus contains mostly human amino acid sequences which are found in human antibodies. The antibody is an IgG1 kappa immunoglobulin containing murine light- and heavy-chain variable region sequences and human constant region sequences. It means that the amino acid sequences found in the constant regions are common to human IgG, amino acid sequences of the variable regions.

Bevacizumab is a recombinant humanized monoclonal antibody of the IgG1 isotype directed against human VEGF.

As it is readily understood from the present specification, the quantification method described herein is useful both (i) in situations wherein a tested patient has received a therapeutic treatment by administration of a unique therapeutic antibody and (ii) in situations wherein a tested patient has received, simultaneously or sequentially, more than one therapeutic antibody.

As shown in the examples herein, the inventors have shown that a precise quantification of therapeutic antibodies in a human sample may be performed through the design of a method wherein the amount of therapeutic antibodies, if present in the said sample, is determined by a mass spectrometry method making use of (i) proteolysis peptide(s) derived from two or more therapeutic antibodies contained in the said human sample and (ii) proteolysis peptide(s) derived from a labeled form of the said two or more therapeutic antibodies after:

(A) calculating a ratio between:
  (i) the spectrometry signal generated by one or more selected therapeutic antibody-derived proteolysis peptide from each of two or more therapeutic antibodies and
  (ii) the spectrometry signal generated by one or more selected labeled therapeutic antibody-derived proteolysis peptides from each of the two or more labeled forms of the said two or more anti-TNF antibodies used as an Internal Standard compound(s), and
(B) determining the amount of therapeutic antibodies, if present in the said human sample by reporting the ratio value calculated at step (A) for each of the one or more proteolysis peptide to a calibration curve of ratio values.

The kind of the Internal Standard compound(s) that is (are) used, namely whole labeled therapeutic antibodies, strongly contributes to the accuracy and precision of the therapeutic antibodies quantification method that is described herein as it is explained elsewhere in the present specification.

In some embodiments, the said therapeutic antibodies consist of anti-TNF antibodies, especially anti-TNF antibodies selected in a group comprising Infliximab, Etanercept, Adalimumab, Certolizumab and Golimumab.

In some other embodiments, the said therapeutic antibodies consist of anti-cancer antibodies, especially anti-cancer antibodies selected in a group comprising Trastuzumab, Rituximab and Bevacizumab.

Internal Standard Compounds for Quantifying Therapeutic Antibodies

As shown in the examples herein, (1) the high specificity of the proteolysis peptides derived from these Internal Standard compounds and of the therapeutic antibodies against endogenous human plasmatic proteins, as well as (2) the high physico-chemical homology of (i) the proteolysis peptides derived from these Internal Standard compounds, and of (ii) the proteolysis derived from the therapeutic antibodies, allows a highly precise quantification of the said therapeutic antibodies in a sample.

For performing the therapeutic antibody quantification method described herein, two or more distinct labeled therapeutic antibodies are added to the test sample. Specific labeled proteolysis peptides (also termed "labeled surrogate peptides") are generated at step b), along with the corresponding non-labeled proteolysis peptides (also termed "surrogate peptides" or "non-labeled surrogate peptides") of the corresponding non-labeled therapeutic antibodies to be quantified that were initially present in the said test sample. Then, as it is described in detail further in the present specification, the one or more therapeutic antibodies present in the test sample are quantified by a mass spectrometric method wherein the signals generated by the labeled and non-labeled pairs of surrogate peptides are measured for determining a ratio between the two generated signals (i.e. the signal generated by a specific labeled surrogate peptide and the signal generated by the specific non-labeled surrogate peptide counterpart). Then, the ratio values are used for determining the concentration of the therapeutic antibody(ies) initially contained in the test sample. Most preferably, the said ratio values are used for determining the concentration of the therapeutic antibody(ies) initially contained in the test sample by reporting these ratio values to a calibration curve of ratio values. Accordingly, the said "values" consist of the spectrometry signals generated by the monitored proteolysis peptides.

Then, the ratio value(s) are reported to a calibration curve so as to determine the amount (e.g. the concentration) of one or more therapeutic antibodies in the test sample.

In some embodiments, a calibration curve represents (i) the measured amount of a therapeutic antibody of interest (e.g. in ordinate) against (ii) the expected amount of the said therapeutic antibody (e.g. in abscissa).

In some other embodiments, a calibration curve represents (i) the ratio values between the spectrometry signal area of a therapeutic antibody of interest and the spectrometry signal area of the corresponding labeled therapeutic antibody (Internal Standard compound) (e.g. in ordinate) against (ii) the expected amount of the said therapeutic antibody (e.g. in abscissa).

The higher the number of distinct labeled therapeutic antibodies are added in the test sample at step a) of the method, the higher the number of distinct therapeutic antibodies may be quantified in a test sample by using the anti-TNF antibody quantification method described herein.

In some embodiments of the therapeutic antibodies quantification method of the invention, these one or more labeled therapeutic antibodies correspond to (i) the labeled form(s) of one or more therapeutic antibodies which have been administered to said individual, and/or of (ii) the labeled form(s) of one or more therapeutic antibodies which may be present within said test sample.

In some embodiments, these labeled therapeutic antibodies may consist of one or more therapeutic antibodies comprising one or more signature peptides present within the therapeutic antibodies which (i) have been administered to said individual, and/or which (ii) may be present within said test sample, and which must be quantified.

In some embodiments, these therapeutic antibodies and labeled therapeutic antibodies may consist of one or more humanized IgG antibodies, and fragments thereof.

In some embodiments of the therapeutic antibodies quantification method of the invention, the number of labeled therapeutic antibodies that are used as Internal Standard compounds ranges from two to five distinct labeled antibodies, which encompasses two, three, four and five distinct labeled antibodies.

In some embodiments, these labeled antibodies may consist of anti-TNF antibodies. According to some aspects of these embodiments, the anti-TNF antibodies may be selected in a group comprising labeled Infliximab, labeled Etanercept, labeled Adalimumab, labeled Certolizumab and labeled Golimumab.

In some embodiments of the therapeutic antibodies quantification method of the invention, the labeled anti-TNF antibodies that are used as Internal Standard compounds comprise labeled Infliximab and labeled Etanercept.

In some embodiments of the therapeutic antibodies quantification method of the invention, the labeled anti-TNF antibodies that are used as Internal Standard compounds comprise labeled Infliximab and labeled Adalimumab.

In some embodiments of the therapeutic antibodies quantification method of the invention, the labeled anti-TNF antibodies that are used as Internal Standard compounds comprise labeled Infliximab and labeled Certolizumab.

In some embodiments of the therapeutic antibodies quantification method of the invention, the labeled anti-TNF antibodies that are used as Internal Standard compounds comprise labeled Infliximab and labeled Golimumab.

In some embodiments of the therapeutic antibodies quantification method of the invention, the labeled anti-TNF antibodies that are used as Internal Standard compounds comprise labeled Etanercept and labeled Adalimumab.

In some embodiments of the therapeutic antibodies quantification method of the invention, the labeled anti-TNF antibodies that are used as Internal Standard compounds comprise labeled Etanercept and labeled Certolizumab.

In some embodiments of the therapeutic antibodies quantification method of the invention, the labeled anti-TNF antibodies that are used as Internal Standard compounds comprise labeled Etanercept and labeled Golimumab.

In some embodiments of the therapeutic antibodies quantification method of the invention, the labeled anti-TNF antibodies that are used as Internal Standard compounds comprise labeled Adalimumab and labeled Certolizumab.

In some embodiments of the therapeutic antibodies quantification method of the invention, the labeled anti-TNF antibodies that are used as Internal Standard compounds comprise labeled Adalimumab and labeled Golimumab.

In some embodiments of the therapeutic antibodies quantification method of the invention, the labeled anti-TNF antibodies that are used as Internal Standard compounds comprise labeled Certolizumab and labeled Golimumab.

In some embodiments of the therapeutic antibodies quantification method of the invention, the labeled anti-TNF antibodies that are used as Internal Standard compounds comprise labeled Infliximab, labeled Etanercept and labeled Adalimumab.

In some embodiments of the therapeutic antibodies quantification method of the invention, the labeled anti-TNF antibodies that are used as Internal Standard compounds comprise labeled Infliximab, labeled Etanercept and labeled Certolizumab.

In some embodiments of the therapeutic antibodies quantification method of the invention, the labeled anti-TNF antibodies that are used as Internal Standard compounds comprise labeled Infliximab, labeled Etanercept and labeled Golimumab.

In some embodiments of the therapeutic antibodies quantification method of the invention, the labeled anti-TNF antibodies that are used as Internal Standard compounds comprise labeled Etanercept, labeled Adalimumab and labeled Certolizumab.

In some embodiments of the therapeutic antibodies quantification method of the invention, the labeled anti-TNF antibodies that are used as Internal Standard compounds comprise labeled Etanercept, labeled Adalimumab and labeled Golimumab.

In some embodiments of the therapeutic antibodies quantification method of the invention, the labeled anti-TNF antibodies that are used as Internal Standard compounds comprise labeled Certolizumab, labeled Adalimumab and labeled Golimumab.

In some embodiments of the therapeutic antibodies quantification method of the invention, the labeled anti-TNF antibodies that are used as Internal Standard compounds comprise labeled Adalimumab, labeled Infliximab and labeled Certolizumab.

In some embodiments of the therapeutic antibodies quantification method of the invention, the labeled anti-TNF antibodies that are used as Internal Standard compounds comprise labeled Adalimumab, labeled Infliximab and labeled Golimumab.

In some embodiments of the therapeutic antibodies quantification method of the invention, the labeled anti-TNF antibodies that are used as Internal Standard compounds comprise labeled Certolizumab, labeled Infliximab and labeled Adalimumab.

In some embodiments of the therapeutic antibodies quantification method of the invention, the labeled anti-TNF antibodies that are used as Internal Standard compounds comprise labeled Certolizumab, labeled Infliximab and labeled Golimumab.

In some embodiments of the therapeutic antibodies quantification method of the invention, the labeled anti-TNF antibodies that are used as Internal Standard compounds comprise labeled Infliximab, labeled Etanercept, labeled Adalimumab and labeled Certolizumab.

In some embodiments of the therapeutic antibodies quantification method of the invention, the labeled anti-TNF antibodies that are used as Internal Standard compounds comprise labeled Infliximab, labeled Etanercept, labeled Adalimumab and labeled Golimumab.

In some embodiments of the therapeutic antibodies quantification method of the invention, the labeled anti-TNF antibodies that are used as Internal Standard compounds comprise labeled Infliximab, labeled Adalimumab, labeled Certolizumab and labeled Golimumab.

In some embodiments of the therapeutic antibodies quantification method of the invention, the labeled anti-TNF antibodies that are used as Internal Standard compounds comprise labeled Infliximab, labeled Etanercept, labeled Certolizumab and labeled Golimumab.

In some embodiments of the therapeutic antibodies quantification method of the invention, the labeled anti-TNF antibodies that are used as Internal Standard compounds comprise labeled Etanercept, labeled Adalimumab, labeled Certolizumab and labeled Golimumab.

In some embodiments of the therapeutic antibodies quantification method of the invention, the labeled anti-TNF antibodies that are used as Internal Standard compounds comprise labeled Infliximab, labeled Etanercept, labeled Adalimumab, labeled Certolizumab and labeled Golimumab.

In some embodiments, these labeled antibodies may consist of anti-cancer antibodies. According to some aspects of these embodiments, the anti-cancer antibodies may be selected in a group comprising Trastuzumab, Rituximab and Bevacizumab.

In some embodiments of the therapeutic antibodies quantification method of the invention, the labeled anti-cancer antibodies that are used as Internal Standard compounds comprise labeled Trastuzumab and labeled Rituximab.

In some embodiments of the therapeutic antibodies quantification method of the invention, the labeled anti-cancer antibodies that are used as Internal Standard compounds comprise labeled Trastuzumab and labeled Bevacizumab.

In some embodiments of the therapeutic antibodies quantification method of the invention, the labeled anti-cancer antibodies that are used as Internal Standard compounds comprise labeled Rituximab and labeled Bevacizumab.

In some embodiments of the therapeutic antibodies quantification method of the invention, the labeled anti-cancer antibodies that are used as Internal Standard compounds comprise labeled labeled Trastuzumab, labeled Rituximab and labeled Bevacizumab.

As used herein, a "labeled" therapeutic antibody, also referred herein as the "labelled form of therapeutic antibodies, consists of an antibody having the same amino acid sequence as a therapeutic antibody or a combination of antibodies to be quantified, and which has been obtained by a method according to which one or more labeled amino acids have been incorporated in the polypeptide chain(s). Methods for labeling the therapeutic antibodies (including anti-TNF and/or anti-cancer antibodies) that are used as Internal Standard compounds in the therapeutic antibody quantification method described herein are disclosed elsewhere in the present specification.

Thus, used herein, a "labeled" anti-TNF antibody selected in a group comprising labeled Infliximab, labeled Etanercept, labeled Adalimumab, labeled Certolizumab and labeled Golimumab does not mean that the therapeutic antibodies Infliximab, Etanercept, Adalimumab, Certolizumab or Golimumab have been labeled. Rather, a "labeled" anti-TNF antibody consists of an antibody having the same amino acid sequence than a therapeutic anti-TNF antibody selected in a group comprising Infliximab, Etanercept, Adalimumab, Certolizumab and Golimumab and that has been obtained by a method according to which one or more labeled amino acids have been incorporated in the polypeptide chain(s). Methods for labeling the anti-TNF antibodies that are used as Internal Standard compounds in the therapeutic antibody quantification method described herein are disclosed elsewhere in the present specification.

Also, a "labeled" anti-cancer antibody selected in a group comprising labeled Trastuzumab, labeled Rituximab and labeled Bevacizumab does not mean that the therapeutic antibodies Trastuzumab, Rituximab or Bevacizumab have been labeled. Rather, a "labeled" anti-cancer antibody consists of an antibody having the same amino acid sequence than a therapeutic anti-cancer antibody selected in a group comprising Trastuzumab, Rituximab and Bevacizumab and that has been obtained by a method according to which one or more labeled amino acids have been incorporated in the polypeptide chain(s). Methods for labeling the anti-cancer antibodies that are used as Internal Standard compounds in the therapeutic antibody quantification method described herein are disclosed elsewhere in the present specification.

Selecting Proteolysis Peptides Derived from a Therapeutic Antibody

Proteolysis peptides derived from a therapeutic antibody to be monitored by mass spectrometry when performing the therapeutic antibody quantification method described herein may be selected according to selection methods that are known from the one skilled in the art.

According to the present antibody quantification method which is performed by starting with a human sample, and especially a human plasma sample or a human plasma sample, the proteolysis peptides shall be selected so as (i) to be discriminant as regards proteolysis peptides susceptible to be generated by subjecting human endogenous proteins to the action of a protease, e;g. trypsin or IdeS, and (ii) to be discriminant as regards proteolysis peptides susceptible to be generated by the action of a protease, e.g. trypsin or IdeS, on other exogenous therapeutic antibodies that are susceptible to be present in the said human sample, e.g. the said human plasma sample or the said human serum sample.

The surrogate peptide approach relies on the analysis of the surrogate peptide for the quantitation of the whole target protein. Therefore, the selection of appropriate surrogate peptide is critical to ensure the sensitivity, specificity and robustness of the assay. Usually, 'signature' peptides, which are peptides unique for the specific target protein, are chosen as the surrogate peptides. Selection of the appropriate surrogate peptides should: (1) avoid peptides prone to chemical modification (e.g., peptides containing methionine, cysteine or tryptophan); (2) avoid arginine-arginine and lysine-lysine in the peptide sequence to minimize inconsistent tryptic digestion; and (3) select peptides with appropriate length (~8-20 amino acids): being too short may cause the lack of selectivity, and too long may affect the sensitivity (Wu et al., Rapid Commun Mass Spectrom. 2011; Vol. 25:281-90).

A typical procedure is to perform an in silico digestion of the given therapeutic antibody to generate a set of potential surrogate peptides. These peptides are then searched against all existing proteins in the biological matrices using online databases (e.g., Standard Protein BLAST) to confirm that the signature peptides only exist in the target protein. The sensitivity, specificity and chromatographic behavior of these signature peptides are then evaluated using actual digested protein samples in biological matrices, and the best one(s) will be chosen as the surrogate peptide(s) for the said given therapeutic antibody.

The proteolysis peptides are selected based on online in silico prediction tools (Kamiie et al., Pharmaceutical Research, vol. 25(6): 1469-1483, 2008). All potential tryptic peptides were screened by alignment against the human proteome.

As used herein, proteolysis peptides, which may also be termed surrogate peptides herein, are selected on the basis on their uniqueness among the peptides that may be present after subjecting human plasma or human serum to a protease. Accordingly, each selected proteolysis peptide consists of a unique signature of the presence of a given therapeutic antibody in a sample.

For a given therapeutic antibody to be quantified with the quantification method described herein, the selection of one or more proteolysis peptide(s) (i.e. "surrogate peptide(s)") may be performed by comparing (i) a set of the expected proteolysis peptides derived from the said given therapeutic antibody with (ii) a set of the proteolysis peptides that are expected to be derived from the same proteolysis of human plasma or human serum proteins, and especially a set of the proteolysis peptides that are expected to be derived from the same proteolysis of therapeutic antibodies.

In some embodiments, the set of expected proteolysis peptides may be obtained in silico by using using the query peptide mass on the online bioinformatics tool www.expasy.ch after entering on the tool (i) the sequence of the said given therapeutic antibody and (ii) the sequences of the proteins that are expected to be contained in human plasma or human serum, and especially the sequences of therapeutic antibodies, such as human IgG. Then, peptides found exclusively in the set of proteolysis peptides derived from the said given therapeutic antibody and which are thus not found in the set of proteolysis peptides derived from the proteins that are expected to be contained in human plasma or human serum, such as human IgG, are selected.

The selection of proteolysis peptides (surrogate peptides) derived from the said given therapeutic antibody may also be performed in silico, by performing a similarity research by sequence alignment against a human protein database such as the UniProtKB_HUMAN database, and by using a relevant bioinformatics software, e.g. the bioinformatics tool termed BLAST 2.0 (Basic Local Alignment Search Tool). Selection of the one or more proteolysis peptide(s) derived from the said given therapeutic antibody for LC-MS/MS quantification shall generally take into account of the score resulting from the BLAST which calculates the statistical significance of matches.

Among set of one or more potential proteolytic peptides pre-selected as described above, those potential proteolytic peptides with missed cleavage sites by the protease are excluded. Missed cleavage sites may be predicted by using the software called MC:pred (Lawless et al., OMICS, September 2012, Vol. 16(9).

Then, in some embodiments, the uniqueness of each of the selected proteolysis peptides is most preferably confirmed experimentally, e.g. against a subset of the UniProt SwissProt *Homo sapiens* database incremented by the sequence of the said given therapeutic antibody.

In still further embodiments, the uniqueness of each of the selected proteolysis peptides is most preferably further experimentally confirmed by analysing a sample containing a collection of human (i.e. IgG) polyvalent therapeutic solution in the same way to ensure that signature peptides of the said given therapeutic antibody are absent of human (i.e.) IgG polyvalent protease digest.

Specific Embodiments of Selected Proteolysis Peptides

For performing the therapeutic antibody quantification method of the invention wherein the proteolysis step b) makes use of trypsin as the sole protease or of trypsin as a protease contained in a protease mixture, the one or more selected proteolysis peptides are selected in a group comprising:

-for Infliximab:

LEESGGGLVQPGGSMK, (SEQ ID NO. 1)

GLEWVAEIR, (SEQ ID NO. 2)

SINSATHYAESVK, (SEQ ID NO. 3)

SAVYLQMTDLR, (SEQ ID NO. 4)

TEDTGVYYCSR, (SEQ ID NO. 5)

DILLTQSPAILSVSPGER, (SEQ ID NO. 6)

ASQFVGSSIHWYQQR, (SEQ ID NO. 7)

YASESMSGIPSR, (SEQ ID NO. 8)

-for Etanercept:

LPAQVAFTPYAPEPGSTCR, (SEQ ID NO. 9)

EYYDQTAQMCCSK, (SEQ ID NO. 10)

CSSDQVETQACTR, (SEQ ID NO. 11)

ICTCRPGWYCALSK, (SEQ ID NO. 12)

LCAPLR, (SEQ ID NO. 13)

SMAPGAVHLPQPVSTR, (SEQ ID NO. 14)

SQHTQPTPEPSTAPSTSFLLPMGPSPPAEGSTGDEPK, (SEQ ID NO. 15)

-for Adalimumab:

GLEWVSAITWNSGHIDYADSVEGR, (SEQ ID NO. 16)

VSYLSTASSLDYWGQGTLVTVSSASTK, (SEQ ID NO. 17)

QAPGKGLEWVSAITWNSGHIDYADSVEGR, (SEQ ID NO. 18)

ASQGIR, (SEQ ID NO. 19)

NYLAWYQQKPGK, (SEQ ID NO. 20)

LLIYAASTLQSGVPSR, (SEQ ID NO. 21)

FSGSGSGTDFTLTISSLQPEDVATYYCQR, (SEQ ID NO. 22)

APYTFGQGTK, (SEQ ID NO. 23)

-for Certolizumab:

LSCAASGYVFTDYGMNWVR, (SEQ ID NO. 24)

GLEWMGWINTYIGEPIYADSVK, (SEQ ID NO. 25)

FTFSLDTSK, (SEQ ID NO. 26)

STAYLQMNSLR, (SEQ ID NO. 27)

ASQNVGTNVAWYQQKPGK, (SEQ ID NO. 28)

ALIYSASFLYSGVPYR (SEQ ID NO. 29)

FSGSGSGTDFTLTISSLQPEDFATYYCQQYNIYPLTFGQGTK, (SEQ ID NO. 30)

-for Golimumab:

LSCAASGFIFSSYAMHWVR, (SEQ ID NO. 31)

QAPGNGLEWVAFMSYDGSNK, (SEQ ID NO. 32)

GIAAGGNYYYYGMDVISSQGTTVTVSSASTK, (SEQ ID NO. 33)

ASQSVYSYLAWYQQK, (SEQ ID NO. 34)

LLIYDASNR, (SEQ ID NO. 35)

FSGSGSGTDFTLTISSLEPEDFAVYYCQQR, (SEQ ID NO. 36)

SNWPPFTFGPGTK, (SEQ NO. 37)

-for Trastuzumab:

LSCAASGFNIK (SEQ ID NO. 47)

DTYIHWVR (SEQ ID NO. 48)

IYPTNGYTR (SEQ ID NO. 49)

FTISADTSK (SEQ ID NO. 50)

ASQDVNTAVAWYQQKPGK (SEQ ID NO. 51)

LLIYSASFLYSGVPSR (SEQ ID NO. 52)

SGTDFTLTISSLQPEDFATYYCQQHYTTPPTFGQGTK (SEQ ID NO. 53)

-for Rituximab:

QVQLQQPGAELVKPGASVK (SEQ ID NO. 54)

ASGYTFTSYNMHWVK (SEQ ID NO. 55)

GLEWIGAIYPGNGDTSYNQK (SEQ ID NO. 56)

ATLTADK (SEQ ID NO. 57)

SSSTAYMQLSSLTSEDSAVYYCAR (SEQ ID NO. 58)

STYYGGDWYFNVWGAGTTVTVSAASTK (SEQ ID NO. 59)

QIVLSQSPAILSASPGEK (SEQ ID NO. 60)

VTMTCR (SEQ ID NO. 61)

ASSSVSYIHWFQQKPGSSPKPWIYATSNLASGVPVR (SEQ ID NO. 62)

FSGSGSGTSYSLTISR (SEQ ID NO 63)

VEAEDAATYYCQQWTSNPPTFGGGTK (SEQ ID NO. 64)

-for Bevacizumab:

LSCAASGYTFTNYGMNWVR (SEQ ID NO. 65)

GLEWVGWINTYTGEPTYAADFK (SEQ ID NO. 66)

FTFSLDTSK (SEQ ID NO. 67)

STAYLQMNSLR (SEQ ID NO. 68)

YPHYYGSSHWYFDVWGQGTLVTVSSASTK (SEQ ID NO. 69)

VTITCSASQDISNYLNWYQQKPGK (SEQ ID NO. 70)

VLIYFTSSLHSGVPSR (SEQ ID NO. 71)

FSGSGSGTDFTLTISSLQPEDFATYYCQQYSTVPWTFGQGTK (SEQ ID NO. 72)

For performing the anti-TNF antibodies quantification method of the invention wherein the proteolysis step b) makes use of a hinge-targeting protease, the one or more selected proteolysis peptides are selected in a group comprising:

-for Infliximab:

EVKLEESGGGLVQPGGSMKLSCVASGFIFSNHWMNWVRQSPEKGLEWVAE IRSKSINSATHYAESVKGRFTISRDDSKSAVYLQMTDLRTEDTGVYYCSR NYYGSTYDYWGQGTTLTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLG [VH + CH1], (SEQ ID NO. 38)
and DILLTQSPAILSVSPGERVSFSCRASQFVGSSIHWYQQRTNGSPRLLIKY ASESMSGIPSRFSGSGSGTDFTLSINTVESEDIADYYCQQSHSWPFTFGS GTNLEVKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC [VL + CL], (SEQ ID NO. 39)

-for Etanercept:

(SEQ ID NO. 40)
LPAQVAFTPYAPEPGSTCRLREYYDQTAQMCCSKCSPGQHAKVFCTKTSD
TVCDSCEDSTYTQLWNWVPECLSCGSRCSSDQVETQACTREQNRICTCRP
GWYCALSKQEGCRLCAPLRKCRPGFGVARPGTETSDVVCKPCAPGTFSNT
TSSTDICRPHQICNVVAIPGNASMDAVCTSTSPTRSMAPGAVHLPQPVST
RSQHTQPTPEPSTAPSTSFLLPMGPSPPAEGSTGDEPKSCDKTHTCPPCP
APELLG [Fraction P75 du récepteur soluble du TNF
alpha], -for Adalimumab:

(SEQ ID NO. 41)
EVQLVESGGGLVQPGRSLRLSCAASGFTFDDYAMHWVRQAPGKGLEWVSA
ITWNSGHIDYADSVEGRFTISRDNAKNSLYLQMNSLRAEDTAVYYCAKVS
YLSTASSLDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHTCPPCPAPELLG [VH +
CH1], (SEQ ID NO. 42)
DIQMTQSPSSLSASVGDRVTITCRASQGIRNYLAWYQQKPGKAPKLLIYA
ASTLQSGVPSRFSGSGSGTDFTLTISSLQPEDVATYYCQRYNRAPYTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC [VL + CL]

-for Certolizumab:

(SEQ ID NO. 43)
EVQLVESGGGLVQPGGSLRLSCAASGYVFTDYGMNWVRQAPGKGLEWMGW
INTYIGEPIYADSVKGRFTFSLDTSKSTAYLQMNSLRAEDTAVYYCARGY
RSYAMDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCAA [VH + CH1], (SEQ ID NO. 44)
DIQMTQSPSSLSASVGDRVTITCKASQNVGTNVAWYQQKPGKAPKALIYS
ASFLYSGVPYRFSGSGSGTDFTLTISSLQPEDFATYYCQQYNIYPLTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC [VL + CL],

-for Golimumab:

(SEQ ID NO. 45)
QVQLVESGGGVVQPGRSLRLSCAASGFIFSSYAMHWVRQAPGNGLEWVAF
MSYDGSNKKYADSVKGRFTISRDNSKNTLYLQMNSLRAEDTAVYYCARDR
GIAAGGNYYYYGMDVISSQGTTVTVSSASTKGPSVFPLAPSSKSTSGGTA
ALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLG
[VH + CH1], (SEQ ID NO. 46)
EIVLTQSPATLSLSPGERATLSCRASQSVYSYLAWYQQKPGQAPRLLIYD
ASNRATGIPARFSGSGSGTDFTLTISSLEPEDFAVYYCQQRSNWPPFTFG
PGTKVDIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC [VL + CL]

The above-mentioned selection of proteolysis peptides consists of 73 distinct peptides, which may be considered individually and as a combination of two or more selected proteolysis peptides, for performing antibodies quantification methods of the invention.

Accordingly, when the above-mentioned selection of labelled therapeutic antibodies, and proteolysed peptides thereof, is considered as a combination of two or more peptides, such combination may include:
one or more proteolysed peptides derived from a same antibody; and/or
one or more proteolysed peptides derived from a plurality of antibodies.

Accordingly, the therapeutic antibodies that are used as Internal Standard compounds, may be suitable for generating two or more selected proteolysis peptides comprising or consisting of SEQ ID No 1 to 72, including any combinations thereof.

Accordingly, the two or more selected proteolysis peptides which are explicitly considered by the invention, include any combination of two selected proteolysis peptides comprising or consisting of SEQ ID No 1 to 72, and which are marked herebelow (Table 1) by a "X" sign:

|     | 1 | 2 | 3 | 4 | 5 | 6 | 7 | 8 | 9 | 10 | 11 | 12 | 13 | 14 | 15 | 16 | 17 | 18 | (...) | 72 |
|-----|---|---|---|---|---|---|---|---|---|----|----|----|----|----|----|----|----|----|-------|----|
| 1'  |   | X | X | X | X | X | X | X | X | X  | X  | X  | X  | X  | X  | X  | X  | X  |       | X  |
| 2'  | X |   | X | X | X | X | X | X | X | X  | X  | X  | X  | X  | X  | X  | X  | X  |       | X  |
| 3'  | X | X |   | X | X | X | X | X | X | X  | X  | X  | X  | X  | X  | X  | X  | X  |       | X  |
| 4'  | X | X | X |   | X | X | X | X | X | X  | X  | X  | X  | X  | X  | X  | X  | X  |       | X  |
| 5'  | X | X | X | X |   | X | X | X | X | X  | X  | X  | X  | X  | X  | X  | X  | X  |       | X  |
| 6'  | X | X | X | X | X |   | X | X | X | X  | X  | X  | X  | X  | X  | X  | X  | X  |       | X  |
| 7'  | X | X | X | X | X | X |   | X | X | X  | X  | X  | X  | X  | X  | X  | X  | X  |       | X  |
| 8'  | X | X | X | X | X | X | X |   | X | X  | X  | X  | X  | X  | X  | X  | X  | X  |       | X  |
| 9'  | X | X | X | X | X | X | X | X |   | X  | X  | X  | X  | X  | X  | X  | X  | X  |       | X  |
| 10' | X | X | X | X | X | X | X | X | X |    | X  | X  | X  | X  | X  | X  | X  | X  |       | X  |
| 11' | X | X | X | X | X | X | X | X | X | X  |    | X  | X  | X  | X  | X  | X  | X  |       | X  |
| 12' | X | X | X | X | X | X | X | X | X | X  | X  |    | X  | X  | X  | X  | X  | X  |       | X  |
| 13' | X | X | X | X | X | X | X | X | X | X  | X  | X  |    | X  | X  | X  | X  | X  |       | X  |
| 14' | X | X | X | X | X | X | X | X | X | X  | X  | X  | X  |    | X  | X  | X  | X  |       | X  |
| 15' | X | X | X | X | X | X | X | X | X | X  | X  | X  | X  | X  |    | X  | X  | X  |       | X  |
| 16' | X | X | X | X | X | X | X | X | X | X  | X  | X  | X  | X  | X  |    | X  | X  |       | X  |
| 17' | X | X | X | X | X | X | X | X | X | X  | X  | X  | X  | X  | X  | X  |    | X  |       | X  |

-continued

| | 1 | 2 | 3 | 4 | 5 | 6 | 7 | 8 | 9 | 10 | 11 | 12 | 13 | 14 | 15 | 16 | 17 | 18 | (...) | 72 |
|---|---|---|---|---|---|---|---|---|---|---|---|---|---|---|---|---|---|---|---|---|
| 18' | X | X | X | X | X | X | X | X | X | X | X | X | X | X | X | X |   | X | X | X |
| 19' | X | X | X | X | X | X | X | X | X | X | X | X | X | X | X | X | X |   | X | X |
| 20' | X | X | X | X | X | X | X | X | X | X | X | X | X | X | X | X | X | X | X | X |
| 21' | X | X | X | X | X | X | X | X | X | X | X | X | X | X | X | X | X | X | X | X |
| 22' | X | X | X | X | X | X | X | X | X | X | X | X | X | X | X | X | X | X | X | X |
| 23' | X | X | X | X | X | X | X | X | X | X | X | X | X | X | X | X | X | X | X | X |
| 24' | X | X | X | X | X | X | X | X | X | X | X | X | X | X | X | X | X | X | X | X |
| 25' | X | X | X | X | X | X | X | X | X | X | X | X | X | X | X | X | X | X | X | X |
| 26' | X | X | X | X | X | X | X | X | X | X | X | X | X | X | X | X | X | X | X | X |
| 27' | X | X | X | X | X | X | X | X | X | X | X | X | X | X | X | X | X | X | X | X |
| 28' | X | X | X | X | X | X | X | X | X | X | X | X | X | X | X | X | X | X | X | X |
| 29' | X | X | X | X | X | X | X | X | X | X | X | X | X | X | X | X | X | X | X | X |
| 30' | X | X | X | X | X | X | X | X | X | X | X | X | X | X | X | X | X | X | X | X |
| 31' | X | X | X | X | X | X | X | X | X | X | X | X | X | X | X | X | X | X | X | X |
| 32' | X | X | X | X | X | X | X | X | X | X | X | X | X | X | X | X | X | X | X | X |
| 33' | X | X | X | X | X | X | X | X | X | X | X | X | X | X | X | X | X | X | X | X |
| 34' | X | X | X | X | X | X | X | X | X | X | X | X | X | X | X | X | X | X | X | X |
| 35' | X | X | X | X | X | X | X | X | X | X | X | X | X | X | X | X | X | X | X | X |
| 36' | X | X | X | X | X | X | X | X | X | X | X | X | X | X | X | X | X | X | X | X |
| 37' | X | X | X | X | X | X | X | X | X | X | X | X | X | X | X | X | X | X | X | X |
| 38' | X | X | X | X | X | X | X | X | X | X | X | X | X | X | X | X | X | X | X | X |
| 39' | X | X | X | X | X | X | X | X | X | X | X | X | X | X | X | X | X | X | X | X |
| 40' | X | X | X | X | X | X | X | X | X | X | X | X | X | X | X | X | X | X | X | X |
| 41' | X | X | X | X | X | X | X | X | X | X | X | X | X | X | X | X | X | X | X | X |
| 42' | X | X | X | X | X | X | X | X | X | X | X | X | X | X | X | X | X | X | X | X |
| 43' | X | X | X | X | X | X | X | X | X | X | X | X | X | X | X | X | X | X | X | X |
| 44' | X | X | X | X | X | X | X | X | X | X | X | X | X | X | X | X | X | X | X | X |
| 45' | X | X | X | X | X | X | X | X | X | X | X | X | X | X | X | X | X | X | X | X |
| 46' | X | X | X | X | X | X | X | X | X | X | X | X | X | X | X | X | X | X | X | X |
| 47' | X | X | X | X | X | X | X | X | X | X | X | X | X | X | X | X | X | X | X | X |
| 48' | X | X | X | X | X | X | X | X | X | X | X | X | X | X | X | X | X | X | X | X |
| 49' | X | X | X | X | X | X | X | X | X | X | X | X | X | X | X | X | X | X | X | X |
| 50' | X | X | X | X | X | X | X | X | X | X | X | X | X | X | X | X | X | X | X | X |
| 51' | X | X | X | X | X | X | X | X | X | X | X | X | X | X | X | X | X | X | X | X |
| 52' | X | X | X | X | X | X | X | X | X | X | X | X | X | X | X | X | X | X | X | X |
| 53' | X | X | X | X | X | X | X | X | X | X | X | X | X | X | X | X | X | X | X | X |
| 54' | X | X | X | X | X | X | X | X | X | X | X | X | X | X | X | X | X | X | X | X |
| 55' | X | X | X | X | X | X | X | X | X | X | X | X | X | X | X | X | X | X | X | X |
| 56' | X | X | X | X | X | X | X | X | X | X | X | X | X | X | X | X | X | X | X | X |
| 57' | X | X | X | X | X | X | X | X | X | X | X | X | X | X | X | X | X | X | X | X |
| 58' | X | X | X | X | X | X | X | X | X | X | X | X | X | X | X | X | X | X | X | X |
| 59' | X | X | X | X | X | X | X | X | X | X | X | X | X | X | X | X | X | X | X | X |
| 60' | X | X | X | X | X | X | X | X | X | X | X | X | X | X | X | X | X | X | X | X |
| 61' | X | X | X | X | X | X | X | X | X | X | X | X | X | X | X | X | X | X | X | X |
| 62' | X | X | X | X | X | X | X | X | X | X | X | X | X | X | X | X | X | X | X | X |
| 63' | X | X | X | X | X | X | X | X | X | X | X | X | X | X | X | X | X | X | X | X |
| 64' | X | X | X | X | X | X | X | X | X | X | X | X | X | X | X | X | X | X | X | X |
| 65' | X | X | X | X | X | X | X | X | X | X | X | X | X | X | X | X | X | X | X | X |
| 66' | X | X | X | X | X | X | X | X | X | X | X | X | X | X | X | X | X | X | X | X |
| 67' | X | X | X | X | X | X | X | X | X | X | X | X | X | X | X | X | X | X | X | X |
| 68' | X | X | X | X | X | X | X | X | X | X | X | X | X | X | X | X | X | X | X | X |
| 69' | X | X | X | X | X | X | X | X | X | X | X | X | X | X | X | X | X | X | X | X |
| 70' | X | X | X | X | X | X | X | X | X | X | X | X | X | X | X | X | X | X | X | X |
| 71' | X | X | X | X | X | X | X | X | X | X | X | X | X | X | X | X | X | X | X | X |
| 72' | X | X | X | X | X | X | X | X | X | X | X | X | X | X | X | X | X | X | X | X | wherein " ' " in the y-axis marks one or more selected proteolysis peptides including at least one selected proteolysis peptide corresponding to SEQ ID No from 1 to 72;

wherein ( ... ) corresponds to any SEQ ID No Y with Y being an integer selected from 18 to 71, which includes 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 and 71;

wherein "X" marks a combination of the two selected proteolysis peptides selected from the corresponding SEQ IDs selected from SEQ ID 1 to 72

Accordingly, any combination thereof is expressly disclosed in the sense of the invention: when Z selected proteolysis peptides are monitored (i.e. as Stable Isotope Labelled peptides), these may be selected, in an iterative manner, from any one of the combinations of two which are described above. Accordingly, a mixture comprising (Z-1) selected proteolysis peptides including at least one selected proteolysis peptide of SEQ ID as defined in the y-axis is then combined with one additional selected proteolysis peptides as defined in the x-axis, thereby providing the Z selected proteolysis peptides to be monitored.

Accordingly, the Z (two or more) selected proteolysis peptides may encompass more than two, which includes more than two, three, four, five, six, seven, eight, nine, ten and more than ten selected proteolysis peptides.

The therapeutic antibodies that are used as Internal Standard compounds are labelled with one or more stable isotopes. Stable isotopes may be selected in a group comprising $^{2}H$, $^{13}C$, $^{15}N$ and $^{18}O$. Preferably, stable isotopes are selected in a group comprising $^{13}C$ and $^{15}N$.

In some embodiments, isotopic labeling is only restricted to specific amino acids, which are preferably Arginine, Lysine and/or Leucine.

A Stable Isotope Labelled (SIL) peptide generated by proteolysis of a labeled therapeutic antibody (SIL therapeutic antibody) used as an Internal Standard compound, due to a sufficient mass increment relative to the same but unlabeled peptide (i.e. an unlabeled peptide generated by proteolysis of the corresponding unlabeled therapeutic antibody initially present in the test sample), is thus discriminated from the said unlabeled proteolysis peptide by mass spectrometry analysis.

Illustratively, a Stable Isotope Labelled peptide selected in a group comprising the surrogate peptides of SEQ ID NO 1-8 (for Infliximab), SEQ ID NO. 9-15 (for Etanercept), SEQ ID NO. 16-23 (for Adalimumab), SEQ ID NO. 24-30 (for Certolizumab), SEQ ID NO. 31-37 (for Golimumab), SEQ ID NO. 47-53 (for Trastuzumab), SEQ ID NO. 54-64 (for Rituximab) or SEQ ID NO. 65-72 (for Bevacizumab) is discriminated by mass spectrometry analysis, from the non-labelled surrogate peptides of the same respective amino acid sequences that are generated upon trypsin treatment of Infliximab, Etanercept, Adalimumab, Certolizumab, Golimumab, Trastuzumab, Rituximab or Bevacizumab respectively.

Also, a Stable Isotope Labelled peptide selected in a group comprising the surrogate peptides of SEQ ID NO 38-39 (for Infliximab), 40 (for Etanercept), 41-42 (for Adalimumab), 43-44 (for Certolizumab) or 45-46 (for Golimumab) is discriminated by mass spectrometry analysis, from the non-labelled surrogate peptides of the same respective amino acid sequences that are generated upon IdeS treatment of Infliximab, Etanercept, Adalimumab, Certolizumab or Golimumab, respectively.

Stable Isotope Labelled (SIL) anti-TNF antibodies are, notably, commercially available.

Illustratively, the SIL peptides may be obtained from JPT Peptide Technologies GmbH (Berlin, Germany) or from Sigma-Aldrich (Saint Quentin Fallavier, France) under the name Aqua™ peptides.

In particular, Stable Isotope Labelled (SIL) therapeutic antibodies are available from the French Company Promise Advanced Proteomics (Grenoble, France).

Generating a Calibration Curve

The precise quantification of therapeutic antibodies by mass spectrometric analysis is allowed by the use of at least an Internal Standard compound for each therapeutic antibody of interest, the presence of which in combination with the said antibody of interest in a human sample permits the calculation of ratio values between (i) the spectrometry signal generated by a selected proteolysis surrogate peptide derived from a specific therapeutic antibody and (ii) the spectrometry signal generated by a corresponding selected labeled surrogate peptide generated by enzyme proteolysis treatment of a labeled form of the said therapeutic antibody.

As it will be further detailed in the present specification, the quantification of therapeutic antibodies is performed by reporting the ratio value calculated for each proteolysis peptide considered in the human sample tested, or test sample, to a calibration curve of ratio values generated, for each therapeutic antibody of interest, with known amounts of the said therapeutic antibody of interest and fixed and known amounts of a labeled form of the said therapeutique antibody that is used as an Internal Standard compound.

For generating a calibration curve, a serial or set of calibration samples (CS) are prepared, wherein:

each calibration sample contains a known amount of the selected therapeutic antibody, most preferably a known amount of an anti-TNF antibody selected in a group comprising Infliximab, Etanercept, Adalimumab, Certolizumab and Golimumab or most preferably a known amount of an anti-cancer antibody selected in a group comprising Trastuzumab, Rituximab and Bevacizumab, each calibration sample contains a fixed and known amount of a labeled form of the said therapeutic antibody used as an Internal Standard compound, most preferably a fixed and known amount of a labeled form of the said selected therapeutic antibody used as an Internal Standard Compound selected in a group comprising Infliximab, Etanercept, Adalimumab, Certolizumab and Golimumab, or most preferably a fixed and known amount of a labeled form of the said selected therapeutic antibody used as an Internal Standard Compound selected in a group comprising Trastuzumab, Rituximab and Bevacizumab, and the serial or set of calibration samples are prepared so as to cover an amount range of the therapeutic antibodies encompassing at least the amount range of the therapeutic antibody(ies) which is(are) expected to be contained in a test sample.

For the sake of clarity, each calibration sample comprises the same fixed and known amount of the selected Internal Standard compound.

Illustratively, the amount range of the selected therapeutic antibody which is covered by the serial or set of calibration samples, when expressed as a final concentration in the calibration samples, may range from 0.1 µg/mL to 100 µg/mL. For example, a serial or set of calibration samples may comprise eight calibration samples comprising a therapeutic antibody of interest at respective final concentrations of 0.1 µg/mL, 0.5 µg/mL, 1 µg/mL, 5 µg/mL, 10 µg/mL, 20 µg/mL, 25 µg/mL, 50 µg/mL, 75 µg/mL and 100 µg/mL.

Thus, according to the therapeutic antibody quantification method described herein, a calibration curve may be generated for each of the therapeutic antibody of interest. In some embodiments, a calibration curve may be generated for each anti-TNF antibody of interest, especially for each anti-TNF antibody of interest selected in a group comprising Infliximab, Etanercept, Adalimumab, Certolizumab and Golimumab. In some embodiments, a calibration curve may be generated for each anti-cancer antibody of interest, especially for each anti-cancer antibody of interest selected in a group comprising Trastuzumab, Rituximab and Bevacizumab.

In other embodiments, a calibration curve may be generated simultaneously for a plurality of therapeutic antibodies, especially for a plurality of anti-TNF antibodies selected in a group comprising Infliximab, Etanercept, Adalimumab, Certolizumab and Golimumab, or especially for a plurality of anti-cancer antibodies selected in a group comprising Trastuzumab, Rituximab and Bevacizumab. According to these embodiments, a serial of calibration samples, each calibration sample containing (i) a plurality of non-labeled therapeutic antibodies, especially for a plurality of anti-TNF antibodies selected in a group comprising Infliximab, Etanercept, Adalimumab, Certolizumab and Golimumab, or especially for a plurality of anti-cancer antibodies selected in a group comprising Trastuzumab, Rituximab and Bevacizumab, each therapeutic antibody being at a given concentration, and (ii) the corresponding labeled form (most preferably SIL antibodies) of each of the said therapeutic antibody at a fixed concentration, and wherein, the serial of calibration samples covers a range of concentrations (e.g. 0;1 µg/mL to 100 µg/mL) of the said non-labeled therapeutic antibodies, and wherein the same fixed concentration of the corresponding labeled therapeutic antibodies is present in each of the calibration sample (e.g. a fixed concentration of 20 µg/mL of each of the labeled therapeutic antibody).

Illustratively, the given amount of the selected labeled therapeutic antibody used as an Internal Standard compound, especially the given amount of labeled anti-TNF antibody selected in a group comprising Infliximab, Etanercept, Adalimumab, Certolizumab and Golimumab, or especially the given amount of anti-cancer antibody selected in a group comprising Trastuzumab, Rituximab and Bevacizumab, is preferably an amount which generates a mass spectrometry signal of the same order of magnitude as a mid-range calibration standard of the corresponding therapeutic antibody in order to limit the difference in mass spectrometry signal intensity generated by the respective amounts (i) of labeled surrogate peptides derived from enzyme proteolysis of the said labeled therapeutic antibody used as the Internal Standard compound and (ii) of the corresponding proteolysis peptides derived from the said therapeutic antibody. Illustratively, the amount ratios (e.g. as expressed as weight amount or as weight/volume amounts) between a non-labeled therapeutic antibody and the corresponding labeled therapeutic antibody may range from 1:10 to 10:1, which encompasses amount ratios ranging from 1:5 to 5:1.

Indeed, the amount of therapeutic antibodies that may be found in a test sample, especially in a test sample consisting of a human serum sample originating from a patient treated by therapeutic antibodies, may vary, depending of (i) the amount of therapeutic antibody(ies) which has(have) been administered to the said patient, (ii) the time period when the serum sample has been collected since the starting time period of the treatment, (ii) the time period of collection of the serum sample since the last administration of therapeutic antibodies, and (iv) physiological parameters which may be specific to the said patient, such as the rate of clearance of the said antibodies from the blood.

In some embodiments, the serial or set of calibration samples may further comprise one or more control calibration samples which do not contain the selected therapeutic antibody, or alternatively which do not contain any therapeutic antibody.

Most preferably, a calibration sample is prepared starting from a body fluid sample initially exempt of the selected therapeutic antibody or of the selected Internal Standard compound, and preferably serum or plasma from a non-human mammal or from a human individual, and most preferably human serum or human plasma.

Then, each of the calibration sample is subjected to the same method steps as that which is described for the test samples elsewhere in the present specification, so as to provide a serial or a set of calibration assay samples (CAS).

Then, each calibration assay sample is subjected to spectrometric analysis, and most preferably to a LC-MS/MS analysis, in the same conditions as those described for the test samples elsewhere in the present specification and the values of the spectrometry signals generated by (i) a selected surrogate peptide generated by enzyme proteolysis of the selected therapeutic antibody and (ii) by the corresponding selected labeled peptide (also termed "labeled surrogate peptide") generated by enzyme proteolysis of the selected labeled therapeutic antibody, especially by the corresponding selected peptide (also termed "labeled surrogate peptide") generated by enzyme proteolysis of the selected labeled therapeutic antibody, including a labeled anti-TNF antibody selected in a group comprising Infliximab, Etanercept, Adalimumab, Certolizumab and Golimumab or including an anti-cancer antibody selected in a group comprising Trastuzumab, Rituximab and Bevacizumab, used as the Internal Standard compound, are then measured.

Then, for each of the calibration assay sample (CAS), a ratio of (i) the spectrometry signal value generated by the selected therapeutic antibody surrogate peptide to (ii) the spectrometry signal value generated by the selected Internal Standard-derived labeled surrogate peptide is calculated.

As it will be further detailed in the present specification, a spectrometric signal value may consist of the peak area of specific SRM (Selected Reaction Monitoring), or more precisely of the mean of the peak areas of specific SRM, generated by a selected peptide of interest, typically by a selected surrogate tryptic peptide derived from the selected labeled therapeutic antibody used as an Internal Standard described herein.

Thus, it is provided a serial or a set of ratio values, each ratio value being calculated from a calibration assay sample obtained from a starting calibration sample comprising known amounts, e;g. known final concentrations, of the selected therapeutic antibody and a fixed and known amount of the Internal Standard compound.

A calibration curve may then be generated by plotting the serial or set of calculated ratio values versus the corresponding theoretical amounts of the selected therapeutic antibody, e;g. versus the corresponding known final concentrations of the selected therapeutic antibody.

As used herein, a "final" concentration of a selected therapeutic antibody is the concentration of the said therapeutic antibody in an initial Calibration Sample (CS), which CS comprises a known added amount of the said therapeutic antibody.

Sample Preparation

In some embodiments, the sample which is used in the quantification method originates from a whole human blood sample that has been previously collected from an individual. In preferred embodiments, the blood cells, and especially erythrocytes, are removed by centrifugation so as to obtain a plasma sample. In other preferred embodiments, coagulation of the whole blood sample is allowed to occur and a serum sample is obtained.

In further embodiments, the sample which is used in the quantification method may consist of other extracellular fluids such as lymphatic fluid (endolymph or perilymph) and interstitial fluid.

Most preferably, at least for determining the pharmacokinetic profile of therapeutic antibodies in an individual, the said sample is a blood plasma sample or a blood serum sample, or a sample derived from blood plasma or blood serum.

In some embodiments, the initial sample may be subjected to dilution, e.g. in an aqueous medium such as in a saline solution or in a buffer solution, before being used as the assay sample in the therapeutic antibody quantification method according to the invention.

However, in the most preferred embodiments, the initial sample, such as a plasma sample or a serum sample, is used without any pre-treatment and in particular is used as such undiluted.

As it will be described further in the present specification, according to the therapeutic antibody quantification method described herein, the sample to be tested is added with a known amount of each of the two or more of the selected labeled therapeutic antibodies used as Internal Standard compounds at step a).

In these embodiments, there is thus provided a sample containing a known amount of each of the two or more of the selected labeled therapeutic antibodies used as Internal Standard compounds and an unknown amount of therapeutic antibodies (e.g. anti-TNF antibodies or anti-cancer antibodies).

In some embodiments, the said sample comprises only two Internal Standard compounds, which are selected among anti-TNF antibodies of interest, and most preferably only two Internal Standard compounds, which are selected in a group comprising labeled Infliximab, labeled Etanercept, labeled Adalimumab, labeled Certolizumab and labeled Golimumab.

In other embodiments, the said sample comprises more than two Internal Standard compounds, which are selected among anti-TNF antibodies of interest and most preferably more than two Internal Standard compounds, which are selected in a group comprising labeled Infliximab, labeled Etanercept, labeled Adalimumab, labeled.

Certolizumab and labeled Golimumab. These other embodiments encompass those wherein the said sample comprises 3, 4 or 5 Internal Standard compounds, which are selected among anti-TNF antibodies of interest and most preferably 3, 4 or 5 Internal Standard compounds, which are selected in a group comprising labeled Infliximab, labeled Etanercept, labeled Adalimumab, labeled Certolizumab and labeled Golimumab. The various combinations of Internal Standard compounds that are added (or "spiked") are described elsewhere in the present specification.

In some embodiments, the said sample comprises only two Internal Standard compounds, which are selected among anti-cancer antibodies of interest, and most preferably only two Internal Standard compounds, which are selected in a group comprising labeled Trastuzumab, labeled Rituximab and labeled Bevacizumab.

In other embodiments, the said sample comprises more than two Internal Standard compounds, which are selected among anti-cancer antibodies of interest and most preferably more than two Internal Standard compounds, which are selected in a group comprising labeled labeled Trastuzumab, labeled Rituximab and labeled Bevacizumab. These other embodiments encompass those wherein the said sample comprises 3 Internal Standard compounds, which are selected among anti-cancer antibodies of interest.

The various combinations of Internal Standard compounds that are added (or "spiked") are described elsewhere in the present specification.

The Internal Standard compounds are subjected to each of the further steps of the therapeutic antibody quantification method described herein.

In some embodiments of the therapeutic antibody quantification method described herein, step a) comprises the following steps:

a1) adding to a test sample which may contain therapeutic antibodies a known amount of two or more labeled forms of said therapeutic antibodies such as a known amount of two or more labeled anti-TNF antibodies that may be selected in a group comprising Infliximab, Etanercept, Adalimumab, Certolizumab and Golimumab or such as a known amount of labeled anti-cancer antibodies that may be selected in a group comprising Trastuzumab, Rituximab and Bevacizumab, whereby a non-concentrated pre-proteolysis sample is provided, and a2) enriching the non-concentrated pre-proteolysis sample in antibodies, whereby a pre-proteolysis sample is provided.

Pre-Proteolysis Mixture Preparation

At step a), or alternatively at step a2), there is thus provided a pre-proteolysis mixture containing a known amount of Internal Standard compounds and an unknown amount of therapeutic antibodies.

In most preferred embodiments, the said pre-proteolysis mixture comprises two or more labeled therapeutic antibodies In some most preferred embodiments, the said pre-proteolysis mixture comprises two or more labeled anti-TNF antibodies, especially two or more labeled anti-TNF antibodies selected in a group comprising Infliximab, Etanercept, Adalimumab, Certolizumab and Golimumab, as Internal Standard compounds.

In some other most preferred embodiments, the said pre-proteolysis mixture comprises two or more labeled anti-cancer antibodies, especially two or more anti-cancer antibodies selected in a group comprising Trastuzumab, Rituximab and Bevacizumab.

Enriching the Sample in Therapeutic Antibodies

In some embodiments of the therapeutic antibody quantification method described herein, step a), or alternatively step a2), may consist of a step wherein the enrichment in therapeutic antibodies is performed by immunocapture, that is by complexing the therapeutic antibodies possibly present in the test sample with the corresponding therapeutic antibodies ligands, and wherein reversible complexes formed between the therapeutic antibodies and the said therapeutic antibodies ligands may be purified and the complexed anti-TNF antibodies may be dissociated and harvested.

These embodiments of step a), or step a2), of the quantification method may be performed by any method known in the art, which includes affinity chromatography and immunocapture. Affinity chromatography and immunocapture are both based on the same technical principle of binding and eluate the therapeutic antibodies by using a substrate wherein therapeutic antibodies ligands are immobilized, preferably a substrate wherein the corresponding target molecules are immobilized.

Thus, according to some aspects of these embodiments of step a), or alternatively step a2), of the therapeutic antibody quantification method, immunocapture may be performed by using a substrate onto which target molecules (e.g. human TNF alpha molecules, human Her2/Neu; molecules, human VEGF molecules or human CD20 molecules) are immobilized.

Also, according to some other aspects of these embodiments of step a), or alternatively step a2), of the therapeutic antibody quantification method, immunocapture may be performed by using a substrate onto which Fc-binding molecules (e.g. protein A molecules or protein G molecules) are immobilized.

Enriching the Sample in Therapeutic Antibodies by Immunocapture

This embodiment is illustrated hereunder when the therapeutic antibody quantification method described herein is used for quantifying anti-TNF antibodies. Indeed, the one skilled in the art may apply the same technique for quantifying therapeutic antibodies directed against other targets of interest.

In some embodiments illustrated in the examples herein, the test sample is enriched in anti-TNF antibodies by using a method of immunocapture. According to these embodiments, enriching in anti-TNF antibodies by depletion in non-antibody proteins is performed by using an affinity chromatography support onto which TNF alpha molecules are immobilized. More precisely, according to this method, biotinylated TNF alpha is immobilized on a support and the resulting support is brought into contact with to the previously spiked test sample so as to capture the TNF binding molecules that are present in the spiked test sample, which includes (i) the two or more Stable Isotope Labeled (SIL) anti-TNF antibodies used as Internal Standards and (ii) the other anti-TNF antibodies that are possibly present in the test sample before spiking with the SIL anti-TNF antibodies.

Then, the anti-TNF antibodies are eluted from the chromatographic support and collected for further processing.

In some preferred embodiments, it is made use of a Reverse Mass Spectrometry Immuno-Assay (MSIA) method such as that which is termed D.A.R.T.s which employs reagents, including streptavidin-coated substrate that is commercialized by the Company Thermo Scientific (San Diego, USA).

In some other preferred embodiments, immunocapture may be performed by using the streptavidin-coated beads commercialized under the name of Dynabeads™, such as Dynabeads™ M-280 Streptavidin commercialized by the Company InVitrogen (Cergy-Pontoise, France).

Enriching in Therapeutic Antibodies by Depletion in Non-Antibody Protein

In some embodiments, of the therapeutic antibody quantification method described herein, step a), or alternatively step a2), may consist of a step wherein the enrichment in therapeutic antibodies is performed by depletion of a substantial part of the proteins, except the antibody proteins, that are initially contained in the test sample.

The step of depletion of said substantial part of the proteins may consist of a protein depletion step, such as a protein differential depletion step, and preferably of an albumin depletion step.

In some embodiments of the therapeutic antibody quantification method described herein, the non-concentrated proteolysis sample is subjected to a protein depletion step.

In some embodiments of the therapeutic antibody quantification method described herein, the non-concentrated proteolysis sample is subjected to a protein differential depletion step.

A differential depletion step may refer, preferably, to a differential precipitation of proteins distinct from albumin, according to their structural and biochemical characteristics. For instance, a differential depletion step may consist in precipitating only antibodies of a certain isotope, such as IgG antibodies; or may consist in precipitating only proteins of a certain size (or range of size), such as proteins of a size lower than 80 kDa, or alternatively higher than 80 kDa.

A differential depletion step may provide a final sample which contains essentially the protein(s) of interest (i.e. antibodies), and to discard protein(s) not of interest in order to obtain a higher sensitivity than by depleting albumin only However, general enrichment in therapeutic antibodies (such as IgG antibodies) by using a method of precipitation of plasma proteins possesses several drawbacks. Such a method for general precipitation of plasma proteins, although it is simple, fast, inexpensive and allows access to the measurement of total protein fraction, the resulting plasma proteins-enriched mixture is not sufficiently enriched in therapeutic antibodies, which is detrimental to the repeatability of the subsequent step of trypsin proteolysis, and finally be detrimental to the accuracy of the therapeutic (i.e. anti-TNF and/or anti-cancer) antibody quantification method. Consequently, although such a precipitation method may be used for performing the therapeutic antibodies quantification method described herein, such an embodiment of sample preparation is not the most preferred.

According to some aspects of these embodiments, depletion in non-antibody proteins may be performed by using specific resins having affinity for proteins that are known in the art, such as the Cibacron-blue resin, which includes the Cibacron-blue™ 3 GA agarose commercialized notably by the Company Sigma-Aldrich (MI, USA).

According to some other aspects of these embodiments, depletion in non-antibody proteins may be performed by precipitation of a substantial part of the proteins initially contained in the test sample, except the antibody proteins.

In some embodiments of the quantification method described herein, the sample, optionally comprising the Internal Standard compound, is enriched in therapeutic antibodies, such as IgG antibodies.

Various methods for enriching a sample in therapeutic antibodies are known in the art.

In some embodiments, enrichment in therapeutic antibodies may be performed by ammonium sulfate precipitation, by using methods well known in the art, so as to obtain an antibody-enriched composition, such as an IgG-enriched composition.

According to further aspects of these embodiments, depletion in non-antibody proteins may be performed by precipitation of the antibody proteins initially contained in the test sample, such as by performing antibody precipitation with ammonium sulfate, e.g. by using a saturated ammonium sulfate solution (30% v/v).

Protein A Chromatography

In some embodiments of the quantification method described herein, the sample, optionally comprising the Internal Standard compound, is enriched in therapeutic antibodies, in particular IgG antibodies.

In some embodiments, enrichment in therapeutic antibodies may be performed by affinity chromatography, which includes the use of chromatography substrates onto which have been immobilized relevant ligands such as protein A, protein G or alternatively antibodies binding to the Fc portion of therapeutic antibodies, as well as nucleic acid or peptide aptamers that bind to the Fc portion of therapeutic antibodies.

The step of enrichment in therapeutic antibodies allows separating antibodies from other abundant plasma proteins and thus contributes to improve sensitivity and reproducibility of the anti-TNF and anti-cancer antibody quantification method.

Preferably herein, enrichment in therapeutic antibodies by using protein A or protein G chromatography is preferred.

In particular, IgG enrichment by subjecting the sample to protein A or protein G chromatography allows depletion of almost the whole plasma proteins while retaining the whole IgG antibodies initially contained therein, which includes the whole anti-TNF antibodies and anti-cancer initially contained therein.

Most preferably, enrichment in IgG antibodies is performed by protein A chromatography.

In the embodiments wherein protein A chromatography is used, elution of the retained therapeutic antibodies, in particular IgG antibodies, is conventionally performed at an acidic pH, generally at a pH in the range of 2-3, preferably at a pH of 2.8. Then, the fraction containing the most part of the therapeutic antibodies may be collected by elution using a formic acid solution (0.5%-1% v/v) at a pH ranging from 1 to 3. After evaporation of the formic acid, the dry sample may be resuspended in a liquid medium containing ammonium bicarbonate at a pH ranging from 7 to 8, for further processing.

In these embodiments, there is thus provided an antibody-enriched composition, in particular an IgG-enriched composition, containing a known amount of the Internal Standard compounds and an unknown amount of anti-TNF and/or anti-cancer antibodies.

Concentrating the Antibody-Enriched (i.e. IgG Enriched) Composition

In some embodiments, and especially in embodiments wherein the antibody-enriched composition is obtained by a step of chromatography wherein sample dilution is susceptible to occur, the said composition is then subjected to a concentration step, so as to provide a concentrated antibody-enriched composition.

In these embodiments, the concentration step may be performed by any method known in the art, including dialysis and filtration, e.g. microfiltration or ultrafiltration.

In preferred embodiments, the concentration step is an ultrafiltration step wherein a filter membrane of a relevant cut-off value is used.

Illustratively, the ultrafiltration step may be performed by using an ultrafiltration membrane having a cut-off value of about 100 kDa.

In the embodiments wherein the concentration step is an ultrafiltration step, a buffer exchange is performed during the ultrafiltration step so as to optimize the conditions of the further steps of the method are conducted. Notably, the buffer exchange that may be performed during the ultrafiltration step allows obtaining a concentrated IgG-enriched composition in which the subsequent step of proteolysis by trypsin will be optimally realized.

Proteolysis Step

This step is step b) of the general therapeutic antibody quantification method described herein.

As it is described further herein, the proteolysis step consists of subjecting the pre-proteolysis mixture, containing the labeled therapeutic antibodies (used as Internal Standard compounds) and possibly the non-labeled therapeutic antibodies to be quantified, to an enzyme proteolysis so as to generate, notably, therapeutic antibody-derived proteolysis peptides, namely (i) labeled therapeutic antibody-derived proteolysis peptides generated from the tow or more Internal Standard compounds added at step a) and non-labeled therapeutic antibody-derived proteolysis peptides generated from the non-labeled therapeutic antibodies to be quantified, if these non-labeled therapeutic antibodies are present initially in the test sample.

A plurality of embodiments of a proteolysis step may be performed. In particular, the proteolysis enzymes, which may also be termed proteases herein, may be selected in a vast group of proteases well known in the art. Since the cleavage site(s) of each known protease is part of the technical knowledge of the one skilled in the art, the selection of a specific protease at step b) is correlated to the subsequent monitoring of the expected resulting therapeutic antibodies proteolysis peptides generated therefrom, by mass spectrometric analysis.

In some embodiments of the proteolysis step that are illustrated in the examples herein, the selected protease possesses trypsin activity.

In some other embodiments of the proteolysis step that are illustrated in the examples herein, the selected protease possesses a hinge-targeting activity.

One-Step Trypsin Proteolysis

According to these embodiments of the proteolysis step, trypsin is added to the pre-proteolysis mixture, so as to generate (i) tryptic peptides from the therapeutic antibody initially contained in the test sample and (ii) tryptic peptides generated by trypsin proteolysis of the labeled therapeutic antibodies used as Internal Standard compounds. The specific tryptic peptides derived from the internal standard monoclonal antibody may also be termed "surrogate peptides" herein.

In some embodiments, the one-step trypsin proteolysis is performed by using trypsin as the sole added protease.

In some other embodiments that are illustrated in the examples herein, the one-step trypsin proteolysis is performed by using a combination of trypsin and endoproteinase Lys-C (also termed "EndolysC" herein) as the "protease". According to these embodiments, the combination or mixture of trypsin and endoproteinase Lys-C contains advantageously a weight amount ratio of trypsin to EndolysC ranging from 0.1:1 to 20:1, which encompasses a weight amount ratio from 0.5:1 to 15:1, preferably a weight amount ratio ranging from 1:10:1. As it is well known in the art, trypsin cleaves peptide chains mainly at the carboxyl side of the amino acids lysine and arginine, except when either is followed by proline.

As it is also well known in the art EndolysC cleaves peptide chains at the carboxyl side of lysine amino acid.

The proteolysis step is preferably performed in conditions that are optimal for:
(i) generating all the expected surrogate tryptic peptides, and
(ii) avoiding trypsin autolysis.

It may be used a purified trypsin having a low ability to autolysis. Illustratively, it may be used a trypsin termed Trypsin Gold® which is marketed by the company Promega (Madison, Wis., United States).

Optimal proteolysis conditions may be reached by using a trypsin/total protein molar ratio ranging from 1/100 to 1/1.

In most preferred embodiments, the proteolysis step is performed in non-denaturing conditions, i.e. in conditions which do not cause protein denaturation. Notably, the proteolysis step is performed in the absence of a protein denaturation agent such as urea or guanidium hydrochloride.

Proteolysis in the presence of trypsin is performed during a period of time that may be optimally adapted by the one skilled in the art.

Advantageously, proteolysis is performed at 37° C. during a period of time ranging from 0.5 hour to 15 hours, preferably from 1 hour to 10 hours, and most preferably ranging from 2 hours to 4 hours. In some embodiments, proteolysis is performed at 37° C. overnight.

The one-step proteolysis step is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

In most preferred embodiments, the one-step proteolysis step is performed under non-denaturing conditions that is under conditions wherein there is no denaturation of the proteins initially contained in the pre-proteolysis sample.

In some embodiments, proteolysis is stopped by acidification of the resulting mixture, for example by adding an appropriate acid such as formic acid, so as to decrease the pH of the said resulting mixture below pH 6.

Two-Step Trypsin Proteolysis

In some embodiments, step b) may be performed by a two-step trypsin proteolysis. In these embodiments, step b)

comprises two enzyme proteolysis steps, namely step b1) of enzyme proteolysis under denaturing conditions and step b2) of enzyme proteolysis in non-denaturing conditions, as it is illustrated in the examples herein.

The enzyme(s) which is used at steps b1) and b2) may be the same as those disclosed for performing the "one-step trypsin proteolysis" specified above.

In some embodiments, the enzyme(s) which is(are) used at step b1) is(are) the same as that(those) which is(are) used ate step b2). In some other embodiments, the enzyme(s) which is(are) used at step b1) is(are) distinct from that (those) which is(are) used ate step b2).

According to the two-step proteolysis method, step b1) consists of a pre-digestion step wherein aimed at increasing the sensitivity of the proteins contained in the pre-proteolysis sample, and mainly the trypsin sensitivity of the antibodies (including the therapeutic antibodies) contained in the pre-proteolysis sample.

Step b1) is performed in denaturing conditions, such that in the presence of urea, advantageously at a final concentration ranging from 4 M to 0.1 M, preferably at a final concentration of about 4 M.

In some embodiments, step b1) is performed by using a protease mixture of EndolysC and trypsin in an amount as described of the "one-step trypsin proteolysis" embodiment above.

In some other embodiments, step b1) is performed by using Endolys C as the sole protease. According to these other embodiments, EndolysC is present in the resulting sample at a final concentration ranging from 0.01 µg/mL to 10 µg/mL.

At step b1) proteolysis is performed during a time period of 0.5 h to 6 h; advantageously from 0.75 h to 4 h, preferably from 1 h to 3 h, and may be performed during a time period of about 2 h.

At step b1) proteolysis is preferably performed at 37° C.

At step b1) proteolysis is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

Further, step b2) is performed by using a protease mixture comprising trypsin.

In some embodiments, step b2) is performed by using a protease mixture of EndolysC and trypsin in an amount as described of the "one-step trypsin proteolysis" embodiment above. In some aspects of these embodiments, the protease mixture of EndolysC and trypsin is added at step b1) and there is preferably no addition of further protease or protease mixture at step b2) since the said protease or protease mixture is already present at the appropriate final concentration in the pre-digestion sample obtained at the end of step b1). According to these embodiments, step b1) may performed in conditions wherein EndolysC is active and trypsin is inactive, and wherein trypsin is rendered active at step b2) by bringing changes in the sample physico-chemical conditions such that by adding an appropriate buffer composition at the beginning of step b2). Illustratively, ammonium bicarbonate buffer solution at an appropriate final concentration may be added at the beginning of step b2).

In some other aspects of these embodiments wherein step b1) is performed by using EndolysC, an appropriate amount of trypsin is added at the beginning of step b2), so that the sample used at the beginning of step b2) comprises a protease mixture of EndolysC and trypsin, at the desired ratio and final concentration.

In some other embodiments, step b1) is performed by using trypsin as the sole added protease. According to these other embodiments, there is preferably no further addition of trypsin at step b2).

Advantageously, proteolysis at step b2) is performed at 37° C. during a period of time ranging from 0.5 hour to 15 hours, preferably from 1 hour to 10 hours, and most preferably ranging from 2 hours to 4 hours. In some embodiments, proteolysis is performed at 37° C. overnight.

The one-step proteolysis at step b2) is performed at a pH of 6 or more. Further, the one-step proteolysis step is advantageously performed at a pH of less than 8.5, preferably at a pH of 8 or less, which includes at a pH of 7.5 or less, e.g. at a pH of about 7.

Proteolysis with a Hinge-Targeting Protease

In some embodiments of step b), proteolysis is performed by using a hinge-targeting protease. Hinge-targeting proteases are known proteases effecting a cleavage in an antibody protein in the hinge region so as to generate (i) two Fc regions of the heavy chains and (ii) an F(ab')2 moiety, respectively. Fab moieties may then be obtained from the F(ab')2 moiety, by methods well known form the one skilled in the art, such as by using a reducing agent such as dithiothreitol (DTT).

At step b), the hinge-targeting protease is preferably selected in a group comprising Gelatinase A (MMP-2) (Tamerius et al., 1975, Int J Cancer, Vol. 16: 456-464), Stromyelysin (MMP-3) (Tamerius et al., 1975, Int J Cancer, Vol. 16: 456-464; Tamerius et al., 1976, J Immunol, Vol. 116: 724-730; Reichert et al., 2010, Mabs, Vol. 2: 84-100), Matrilysin (MMP-7) (Tamerius et al., 1975, Int J Cancer, Vol. 16: 456-464; Tamerius et al., 1976, J Immunol, Vol. 116: 724-730; Reichert et al., 2010, Mabs, Vol. 2: 84-100), Gelatinase B (MMP-9) (Reichert et al., 2010, Mabs, Vol. 2: 84-100), Macrophage metalloelastase (MMP-12) (Tamerius et al., 1976, J Immunol, Vol. 116: 724-730; Reichert et al., 2010, Mabs, Vol. 2: 84-100), Collagenase-3 (MMP-13) (Tamerius et al., 1976, J Immunol, Vol. 116: 724-730), Cathepsin G (Reichert et al., 2010, Mabs, Vol. 2: 84-100), Pseudolysin (Strohl et al., 2009, Curr Opinion Biotechnol, Vol. 20: 685-691), Mirabilysin, Glutamyl endopeptidase I (GluV8) (Tamerius et al., 1976, J Immunol, Vol. 116: 724-730; Reichert et al., 2010, Mabs, Vol. 2: 84-100), Streptopain (SpeB) (Brerski et al., 2010, mAbs, Vol. 2:3: 212-220), Trepolisin (Brerski et al., 2010, mAbs, Vol. 2:3: 212-220) and Immunoglobulin-degrading enzyme from Streptococcus (ideS) (Tamerius et al., 1976, J Immunol, Vol. 116: 724-730; Reichert et al., 2010, Mabs, Vol. 2: 84-100).

Most preferably, these embodiments of step b) are performed by using Immunoglobulin-degrading enzyme from Streptococcus (ideS) as the hinge-targeting protease. In these embodiments, it may be used ideS which is immobilized on an appropriate solid support, e.g. an agarose support, such as in the FragIT™ kit commercialized by the Company Genovis (Luna, Sweden) or the Company Sigma-Aldrich (Saint Louis, Mo., United States).

At step b) the pre-proteolysis sample is subjected to proteolysis with an ideS protease at room temperature during a time period ranging from 5 mins to 96 hours, advantageously from 10 mins to 50 hours, which includes a time period ranging from 1 hour to 5 hours.

The resulting proteolysis mixture may be collected by centrifugation and/or protein precipitation, before-suspension, as it is illustrated in the examples herein.

Quantification of Therapeutic Antibodies by Mass Spectrometric Analysis

This step encompasses steps c) and d) of the general therapeutic antibody quantification method described herein.

Step c) is performed by mass spectrometry, according to techniques of protein quantification by mass spectrometry that are known in the art.

Preferably, step c) is performed according to the method of Liquid Chromatography coupled to tandem Mass Spectrometry (LC-MS/MS), as it is shown in the examples herein.

Preferably, it is used a triple quadrupole (QqQ) mass spectrometer equipped with an ESI source operating in positive ion mode and using multiple reaction monitoring (MRM) mode for quantification.

In some embodiments, Liquid Chromatography is performed with a reverse phase chromatography substrate.

Then, in some embodiments, the most abundant state of charge of (i) selected surrogate proteolytic peptides derived from the labeled therapeutic antibodies used as Internal Standard compounds and of (ii) the proteolytic peptides derived from the therapeutic antibodies initially present in the test sample are observed preferably between 200 m/z and 2000 m/z in ESI ionization source and are selected and fragmented.

At the quantification step by mass spectrometry, it is researched the Selected Reaction Monitoring (SRM) transitions specific of
  (i) the selected surrogate proteolytic peptide(s) of a therapeutic antibody and of
  (ii) the corresponding labeled proteolytic peptide derived from the corresponding labeled therapeutic antibody used as one of the Internal Standard compounds.

As already mentioned elsewhere in the present specification, performing the anti-TNF antibodies quantification method of the invention wherein the proteolysis step b) makes use of trypsin as the sole protease or as a protease contained in a protease mixture, the one or more selected proteolysis peptides are selected in a group comprising:
  for Infliximab: peptides of SEQ ID NO. 1-8,
  for Etanercept: peptides of SEQ ID NO. 9-15,
  for Adalimumab: peptides of SEQ ID NO. 16-23,
  for Certolizumab: peptides of SEQ ID NO. 24-30, and
  for Golimumab: peptides of SEQ ID NO. 31-37.
  for Trastuzumab: peptides of SEQ ID NO. 47-53.
  for Rituximab: peptides of SEQ ID NO. 54-64.
  for Bevacizumab: peptides of SEQ ID NO. 65-72.

In the embodiments wherein the proteolysis step is performed by using trypsin or a trypsin-containing protease composition wherein anti-TNF antibodies are quantified and wherein a labeled counterpart of Infliximab is used as an Internal Standard compound, the number of selected proteolysis peptides for which a mass spectrometric signal ratio is determined at step c) may vary according notably to of the number of available proteolysis peptides. The number of selected proteolysis peptides for which a mass spectrometric signal ratio is determined at step c) may vary from 1 to 8 proteolysis peptides, depending from the number of proteolysis peptides which are available, which encompasses 1, 2, 3, 4, 5, 6, 7, and 8 selected proteolysis peptides.

In the embodiments of the therapeutic antibody quantification method wherein anti-TNF antibodies are quantified and wherein a labeled counterpart of Infliximab is used as an Internal Standard compound and wherein two selected proteolysis peptides are monitored, these may be selected in a group comprising SEQ ID NO. 1 and 2; SEQ ID NO. 1 and 3; SEQ ID NO. 1 and 4; SEQ ID NO. 1 and 5; SEQ ID NO. 1 and 6; SEQ ID NO. 1 and 7; SEQ ID NO. 1 and 8; SEQ ID NO. 2 and 3; SEQ ID NO. 2 and 4; SEQ ID NO. 2 and 5; SEQ ID NO. 2 and 6; SEQ ID NO. 2 and 7; SEQ ID NO. 2 and 8; SEQ ID NO. 3 and 4; SEQ ID NO. 3 and 5; SEQ ID NO. 3 and 6; SEQ ID NO. 3 and 7; SEQ ID NO. 3 and 8; SEQ ID NO. 4 and 5; SEQ ID NO. 4 and 6; SEQ ID NO. 4 and 7; SEQ ID NO. 4 and 8; SEQ ID NO. 5 and 6; SEQ ID NO. 5 and 7; SEQ ID NO. 5 and 8; SEQ ID NO. 6 and 7; and SEQ ID NO. 7 and 8.

In the embodiments of the therapeutic antibody quantification method wherein anti-TNF antibodies are quantified and wherein a labeled counterpart of Infliximab is used as an Internal Standard compound and wherein three selected proteolysis peptides are monitored, these may be selected in a group comprising SEQ ID NO. 1, 2 and 3; SEQ ID NO. 1, 2 and 4; SEQ ID NO. 1, 2 and 5; SEQ ID NO. 1, 2 and 6; SEQ ID NO. 1, 2 and 7; SEQ ID NO. 1, 2 and 8; SEQ ID NO. 1, 3 and 4; SEQ ID NO. 1, 3 and 5; SEQ ID NO. 1, 3 and 6; SEQ ID NO. 1; 3 and 7; SEQ ID NO. 1, 3 and 8; SEQ ID NO. 1, 4 and 5; SEQ ID NO. 1, 4 and 6; SEQ ID NO. 1, 4 and 7; SEQ ID NO. 1; 4 and 8; SEQ ID NO. 1; 5 and 6; SEQ ID NO. 1, 5 and 7; SEQ ID NO. 1, 5 and 8; SEQ ID NO. 1; 6 and 7; SEQ ID NO. 1, 6 and 8; SEQ ID NO. 1, 7 and 8; SEQ ID NO. 2, 3 and 4; SEQ ID NO. 2, 3 and 5; SEQ ID NO. 2, 3 and 6; SEQ ID NO. 2, 3 and 7; SEQ ID NO. 2, 3 and 8; SEQ ID NO. 2, 4 and 5; SEQ ID NO. 2, 4 and 6; SEQ ID NO. 2, 4 and 7; SEQ ID NO. 2, 4 and 8; SEQ ID NO. 2, 5 and 6; SEQ ID NO. 2, 5 and 7; SEQ ID NO. 2, 5 and 8; SEQ ID NO. 2, 6 and 7; SEQ ID NO. 2, 6 and 8; SEQ ID NO. 2, 7 and 8; SEQ ID NO. 3, 4, and 5; SEQ ID NO. 3, 4 and 6; SEQ ID NO. 3, 4 and 7; SEQ ID NO. 3, 4 and 8; SEQ ID NO. 3, 5 and 6, SEQ ID NO. 3, 5 and 7; SEQ ID NO. 3, 5 and 8; SEQ ID NO. 3, 6 and 7; SEQ ID NO. 3, 6 and 8, SEQ ID NO. 3, 7 and 8; SEQ ID NO. 4, 5 and 6; SEQ ID NO. 4, 5 and 7; SEQ ID NO. 4, 5 and 8; SEQ ID NO. 4, 6 and 7; SEQ ID NO. 4, 6 and 8; SEQ ID NO. 4, 7 and 8; SEQ ID NO. 5, 6 and 7; SEQ ID NO. 5, 6 and 8; SEQ ID NO. 5, 7 and 8; SEQ ID NO. 6, 7 and 8.

In the embodiments of the therapeutic antibody quantification method wherein anti-TNF antibodies are quantified and wherein a labeled counterpart of Infliximab is used as an Internal Standard compound and wherein four selected proteolysis peptides are monitored, these may be selected in a group comprising SEQ ID NO. 1, 2, 3 and 4; SEQ ID NO. 1, 2 3 and 5; SEQ ID NO. 1, 2, 3, and 6; SEQ ID NO. 1, 2, 3 and 7; SEQ ID NO. 1, 2, 3 and 8; SEQ ID NO. 1, 3, 4 and 5; SEQ ID NO. 1, 3, 4 and 6; SEQ ID NO. 1, 3, 4 and 7; SEQ ID NO. 1, 3, 4 and 8; SEQ ID NO. 1, 4, 5 and 6; SEQ ID NO. 1, 4, 5 and 7; SEQ ID NO. 1, 4, 5 and 8; SEQ ID NO. 1, 5, 6 and 7; SEQ ID NO. 1, 5, 6 and 8; SEQ ID NO. 1, 5, 7 and 8; SEQ ID NO. 2, 3, 4 and 5; SEQ ID NO. 2, 3, 4 and 6; SEQ ID NO. 2, 3, 4 and 7; SEQ ID NO. 2, 3, 4 and 8; SEQ ID NO. 2, 4, 5 and 6; SEQ ID NO. 2, 4, 5 and 7; SEQ ID NO. 2, 4, 5 and 8; SEQ ID NO. 2, 5, 6 and 7; SEQ ID NO. 2, 5, 6 and 8; SEQ ID NO. 2, 6, 7 and 8; SEQ ID NO. 3, 4, 5 and 6; SEQ ID NO. 3, 4, 5 and 7; SEQ ID NO. 3, 4, 5 and 8; SEQ ID NO. 3, 5, 6 and 7; SEQ ID NO. 3, 5, 7 and 8; SEQ ID NO. 3, 6, 7 and 8; SEQ ID NO. 4, 5, 6 and 7; SEQ ID NO. 4, 5, 6 and 8; SEQ ID NO. 4, 6, 7 and 8; SEQ ID NO. 5, 6, 7 and 8.

In the embodiments of the therapeutic antibody quantification method wherein anti-TNF antibodies are quantified and wherein a labeled counterpart of Infliximab is used as an Internal Standard compound and wherein five selected proteolysis peptides are monitored, these may be selected in a group comprising SEQ ID NO. 1, 2, 3, 4 and 5; SEQ ID NO.

1, 2, 3, 4, and 6; SEQ ID NO. 1, 2, 3, 4 and 7; SEQ ID NO. 1, 2, 3, 4 and 8; SEQ ID NO. 1, 3, 4, 5 and 6; SEQ ID NO. 1, 3, 4, 5 and 7; SEQ ID NO. 1, 3, 4, 5 and 8; SEQ ID NO. 1, 4, 5, 6 and 7; SEQ ID NO. 1, 4, 5, 6 and 8; SEQ ID NO. 1, 5, 6, 7 and 8; SEQ ID NO. 2, 3, 4, 5 and 6; SEQ ID NO. 2, 3, 4, 5 and 7; SEQ ID NO. 2, 3, 4, 5 and 8; SEQ ID NO. 2, 4, 5, 6 and 7; SEQ ID NO. 2, 4, 5, 6 and 8; SEQ ID NO. 2, 5, 6, 7 and 8; SEQ ID NO. 3, 4, 5, 6 and 7; SEQ ID NO. 3, 4, 5, 6 and 8; SEQ ID NO. 3, 5, 6, 7 and 8; SEQ ID NO. 4, 5, 6, 7 and 8.

In the embodiments of the therapeutic antibody quantification method wherein anti-TNF antibodies are quantified and wherein a labeled counterpart of Infliximab is used as an Internal Standard compound and wherein six selected proteolysis peptides are monitored, these may be selected in a group comprising SEQ ID NO. 1, 2, 3, 4, 5 and 6; SEQ ID NO. 1, 2, 3, 4, 5 and 7, SEQ ID NO. 1, 2, 3, 4, 5 and 8; SEQ ID NO. 1, 3, 4, 5, 6 and 7; SEQ ID NO. 1, 3, 4, 5, 6 and 8; SEQ ID NO. 1, 4, 5, 6, 7 and 8; SEQ ID NO. 2, 3, 4, 5, 6 and 7; SEQ ID NO. 2, 3, 4, 5, 6 and 8; SEQ ID NO. 2, 4, 5, 6, 7 and 8; SEQ ID NO. 3, 4, 5, 6, 7 and 8;

In the embodiments of the therapeutic antibody quantification method wherein anti-TNF antibodies are quantified and wherein a labeled counterpart of Infliximab is used as an Internal Standard compound and wherein seven selected proteolysis peptides are monitored, these may be selected in a group comprising SEQ ID NO. 1, 2, 3, 4, 5, 6 and 7; SEQ ID NO. 1, 2, 3, 4, 5, 6 and 8; SEQ ID NO. 1, 3, 4, 5, 6, 7 and 8; SEQ ID NO. 2, 3, 4, 5, 6, 7 and 8.

In the embodiments of the therapeutic antibody quantification method wherein anti-TNF antibodies are quantified and wherein a labeled counterpart of Infliximab is used as an Internal Standard compound and wherein eight selected proteolysis peptides are monitored, these may be selected in a group comprising SEQ ID NO. 1, 2, 3, 4, 5, 6, 7 and 8.

In the embodiments wherein the proteolysis step is performed by using trypsin or a trypsin-containing protease composition wherein anti-TNF antibodies are quantified and wherein a labeled counterpart of Etanercept is used as an Internal Standard compound, the number of selected proteolysis peptides for which a mass spectrometric signal ratio is determined at step c) may vary from 1 to 7, which encompasses 1, 2, 3, 4, 5, 6 and 7 selected proteolysis peptides.

In the embodiments wherein anti-TNF antibodies are quantified and wherein a labeled counterpart of Etanercept is used as an Internal Standard compound wherein two selected proteolysis peptides are monitored, these may be selected in a group comprising SEQ ID NO. 9 and 10; SEQ ID NO. 9 and 11; SEQ ID NO. 9 and 12; SEQ ID NO. 9 and 13; SEQ ID NO. 9 and 14; SEQ ID NO. 9 and 15; SEQ ID NO. 10 and 11; SEQ ID NO. 10 and 12; SEQ ID NO. 10 and 13; SEQ ID NO. 10 and 14; SEQ ID NO. 10 and 15; SEQ ID NO. 11 and 12; SEQ ID NO. 11 and 13; SEQ ID NO. 11 and 14; SEQ ID NO. 11 and 15; SEQ ID NO. 12 and 13; SEQ ID NO. 12 and 14; SEQ ID NO. 12 and 15; SEQ ID NO. 13 and 14; SEQ ID NO. 13 and 15; SEQ ID NO. 14 and 15.

In the embodiments wherein anti-TNF antibodies are quantified and wherein a labeled counterpart of Etanercept is used as an Internal Standard compound wherein three selected proteolysis peptides are monitored, these may be selected in a group comprising SEQ ID NO. 9, 10 and 11; SEQ ID NO. 9, 10 and 12; SEQ ID NO. 9, 10 and 13; SEQ ID NO. 9, 10 and 14; SEQ ID NO. 9, 10 and 15; SEQ ID NO. 9, 11 and 12; SEQ ID NO. 9, 11 and 13; SEQ ID NO. 9, 11 and 14; SEQ ID NO. 9, 11 and 15; SEQ ID NO. 9, 12 and 13; SEQ ID NO. 9, 12 and 14; SEQ ID NO. 9, 12 and 15; SEQ ID NO. 9; 13 and 14; SEQ ID NO. 9, 13 and 15; SEQ ID NO. 9; 14 and 15; SEQ ID NO. 10, 11 and 12; SEQ ID NO. 10, 11 and 13; SEQ ID NO. 10, 11 and 14; SEQ ID NO. 10, 11 and 15; SEQ ID NO. 10, 12 and 13; SEQ ID NO. 10, 12 and 14; SEQ ID NO. 10, 12 and 15; SEQ ID NO. 10, 13 and 14; SEQ ID NO. 10, 13 and 15; SEQ ID NO. 10, 14 and 15; SEQ ID NO. 11, 12, and 13; SEQ ID NO. 11, 12 and 14; SEQ ID NO. 11, 12 and 15; SEQ ID NO. 11, 13 and 14; SEQ ID NO. 11, 13 and 15; SEQ ID NO. 11, 14 and 15; SEQ ID NO. 12, 13 and 14; SEQ ID NO. 12, 13 and 15; SEQ ID NO. 13, 14 and 15.

In the embodiments wherein anti-TNF antibodies are quantified and wherein a labeled counterpart of Etanercept is used as an Internal Standard compound wherein four selected proteolysis peptides are monitored, these may be selected in a group comprising SEQ ID NO. 9, 10, 11 and 12; SEQ ID NO. 9, 10 11 and 13; SEQ ID NO. 9, 10, 11, and 14; SEQ ID NO. 9, 10, 11 and 15; SEQ ID NO. 9, 11, 12 and 13; SEQ ID NO. 9, 11, 12 and 14; SEQ ID NO. 9, 11, 12 and 15; SEQ ID NO. 9, 12, 13 and 14; SEQ ID NO. 9, 12, 13 and 15; SEQ ID NO. 9, 13, 14 and 15; SEQ ID NO. 10, 11, 12 and 13; SEQ ID NO. 10, 11, 12 and 14; SEQ ID NO. 10, 11, 12 and 15; SEQ ID NO. 10, 12, 13 and 14; SEQ ID NO. 10, 12, 13 and 15; SEQ ID NO. 10, 13, 14 and 15; SEQ ID NO. 11, 12, 13 and 14; SEQ ID NO. 11, 12, 13 and 15; SEQ ID NO. 11, 13, 14 and 15; SEQ ID NO. 12, 13, 14 and 15.

In the embodiments wherein anti-TNF antibodies are quantified and wherein a labeled counterpart of Etanercept is used as an Internal Standard compound wherein five selected proteolysis peptides are monitored, these may be selected in a group comprising SEQ ID NO. 9, 10, 11, 12 and 13; SEQ ID NO. 9, 10, 11, 12, and 14; SEQ ID NO. 9, 10, 11, 12 and 15; SEQ ID NO. 9, 11, 12, 13 and 14; SEQ ID NO. 9, 11, 12, 13 and 15; SEQ ID NO. 9, 12, 13, 14 and 15; SEQ ID NO. 10, 11, 12, 13 and 14; SEQ ID NO. 10, 11, 12, 13 and 15; SEQ ID NO. 10, 12, 13, 14 and 15; SEQ ID NO. 11, 12, 13, 14 and 15.

In the embodiments wherein anti-TNF antibodies are quantified and wherein a labeled counterpart of Etanercept is used as an Internal Standard compound wherein six selected proteolysis peptides are monitored, these may be selected in a group comprising SEQ ID NO. 9, 10, 11, 12, 13 and 14; SEQ ID NO. 9, 10, 11, 12, 13 and 15, SEQ ID NO. 9, 11, 12, 13, 14 and 15; SEQ ID NO. 10, 11, 12, 13, 14 and 15.

In the embodiments wherein seven selected proteolysis peptides are monitored, these may be selected in a group comprising SEQ ID NO. 9, 10, 11, 12, 13, 14 and 15.

In the embodiments wherein the proteolysis step is performed by using trypsin or a trypsin-containing protease composition and wherein a labeled counterpart of Adalimumab is used as an Internal Standard compound, the number of selected proteolysis peptides for which a mass spectrometric signal ratio is determined at step c) may vary from 1 to 8, which encompasses 1, 2, 3, 4, 5, 6, 7 and 8 selected proteolysis peptides.

In the embodiments wherein anti-TNF antibodies are quantified and wherein a labeled counterpart of Adalimumab is used as an Internal Standard compound wherein two selected proteolysis peptides are monitored, these may be selected in a group comprising SEQ ID NO. 16 and 17; SEQ ID NO. 16 and 18; SEQ ID NO. 16 and 19; SEQ ID NO. 16 and 20; SEQ ID NO. 16 and 21; SEQ ID NO. 16 and 22; SEQ ID NO. 16 and 23; SEQ ID NO. 17 and 18; SEQ ID NO. 17 and 19; SEQ ID NO. 17 and 20; SEQ ID NO. 17 and 21; SEQ ID NO. 17 and 22; SEQ ID NO. 17 and 23; SEQ ID NO. 18 and 19; SEQ ID NO. 18 and 20; SEQ ID NO. 18 and 21; SEQ ID NO. 18 and 22; SEQ ID NO. 18 and 23; SEQ ID NO. 19 and 20; SEQ ID NO. 19 and 21; SEQ ID NO. 19 and 22; SEQ ID NO. 19 and 23; SEQ ID NO. 20 and 21; SEQ ID NO. 20 and 22; SEQ ID NO. 20 and 23; SEQ ID NO. 21 and 22; and SEQ ID NO. 22 and 23.

In the embodiments wherein anti-TNF antibodies are quantified and wherein a labeled counterpart of Adalimumab is used as an Internal Standard compound wherein three selected proteolysis peptides are monitored, these may be selected in a group comprising SEQ ID NO. 16, 17 and 18; SEQ ID NO. 16, 17 and 19; SEQ ID NO. 16, 17 and 20; SEQ ID NO. 16, 17 and 21; SEQ ID NO. 16, 17 and 22; SEQ ID NO. 16, 17 and 23; SEQ ID NO. 16, 18 and 19; SEQ ID NO. 16, 18 and 20; SEQ ID NO. 16, 18 and 21; SEQ ID NO. 16; 18 and 22; SEQ ID NO. 16, 18 and 23; SEQ ID NO. 16, 19 and 20; SEQ ID NO. 16, 19 and 21; SEQ ID NO. 16, 19 and 22; SEQ ID NO. 16; 19 and 23; SEQ ID NO. 16; 20 and 21; SEQ ID NO. 16, 20 and 22; SEQ ID NO. 16, 20 and 23; SEQ ID NO. 16; 21 and 22; SEQ ID NO. 16, 21 and 23; SEQ ID NO. 16, 22 and 23; SEQ ID NO. 17, 18 and 19; SEQ ID NO. 17, 18 and 20; SEQ ID NO. 17, 18 and 21; SEQ ID NO. 17, 18 and 22; SEQ ID NO. 17, 18 and 23; SEQ ID NO. 17, 19 and 20; SEQ ID NO. 17, 19 and 21; SEQ ID NO. 17, 19 and 22; SEQ ID NO. 17, 19 and 23; SEQ ID NO. 17, 20 and 21; SEQ ID NO. 17, 20 and 22; SEQ ID NO. 17, 20 and 23; SEQ ID NO. 17, 21 and 22; SEQ ID NO. 17, 21 and 23; SEQ ID NO. 17, 22 and 23; SEQ ID NO. 18, 19, and 20; SEQ ID NO. 18, 19 and 21; SEQ ID NO. 18, 19 and 22; SEQ ID NO. 18, 19 and 23; SEQ ID NO. 18, 20 and 21, SEQ ID NO. 18, 20 and 22; SEQ ID NO. 18, 20 and 23; SEQ ID NO. 18, 21 and 22; SEQ ID NO. 18, 21 and 23, SEQ ID NO. 18, 22 and 23; SEQ ID NO. 19, 20 and 21; SEQ ID NO. 19, 20 and 22; SEQ ID NO. 19, 20 and 23; SEQ ID NO. 19, 21 and 22; SEQ ID NO. 19, 21 and 23; SEQ ID NO. 19, 22 and 23; SEQ ID NO. 20, 21 and 22; SEQ ID NO. 20, 21 and 23; SEQ ID NO. 20, 22 and 23; SEQ ID NO. 21, 22 and 23.

In the embodiments wherein anti-TNF antibodies are quantified and wherein a labeled counterpart of Adalimumab is used as an Internal Standard compound wherein four selected proteolysis peptides are monitored, these may be selected in a group comprising SEQ ID NO. 16, 17, 18 and 19; SEQ ID NO. 16, 17 18 and 20; SEQ ID NO. 16, 17, 18, and 21; SEQ ID NO. 16, 17, 18 and 22; SEQ ID NO. 16, 17, 18 and 23; SEQ ID NO. 16, 18, 19 and 20; SEQ ID NO. 16, 18, 19 and 21; SEQ ID NO. 16, 18, 19 and 22; SEQ ID NO. 16, 18, 19 and 23; SEQ ID NO. 16, 19, 20 and 21; SEQ ID NO. 16, 19, 20 and 22; SEQ ID NO. 16, 19, 20 and 23; SEQ ID NO. 16, 20, 21 and 22; SEQ ID NO. 16, 20, 21 and 23; SEQ ID NO. 16, 20, 22 and 23; SEQ ID NO. 17, 18, 19 and 20; SEQ ID NO. 17, 18, 19 and 21; SEQ ID NO. 17, 18, 19 and 22; SEQ ID NO. 17, 18, 19 and 23; SEQ ID NO. 17, 19, 20 and 21; SEQ ID NO. 17, 19, 20 and 22; SEQ ID NO. 17, 19, 20 and 23; SEQ ID NO. 17, 20, 21 and 22; SEQ ID NO. 17, 20, 21 and 23; SEQ ID NO. 17, 21, 22 and 23; SEQ ID NO. 18, 19, 20 and 21; SEQ ID NO. 18, 19, 20 and 22; SEQ ID NO. 18, 19, 20 and 23; SEQ ID NO. 18, 20, 21 and 22; SEQ ID NO. 18, 20, 22 and 23; SEQ ID NO. 18, 21, 22 and 23; SEQ ID NO. 19, 20, 21 and 22; SEQ ID NO. 19, 20, 21 and 23; SEQ ID NO. 19, 21, 22 and 23; SEQ ID NO. 20, 21, 22 and 23.

In the embodiments wherein anti-TNF antibodies are quantified and wherein a labeled counterpart of Adalimumab is used as an Internal Standard compound wherein five selected proteolysis peptides are monitored, these may be selected in a group comprising SEQ ID NO. 16, 17, 18, 19 and 20; SEQ ID NO. 16, 17, 18, 19, and 21; SEQ ID NO. 16, 17, 18, 19 and 22; SEQ ID NO. 16, 17, 18, 19 and 23; SEQ ID NO. 16, 18, 19, 20 and 21; SEQ ID NO. 16, 18, 19, 20 and 22; SEQ ID NO. 16, 18, 19, 20 and 23; SEQ ID NO. 16, 19, 20, 21 and 22; SEQ ID NO. 16, 19, 20, 21 and 23; SEQ ID NO. 16, 20, 21, 22 and 23; SEQ ID NO. 17, 18, 19, 20 and 21; SEQ ID NO. 17, 18, 19, 20 and 22; SEQ ID NO. 17, 18, 19, 20 and 23; SEQ ID NO. 17, 19, 20, 21 and 22; SEQ ID NO. 17, 19, 20, 21 and 23; SEQ ID NO. 17, 20, 21, 22 and 23; SEQ ID NO. 18, 19, 20, 21 and 22; SEQ ID NO. 18, 19, 20, 21 and 23; SEQ ID NO. 18, 20, 21, 22 and 23; SEQ ID NO. 19, 20, 21, 22 and 23.

In the embodiments wherein anti-TNF antibodies are quantified and wherein a labeled counterpart of Adalimumab is used as an Internal Standard compound wherein six selected proteolysis peptides are monitored, these may be selected in a group comprising SEQ ID NO. 16, 17, 18, 19, 20 and 21; SEQ ID NO. 16, 17, 18, 19, 20 and 22, SEQ ID NO. 16, 17, 18, 19, 20 and 23; SEQ ID NO. 16, 18, 19, 20, 21 and 22; SEQ ID NO. 16, 18, 19, 20, 21 and 23; SEQ ID NO. 16, 19, 20, 21, 22 and 23; SEQ ID NO. 17, 18, 19, 20, 21 and 22; SEQ ID NO. 17, 18, 19, 20, 21 and 23; SEQ ID NO. 17, 19, 20, 21, 22 and 23; SEQ ID NO. 18, 19, 20, 21, 22 and 23;

In the embodiments wherein anti-TNF antibodies are quantified and wherein a labeled counterpart of Adalimumab is used as an Internal Standard compound wherein seven selected proteolysis peptides are monitored, these may be selected in a group comprising SEQ ID NO. 16, 17, 18, 19, 20, 21 and 22; SEQ ID NO. 16, 17, 18, 19, 20, 21 and 23; SEQ ID NO. 16, 18, 19, 20, 21, 22 and 23; SEQ ID NO. 17, 18, 19, 20, 21, 22 and 23.

In the embodiments wherein eight selected proteolysis peptides are monitored, these may be selected in a group comprising SEQ ID NO. 16, 17, 18, 19, 20, 21, 22 and 23.

In the embodiments wherein the proteolysis step is performed by using trypsin or a trypsin-containing protease composition and wherein a labeled counterpart of Certolizumab is used as an Internal Standard compound, the number of selected proteolysis peptides for which a mass spectrometric signal ratio is determined at step c) may vary from 1 to 7, which encompasses 1, 2, 3, 4, 5, 6 and 7 selected proteolysis peptides.

In the embodiments wherein anti-TNF antibodies are quantified and wherein a labeled counterpart of Certolizumab is used as an Internal Standard compound wherein two selected proteolysis peptides are monitored, these may be selected in a group comprising SEQ ID NO. 24 and 25; SEQ ID NO. 24 and 26; SEQ ID NO. 24 and 27; SEQ ID NO. 24 and 28; SEQ ID NO. 24 and 29; SEQ ID NO. 24 and 30; SEQ ID NO. 25 and 26; SEQ ID NO. 25 and 27; SEQ ID NO. 25 and 28; SEQ ID NO. 25 and 29; SEQ ID NO. 25 and 30; SEQ ID NO. 26 and 27; SEQ ID NO. 26 and 28; SEQ ID NO. 26 and 29; SEQ ID NO. 26 and 30; SEQ ID NO. 27 and 28; SEQ ID NO. 27 and 29; SEQ ID NO. 27 and 30; SEQ ID NO. 28 and 29; SEQ ID NO. 28 and 30; SEQ ID NO. 29 and 30.

In the embodiments wherein anti-TNF antibodies are quantified and wherein a labeled counterpart of Certolizumab is used as an Internal Standard compound wherein three selected proteolysis peptides are monitored, these may be selected in a group comprising SEQ ID NO. 24, 25 and 26; SEQ ID NO. 24, 25 and 27; SEQ ID NO. 24, 25 and 28; SEQ ID NO. 24, 25 and 29; SEQ ID NO. 24, 25 and 30; SEQ ID NO. 24, 26 and 27; SEQ ID NO. 24, 26 and 28; SEQ ID NO. 24, 26 and 29; SEQ ID NO. 24, 26 and 30; SEQ ID NO. 24, 27 and 28; SEQ ID NO. 24, 27 and 29; SEQ ID NO. 24, 27 and 30; SEQ ID NO. 24; 28 and 29; SEQ ID NO. 24, 28 and 30; SEQ ID NO. 24; 29 and 30; SEQ ID NO. 25, 26 and 27; SEQ ID NO. 25, 26 and 28; SEQ ID NO. 25, 26 and 29; SEQ ID NO. 25, 26 and 30; SEQ ID NO. 25, 27 and 28; SEQ ID NO. 25, 27 and 29; SEQ ID NO. 25, 27 and 30; SEQ ID NO. 25, 28 and 29; SEQ ID NO. 25, 28 and 30; SEQ ID NO. 25, 29 and 30; SEQ ID NO. 26, 27, and 28; SEQ ID NO. 26, 27 and 29; SEQ ID NO. 26, 27 and 30; SEQ ID NO. 26, 28 and 29; SEQ ID NO. 26, 28 and 30; SEQ ID NO. 26, 29 and 30; SEQ ID NO. 27, 28 and 29; SEQ ID NO. 27, 28 and 30; SEQ ID NO. 28, 29 and 30.

In the embodiments wherein anti-TNF antibodies are quantified and wherein a labeled counterpart of Certolizumab is used as an Internal Standard compound wherein four selected proteolysis peptides are monitored, these may be selected in a group comprising SEQ ID NO. 24, 25, 26 and 27; SEQ ID NO. 24, 25 26 and 28; SEQ ID NO. 24, 25, 26, and 29; SEQ ID NO. 24, 25, 26 and 30; SEQ ID NO. 24, 26, 27 and 28; SEQ ID NO. 24, 26, 27 and 29; SEQ ID NO. 24, 26, 27 and 30; SEQ ID NO. 24, 27, 28 and 29; SEQ ID NO. 24, 27, 28 and 30; SEQ ID NO. 24, 28, 29 and 30; SEQ ID NO. 25, 26, 27 and 28; SEQ ID NO. 25, 26, 27 and 29; SEQ ID NO. 25, 26, 27 and 30; SEQ ID NO. 25, 27, 28 and 29; SEQ ID NO. 25, 27, 28 and 30; SEQ ID NO. 25, 28, 29 and 30; SEQ ID NO. 26, 27, 28 and 29; SEQ ID NO. 26, 27, 28 and 30; SEQ ID NO. 26, 28, 29 and 30; SEQ ID NO. 27, 28, 29 and 30.

In the embodiments wherein anti-TNF antibodies are quantified and wherein a labeled counterpart of Certolizumab is used as an Internal Standard compound wherein five selected proteolysis peptides are monitored, these may be selected in a group comprising SEQ ID NO. 24, 25, 26, 27 and 28; SEQ ID NO. 24, 25, 26, 27, and 29; SEQ ID NO. 24, 25, 26, 27 and 30; SEQ ID NO. 24, 26, 27, 28 and 29; SEQ ID NO. 24, 26, 27, 28 and 30; SEQ ID NO. 24, 27, 28, 29 and 30; SEQ ID NO. 25, 26, 27, 28 and 29; SEQ ID NO. 25, 26, 27, 28 and 30; SEQ ID NO. 25, 27, 28, 29 and 30; SEQ ID NO. 26, 27, 28, 29 and 30.

In the embodiments wherein anti-TNF antibodies are quantified and wherein a labeled counterpart of Certolizumab is used as an Internal Standard compound wherein six selected proteolysis peptides are monitored, these may be selected in a group comprising SEQ ID NO. 24, 25, 26, 27, 28 and 29; SEQ ID NO. 24, 25, 26, 27, 28 and 30, SEQ ID NO. 24, 26, 27, 28, 29 and 30; SEQ ID NO. 25, 26, 27, 28, 29 and 30.

In the embodiments wherein seven selected proteolysis peptides are monitored, these may be selected in a group comprising SEQ ID NO. 24, 25, 26, 27, 28, 29 and 30.

In the embodiments wherein the proteolysis step is performed by using trypsin or a trypsin-containing protease composition and wherein a labeled counterpart of Golimumab is used as an Internal Standard compound, the number of selected proteolysis peptides for which a mass spectrometric signal ratio is determined at step c) may vary from 1 to 7, which encompasses 1, 2, 3, 4, 5, 6 and 7 selected proteolysis peptides.

In the embodiments wherein anti-TNF antibodies are quantified and wherein a labeled counterpart of Golimumab is used as an Internal Standard compound wherein two selected proteolysis peptides are monitored, these may be selected in a group comprising SEQ ID NO. 31 and 32; SEQ ID NO. 31 and 33; SEQ ID NO. 31 and 34; SEQ ID NO. 31 and 35; SEQ ID NO. 31 and 36; SEQ ID NO. 31 and 37; SEQ ID NO. 32 and 33; SEQ ID NO. 32 and 34; SEQ ID NO. 32 and 35; SEQ ID NO. 32 and 36; SEQ ID NO. 32 and 37; SEQ ID NO. 33 and 34; SEQ ID NO. 33 and 35; SEQ ID NO. 33 and 36; SEQ ID NO. 33 and 37; SEQ ID NO. 34 and 35; SEQ ID NO. 34 and 36; SEQ ID NO. 34 and 37; SEQ ID NO. 35 and 36; SEQ ID NO. 35 and 37; SEQ ID NO. 36 and 37.

In the embodiments wherein anti-TNF antibodies are quantified and wherein a labeled counterpart of Golimumab is used as an Internal Standard compound wherein three selected proteolysis peptides are monitored, these may be selected in a group comprising SEQ ID NO. 31, 32 and 33; SEQ ID NO. 31, 32 and 34; SEQ ID NO. 31, 32 and 35; SEQ ID NO. 31, 32 and 36; SEQ ID NO. 31, 32 and 37; SEQ ID NO. 31, 33 and 34; SEQ ID NO. 31, 33 and 35; SEQ ID NO. 31, 33 and 36; SEQ ID NO. 31, 33 and 37; SEQ ID NO. 31, 34 and 35; SEQ ID NO. 31, 34 and 36; SEQ ID NO. 31, 34 and 37; SEQ ID NO. 31; 35 and 36; SEQ ID NO. 31, 35 and 37; SEQ ID NO. 31; 36 and 37; SEQ ID NO. 32, 33 and 34; SEQ ID NO. 32, 33 and 35; SEQ ID NO. 32, 33 and 36; SEQ ID NO. 32, 33 and 37; SEQ ID NO. 32, 34 and 35; SEQ ID NO. 32, 34 and 36; SEQ ID NO. 32, 34 and 37; SEQ ID NO. 32, 35 and 36; SEQ ID NO. 32, 35 and 37; SEQ ID NO. 32, 36 and 37; SEQ ID NO. 33, 34, and 35; SEQ ID NO. 33, 34 and 36; SEQ ID NO. 33, 34 and 37; SEQ ID NO. 33, 35 and 36; SEQ ID NO. 33, 35 and 37; SEQ ID NO. 33, 36 and 37; SEQ ID NO. 34, 35 and 36; SEQ ID NO. 34, 35 and 37; SEQ ID NO. 35, 36 and 37.

In the embodiments wherein anti-TNF antibodies are quantified and wherein a labeled counterpart of Golimumab is used as an Internal Standard compound wherein four selected proteolysis peptides are monitored, these may be selected in a group comprising SEQ ID NO. 31, 32, 33 and 34; SEQ ID NO. 31, 32 33 and 35; SEQ ID NO. 31, 32, 33, and 36; SEQ ID NO. 31, 32, 33 and 37; SEQ ID NO. 31, 33, 34 and 35; SEQ ID NO. 31, 33, 34 and 36; SEQ ID NO. 31, 33, 34 and 37; SEQ ID NO. 31, 34, 35 and 36; SEQ ID NO. 31, 34, 35 and 37; SEQ ID NO. 31, 35, 36 and 37; SEQ ID NO. 32, 33, 34 and 35; SEQ ID NO. 32, 33, 34 and 36; SEQ ID NO. 32, 33, 34 and 37; SEQ ID NO. 32, 34, 35 and 36; SEQ ID NO. 32, 34, 35 and 37; SEQ ID NO. 32, 35, 36 and 37; SEQ ID NO. 33, 34, 35 and 36; SEQ ID NO. 33, 34, 35 and 37; SEQ ID NO. 33, 35, 36 and 37; SEQ ID NO. 34, 35, 36 and 37.

In the embodiments wherein anti-TNF antibodies are quantified and wherein a labeled counterpart of Golimumab is used as an Internal Standard compound wherein five selected proteolysis peptides are monitored, these may be selected in a group comprising SEQ ID NO. 31, 32, 33, 34 and 35; SEQ ID NO. 31, 32, 33, 34, and 36; SEQ ID NO. 31, 32, 33, 34 and 37; SEQ ID NO. 31, 33, 34, 35 and 36; SEQ ID NO. 31, 33, 34, 35 and 37; SEQ ID NO. 31, 34, 35, 36 and 37; SEQ ID NO. 32, 33, 34, 35 and 36; SEQ ID NO. 32, 33, 34, 35 and 37; SEQ ID NO. 32, 34, 35, 36 and 37; SEQ ID NO. 33, 34, 35, 36 and 37.

In the embodiments wherein anti-TNF antibodies are quantified and wherein a labeled counterpart of Golimumab is used as an Internal Standard compound wherein six selected proteolysis peptides are monitored, these may be selected in a group comprising SEQ ID NO. 31, 32, 33, 34, 35 and 36; SEQ ID NO. 31, 32, 33, 34, 35 and 37, SEQ ID NO. 31, 33, 34, 35, 36 and 37; SEQ ID NO. 32, 33, 34, 35, 36 and 37.

In the embodiments wherein seven selected proteolysis peptides are monitored, these may be selected in a group comprising SEQ ID NO. 31, 32, 33, 34, 35, 36 and 37.

In the embodiments wherein the proteolysis step is performed by using trypsin or a trypsin-containing protease composition wherein anti-cancer antibodies are quantified and wherein a labeled counterpart of Trastuzumab is used as an Internal Standard compound, the number of selected proteolysis peptides for which a mass spectrometric signal ratio is determined at step c) may vary according notably to of the number of available proteolysis peptides. The number of selected proteolysis peptides for which a mass spectrometric signal ratio is determined at step c) may vary from 1 to 7 proteolysis peptides, depending from the number of proteolysis peptides which are available, which encompasses 1, 2, 3, 4, 5, 6, and 7 selected proteolysis peptides.

In the embodiments wherein the proteolysis step is performed by using trypsin or a trypsin-containing protease composition wherein anti-cancer antibodies are quantified and wherein a labeled counterpart of Trastuzumab is used as an Internal Standard compound and wherein two selected proteolysis peptides are monitored, these may be selected in a group comprising SEQ ID NO. 48 and 49, SEQ ID NO. 48 and 50, SEQ ID NO. 48 and 51, SEQ ID NO. 48 and 52, SEQ ID NO. 48 and 53, SEQ ID NO. 49 and 50, SEQ ID NO. 49 and 51, SEQ ID NO. 49 and 52, SEQ ID NO. 49 and 53, SEQ ID NO. 50 and 51, SEQ ID NO. 50 and 52, SEQ ID NO. 50 and 53, SEQ ID NO. 51 and 52, SEQ ID NO. 51 and 53, and SEQ ID NO. 52 and 53.

In the embodiments wherein the proteolysis step is performed by using trypsin or a trypsin-containing protease composition wherein anti-cancer antibodies are quantified and wherein a labeled counterpart of Trastuzumab is used as an Internal Standard compound and wherein three selected proteolysis peptides are monitored, these may be selected in a group comprising SEQ ID NO. 48, 49 and 50; SEQ ID NO. 48, 49 and 51; SEQ ID NO. 48, 49 and 52; SEQ ID NO. 48, 49 and 53; SEQ ID NO. 48, 50 and 51; SEQ ID NO. 48, 50 and 52; SEQ ID NO. 48, 50 and 53; SEQ ID NO. 48, 51 and 52; SEQ ID NO. 48, 51 and 53; SEQ ID NO. 48; 52 and 53; SEQ ID NO. 49, 50 and 51; SEQ ID NO. 49, 50 and 52; SEQ ID NO. 49, 50 and 53; SEQ ID NO. 49, 51 and 52; SEQ ID NO. 49, 51 and 53; SEQ ID NO. 49, 52 and 53; SEQ ID NO. 50, 51, and 52; SEQ ID NO. 50, 51 and 53; SEQ ID NO. 50, 52 and 53, SEQ ID NO. 51, 52 and 53.

In the embodiments wherein the proteolysis step is performed by using trypsin or a trypsin-containing protease composition wherein anti-cancer antibodies are quantified and wherein a labeled counterpart of Trastuzumab is used as an Internal Standard compound and wherein four selected proteolysis peptides are monitored, these may be selected in a group comprising SEQ ID NO. 48, 49, 50 and 51; SEQ ID NO. 48, 49, 50 and 52; SEQ ID NO. 48, 49, 50, and 53; SEQ ID NO. 48, 50, 51 and 52; SEQ ID NO. 48, 50, 51 and 53; SEQ ID NO. 48, 50, 52 and 53; SEQ ID NO. 48, 51, 52 and 53; SEQ ID NO. 49, 50, 51 and 52; SEQ ID NO. 49, 50, 51 and 53; SEQ ID NO. 49, 50, 52 and 53; SEQ ID NO. 49, 51, 52 and 53; SEQ ID NO. 50, 51, 52 and 53.

In the embodiments wherein the proteolysis step is performed by using trypsin or a trypsin-containing protease composition wherein anti-cancer antibodies are quantified and wherein a labeled counterpart of Trastuzumab is used as an Internal Standard compound and wherein five selected proteolysis peptides are monitored, these may be selected in a group comprising SEQ ID NO. 48, 49, 50, 51 and 52; SEQ ID NO. 48, 49, 50, 51 and 53; SEQ ID NO 48, 49, 50, 52 and 53; SEQ ID NO 48, 49, 51, 52 and 53; SEQ ID NO. 48, 50, 51, 52 and 53; SEQ ID NO 49, 50, 51, 52, and 53.

In the embodiments wherein the proteolysis step is performed by using trypsin or a trypsin-containing protease composition wherein anti-cancer antibodies are quantified and wherein a labeled counterpart of Rituximab is used as an Internal Standard compound, the number of selected proteolysis peptides for which a mass spectrometric signal ratio is determined at step c) may vary according notably to of the number of available proteolysis peptides. The number of selected proteolysis peptides for which a mass spectrometric signal ratio is determined at step c) may vary from 1 to 10 proteolysis peptides, depending from the number of proteolysis peptides which are available, which encompasses 1, 2, 3, 4, 5, 6, 7, 8, 9 and 10 selected proteolysis peptides.

In the embodiments wherein the proteolysis step is performed by using trypsin or a trypsin-containing protease composition wherein anti-cancer antibodies are quantified and wherein a labeled counterpart of Rituximab is used as an Internal Standard compound and wherein two selected proteolysis peptides are monitored, these may be selected in a group comprising SEQ ID NO. 54 and 55, SEQ ID NO. 54 and 56, SEQ ID NO. 54 and 57, SEQ ID NO. 54 and 58, SEQ ID NO. 54 and 59, SEQ ID NO. 54 and 60, SEQ ID NO. 54 and 61, SEQ ID NO. 54 and 62, SEQ ID NO. 54 and 63, SEQ ID NO. 54 and 64, SEQ ID NO. 55 and 56, SEQ ID NO. 55 and 57, SEQ ID NO. 55 and 58, SEQ ID NO. 55 and 59, SEQ ID NO. 55 and 60, SEQ ID NO. 55 and 61, SEQ ID NO. 55 and 62, SEQ ID NO. 55 and 63, SEQ ID NO. 55 and 64, SEQ ID NO. 56 and 57, SEQ ID NO. 56 and 58, SEQ ID NO. 56 and 59, SEQ ID NO. 56 and 59, SEQ ID NO. 56 and 60, SEQ ID NO. 56 and 61, SEQ ID NO. 56 and 62, SEQ ID NO. 56 and 63, SEQ ID NO. 56 and 64, SEQ ID NO. 57 and 58, SEQ ID NO. 57 and 59, SEQ ID NO. 57 and 60, SEQ ID NO. 57 and 61, SEQ ID NO. 57 and 62, SEQ ID NO. 57 and 63, SEQ ID NO. 57 and 64, SEQ ID NO. 58 and 59, SEQ ID NO. 58 and 60, SEQ ID NO. 58 and 61, SEQ ID NO. 58 and 62, SEQ ID NO. 58 and 63, SEQ ID NO. 58 and 64, SEQ ID NO. 59 and 60, SEQ ID NO. 59 and 61, SEQ ID NO. 59 and 62, SEQ ID NO. 59 and 63, SEQ ID NO. 59 and 64, SEQ ID NO. 60 and 61, SEQ ID NO. 60 and 62, SEQ ID NO. 60 and 63, SEQ ID NO. 60 and 64, SEQ ID NO. 61 and 62, SEQ ID NO. 61 and 63, SEQ ID NO. 61 and 64, SEQ ID NO. 62 and 63, SEQ ID NO. 63 and 64.

In the embodiments wherein the proteolysis step is performed by using trypsin or a trypsin-containing protease composition wherein anti-cancer antibodies are quantified and wherein a labeled counterpart of Rituximab is used as an Internal Standard compound and wherein three selected proteolysis peptides are monitored, these may be selected in a group comprising SEQ ID NO. 54, 55 and 56; SEQ ID NO. 54, 55 and 57; SEQ ID NO. 54, 55 and 58; SEQ ID NO. 54, 55 and 59; SEQ ID NO. 54, 55 and 60; SEQ ID NO. 54, 55 and 61; SEQ ID NO. 54, 55 and 62; SEQ ID NO. 54, 55 and 63; SEQ ID NO. 54, 55 and 64; SEQ ID NO. 54, 56 and 57; SEQ ID NO. 54, 56 and 58; SEQ ID NO. 54, 56 and 59; SEQ ID NO. 54; 56 and 60; SEQ ID NO. 54, 56 and 61; SEQ ID NO. 54, 56 and 62; SEQ ID NO. 54, 56 and 63; SEQ ID NO. 54, 56 and 64; SEQ ID NO. 54, 57 and 58; SEQ ID NO. 54, 57 and 59; SEQ ID NO. 54, 57 and 60; SEQ ID NO. 54; 57 and 61; SEQ ID NO. 54; 57 and 62; SEQ ID NO. 54; 57 and 63; SEQ ID NO. 54; 57 and 64; SEQ ID NO. 54; 58 and 59; SEQ ID NO. 54, 58 and 60; SEQ ID NO. 54, 58 and 61; SEQ ID NO. 54, 58 and 62; SEQ ID NO. 54, 58 and 63; SEQ ID NO. 54, 58 and 64; SEQ ID NO. 54; 59 and 60; SEQ ID NO. 54, 59 and 61; SEQ ID NO. 54, 59 and 62; SEQ ID NO. 54, 59 and 63; SEQ ID NO. 54, 59 and 64; SEQ ID NO. 54, 60 and 61; SEQ ID NO. 54, 60 and 62; SEQ ID NO. 54, 60 and 63; SEQ ID NO. 54, 60 and 64; SEQ ID NO. 54, 61 and 62; SEQ ID NO. 54, 51 and 63; SEQ ID NO. 54, 61 and 64; SEQ ID NO. 55, 56 and 57; SEQ ID NO. 55, 56 and 58; SEQ ID NO. 55, 56 and 59; SEQ ID NO. 55, 56 and 60; SEQ ID NO. 55, 56 and 61; SEQ ID NO. 55, 56 and 62; SEQ ID NO. 55, 56 and 63; SEQ ID NO. 55, 56 and 64; SEQ ID NO. 55, 57 and 58; SEQ ID NO. 55, 57 and 59; SEQ ID NO. 55, 57 and 60; SEQ ID NO. 55, 57 and 61; SEQ ID NO. 55, 58 and 59; SEQ ID NO. 55, 58 and 60; SEQ ID NO. 55, 58 and 61; SEQ ID NO. 55, 58 and 62; SEQ ID NO. 55, 58 and 63; SEQ ID NO. 55, 58 and 64; SEQ ID NO. 55, 58 and 59; SEQ ID NO. 55, 58 and 60; SEQ ID NO. 55, 58 and 61; SEQ ID NO. 55, 58 and 62; SEQ ID NO. 55, 58 and 63; SEQ ID NO. 55, 58 and 64; SEQ ID NO. 55, 59 and 60; SEQ ID NO. 55, 59 and 61; SEQ ID NO. 55, 59 and 62; SEQ ID NO. 55, 59 and 63; SEQ ID NO. 55, 59 and 64; SEQ ID NO. 55, 60 and 61; SEQ ID NO. 55, 60 and 62; SEQ ID NO. 55, 60 and 63; SEQ ID NO. 55, 60 and 64; SEQ ID NO. 55, 61 and 62; SEQ ID NO. 55, 61 and 63; SEQ ID NO. 55, 61 and 64; SEQ ID NO. 55, 62 and 63; SEQ ID NO. 55, 62 and 64; SEQ ID NO. 55, 63 and 64; SEQ ID NO. 56, 57, and 58; SEQ ID NO. 56, 57 and 59; SEQ ID NO. 56, 57 and 60; SEQ ID NO. 56, 57 and 61; SEQ ID NO. 56, 57 and 62; SEQ ID NO. 56, 57 and 63; SEQ ID NO. 56, 57 and 64; SEQ ID NO. 56, 58 and 59, SEQ ID NO. 56, 58 and 60; SEQ ID NO. 56, 58 and 61; SEQ ID NO. 56, 58 and 62; SEQ ID NO. 56, 58 and 63; SEQ ID NO. 56, 58 and 64; SEQ ID NO. 56, 59 and 60; SEQ ID NO. 56, 59 and 61; SEQ ID NO. 56, 59 and 62; SEQ ID NO. 56, 59 and 63; SEQ ID NO. 56, 59 and 64; SEQ ID NO. 56, 60 and 61; SEQ ID NO. 56, 60 and 62; SEQ ID NO. 56, 60 and 63; SEQ ID NO. 56, 60 and 64; SEQ ID NO. 56, 61 and 62; SEQ ID NO. 56, 61 and 63; SEQ ID NO. 56, 61 and 64; SEQ ID NO. 57, 58 and 59; SEQ ID NO. 57, 58 and 60; SEQ ID NO. 57, 58 and 61; SEQ ID NO. 57, 58 and 62; SEQ ID NO. 57, 58 and 63; SEQ ID NO. 57, 58 and 64; SEQ ID NO. 57, 59 and 60; SEQ ID NO. 57, 59 and 61; SEQ ID NO. 57, 59 and 62; SEQ ID NO. 57, 59 and 63; SEQ ID NO. 57, 59 and 64; SEQ ID NO. 57, 60 and 61; SEQ ID NO. 57, 60 and 62; SEQ ID NO. 57, 60 and 63; SEQ ID NO. 57, 60 and 64; SEQ ID NO. 57, 61 and 62; SEQ ID NO. 57, 61 and 63; SEQ ID NO. 57, 61 and 64; SEQ ID NO. 57, 62 and 63; SEQ ID NO. 57, 62 and 64; SEQ ID NO. 57, 63 and 64; SEQ ID NO. 58, 59 and 60; SEQ ID NO. 58, 59 and 61; SEQ ID NO. 58, 59 and 62; SEQ ID NO. 58, 59 and 63; SEQ ID NO. 58, 59 and 64; SEQ ID NO. 58, 60 and 61; SEQ ID NO. 59, 60 and 61; SEQ ID NO. 59, 60 and 62; SEQ ID NO. 59, 60 and 63; SEQ ID NO. 59, 60 and 64; SEQ ID NO. 58, 61 and 62; SEQ ID NO. 59, 61 and 63; SEQ ID NO. 59, 61 and 64; SEQ ID NO. 58, 62 and 63; SEQ ID NO. 59, 62 and 64; SEQ ID NO. 58, 63 and 64; SEQ ID NO. 59, 60 and 61; SEQ ID NO. 59, 60 and 62; SEQ ID NO. 59, 60 and 63; SEQ ID NO. 59, 60 and 64; SEQ ID NO. 59, 61 and 62; SEQ ID NO. 59, 61 and 63; SEQ ID NO. 59, 61 and 64; SEQ ID NO. 59, 62 and 63; SEQ ID NO. 59, 62 and 64; SEQ ID NO. 59, 63 and 64; SEQ ID NO. 60, 61 and 62; SEQ ID NO. 60, 61 and 63; SEQ ID NO. 60, 61 and 64; SEQ ID NO. 60, 62 and 63; SEQ ID NO. 60, 62 and 64; SEQ ID NO. 60, 63 and 64; SEQ ID NO. 61, 62 and 63; SEQ ID NO. 61, 62 and 64; SEQ ID NO. 61, 63 and 64; SEQ ID NO. 62, 63 and 64.

In the embodiments wherein the proteolysis step is performed by using trypsin or a trypsin-containing protease composition wherein anti-cancer antibodies are quantified and wherein a labeled counterpart of Bevacizumab is used as an Internal Standard compound, the number of selected proteolysis peptides for which a mass spectrometric signal ratio is determined at step c) may vary according notably to of the number of available proteolysis peptides. The number of selected proteolysis peptides for which a mass spectrometric signal ratio is determined at step c) may vary from 1 to 8 proteolysis peptides, depending from the number of proteolysis peptides which are available, which encompasses 1, 2, 3, 4, 5, 6, 7, and 8 selected proteolysis peptides.

In the embodiments wherein the proteolysis step is performed by using trypsin or a trypsin-containing protease composition wherein anti-cancer antibodies are quantified and wherein a labeled counterpart of Bevacizumab is used as an Internal Standard compound and wherein two selected proteolysis peptides are monitored, these may be selected in a group comprising SEQ ID NO. 65 and 66, SEQ ID NO. 65 and 67, SEQ ID NO. 65 and 68, 65 and 69, 65 and 70, 65 and 71, 65 and 72, 66 and 67, 66 and 68, 66 and 69, 66 and 70, SEQ ID NO. 66 and 71, SEQ ID NO. 66 and 72, SEQ ID NO. 67 and 68, SEQ ID NO. 67 and 69, SEQ ID NO. 67 and 70, SEQ ID NO. 67 and 71, SEQ ID NO. 67 and 72, SEQ ID NO. 68 and 69, SEQ ID NO. 68 and 70, SEQ ID NO. 68 and 71, SEQ ID NO. 68 and 72, SEQ ID NO. 69 and 70, SEQ ID NO. 69 and 71, SEQ ID NO. 69 and 72, SEQ ID NO. 70 and 71, SEQ ID NO. 71 and 72.

For performing the therapeutic antibodies quantification method of the invention wherein the proteolysis step b) makes use of a hinge-targeting protease, the one or more selected proteolysis peptides are selected in a group comprising:
  for Infliximab: peptides of SEQ ID NO. 38-39,
  for Etanercept: peptide of SEQ ID NO. 40,
  for Adalimumab: peptides of SEQ ID NO. 41-42,
  for Certolizumab: peptides of SEQ ID NO. 43-44, and
  for Golimumab: peptides of SEQ ID NO. 45-46

In some embodiments, wherein the proteolysis step is performed by using a hinge-targeting protease and wherein a labeled counterpart of Infliximab is used as an Internal Standard compound, the spectrometric signals of one or both of the selected proteolysis peptides of SEQ ID NO. 38-39 are determined.

In some embodiments, wherein the proteolysis step is performed by using a hinge-targeting protease and wherein a labeled counterpart of Etanercept is used as an Internal Standard compound, the spectrometric signals of the selected proteolysis peptides of SEQ ID NO. 40 are determined.

In some embodiments, wherein the proteolysis step is performed by using a hinge-targeting protease and wherein a labeled counterpart of Adalimumab is used as an Internal Standard compound, the spectrometric signals of one or both of the selected proteolysis peptides of SEQ ID NO. 41-42 are determined.

In some embodiments, wherein the proteolysis step is performed by using a hinge-targeting protease and wherein a labeled counterpart of Certolizumab is used as an Internal Standard compound, the spectrometric signals of one or both of the selected proteolysis peptides of SEQ ID NO. 43-44 are determined.

In some embodiments, wherein the proteolysis step is performed by using a hinge-targeting protease and wherein a labeled counterpart of Golimumab is used as an Internal Standard compound, the spectrometric signals of one or both of the selected proteolysis peptides of SEQ ID NO. 45-46 are determined.

SRM transitions of selected proteolytic peptides from the anti-TNF antibodies tested, of proteolytic labeled peptides from the two or more anti-TNF antibodies used as Internal Standard compounds are preferably established after comparing the fragmentation spectra obtained from pure solutions of each of these peptides, with in silico fragmentation spectra generated with a relevant available software tool, such as the software commercialized under the name Skyline™ by MacCoss Lab Software (USA) and the bioinformatics tool ESP Predictor available from Genepattern (Vincent A. Fusaro, D. R. Mani, Jill P. Mesirov & Steven A. Carr, Nature Biotechnology (2009) 27:190-198), available notably from the Broad Insitute (USA)

Preferably, at step d), quantification of anti-TNF antibodies is based on the ratio of the mean of the peak areas of specific SRM of a selected anti-TNF antibody and the mean of the peak areas of the Internal Standard selected surrogate labeled peptide.

More precisely, the amount of anti-TNF antibodies in the sample tested, e.g. the concentration of the said anti-TNF antibodies in the test sample, is determined by reporting the ratio value that is calculated at step d) for the said test sample to a calibration curve that was generated as previously described elsewhere in the present specification.

As shown in the examples, the quantification described herein allows linearity between the measured amount (e.g. concentration) of an anti-TNF antibody and the expected amount thereof.

Quantifying anti-TNF antibodies with the quantification method described herein allows a high quantification precision, a high quantification repeatability, as well as anti-TNF antibodies quantification over a wide range of amounts.

The anti-TNF antibodies quantification method according to the invention allows a linearity of the quantification measure from 1 µg/mL or less to 1000 µg/mL or more.

According to Food Drug Administration/European Medicines Agency (FDA/EMA) guidelines for bioanalytical method validation, it is thus shown herein that the antibodies quantification method according to the invention, in particular the anti-TNF antibodies quantification method according to the invention, is at the same time sufficiently sensitive and reproducible to quantify antibodies such as anti-TNF antibodies in human plasma samples. It may be referred to the guidelines "Guidance for Industry—Bioanalytical Method validation" from the US department of Health and Human Services—Food and Drug Administration (2001); and corresponding EMA Quality guidelines.

The present invention also relates to kits for quantifying therapeutic antibodies, in particular for performing the anti-TNF antibody quantification method that is described throughout the present specification.

Thus, the present invention also relates to kits comprising two or more stable Isotopically Labeled therapeutic antibodies; for quantifying therapeutic antibodies in a human individual or a sample of a human individual.

In some embodiments, a kit according to the invention comprises two or more Stable Isotopically Labeled anti-TNF antibodies, especially two or more Stable Isotopically Labeled anti-TNF antibodies selected in a group comprising Infliximab, Etanercept, Adalimumab, Certolizumab and Golimumab. The SIL antibodies may be contained in a kit according to the invention in any combination, especially in any of the combinations that are described elsewhere in the present specification.

In some embodiments, the said kit comprises two SIL anti-TNF antibodies selected in a group comprising Infliximab, Etanercept, Adalimumab, Certolizumab and Golimumab. In some embodiments, the said kit comprises three SIL anti-TNF antibodies selected in a group comprising Infliximab, Etanercept, Adalimumab, Certolizumab and Golimumab. In some embodiments, the said kit comprises four SIL anti-TNF antibodies selected in a group comprising Infliximab, Etanercept, Adalimumab, Certolizumab and Golimumab. In some embodiments, the said kit comprises five SIL anti-TNF antibodies selected in a group comprising Infliximab, Etanercept, Adalimumab, Certolizumab and Golimumab.

In some embodiments, the SIL antibodies contained in a kit according to the invention may be under the form of a liquid suspension. In some other embodiments, the SIL antibodies contained in a kit according to the invention may be in a lyophilized form.

In some embodiments, the said kit further comprises reagents required for performing the anti-TNF antibody quantification method described herein, such as an appropriate protease, especially a protease selected in a group comprising (i) trypsin or a trypsin-containing composition and (ii) a hinge-targeting protease.

In some embodiments, the said kit also comprises information providing the calibration curves for each of therapeutic antibodies contained therein.

In some embodiments, the said kit also comprises information providing the calibration curves for each of the anti-TNF antibodies contained therein.

In some embodiments, the said kit also comprises information providing the calibration curves for each of the anti-cancer antibodies contained therein.

In some embodiments, the said kit further comprises reagents required for performing the anti-TNF antibody quantification method described herein, such as an appropriate protease, especially a protease selected in a group comprising (i) trypsin or a trypsin-containing composition and (ii) a hinge-targeting protease.

The present invention is further illustrated, without being limited thereto, by the examples below.

EXAMPLES

A. Materials End Methods (Examples 1 and 2)
A.1. Test Sample Preparation

The test sample is a plasma sample or a serum sample that was previously collected from a patient to be tested.

Infliximab mAb PSAQ standard is spiked in the test sample at a final concentration which is preferably comprised between 5 µg/mL and 50 µg/ml, more preferably between 10 µg/mL and 25 µg/ml (ideally 20 µg/ml).

The sample volume used for the experiment is comprised between 5 µl and 1000 µl, more preferably between 10 µl and 100 µl, and ideally is 10 µl.

To 10 µl serum sample (up to 50 µl), add the labeled Infliximab standard at a concentration of 25 µg/ml (for example add 1 µl of a [250 ng/µl] solution). Add PBS 1× to obtain a final sample volume of 100 µl.

A.2. Non-Antibody Protein Depletion by Affinity Chromatography

According to this embodiment, depletion in non-antibody proteins is performed by using an affinity chromatography support onto which TNF alpha was immobilized. More precisely, according to this method, biotinylated TNF alpha is added to the previously spiked test sample so as to capture the TNF binding molecules that are present in the spiked test sample, which includes (i) the Stable Isotope Labeled (SIL) anti-TNF antibodies used as Internal Standards and (ii) the other anti-TNF antibodies that are possibly present in the test sample before spiking with the SIL anti-TNF antibodies.

Then, the resulting mixture is brought into contact with a chromatographic support onto which streptavidin was immobilized, so as to capture the biotinylated TNF alpha that is possibly complexed with labeled and possibly non-labeled anti-TNF antibodies.

Then, the anti-TNF antibodies are eluted from the chromatographic support for further processing.

This method may be termed MSIA (for Mass Spectrometry ImmunoAffinity).

Reagents and Specific Instruments

Novus I Finnpipette 12 channel, 20-300 µl (Thermo), Streptavidin MSIA DARTs (Thermo), Biotinylated TNF-α (ACRO biosystems), Remicade (Janssen Biologics), Phosphate Buffered Saline (Gibco LifeSciences), Ammonium hydroxide solution (SIGMA-Aldrich), Acetonitrile LC-MS Chromasolv (Sigma-Aldrich), Formic Acid Aristar (VWR), Mix EndoLysC/Trypsine PROMEGA.

Preparation of the Biotinylated TNF-Alpha Solution

Dissolve 2.5 µg of biotinylated TNF-alpha in 100 µl PBS.

MSIA Experiment

Program the following step on the MSIA program:

Load Streptavidin MSIA tips on the pipette.

For the following step, it is very important to avoid air bubbles into the resin. To avoid bubbles, adjust the stand and the pipette in order that tips will always dip in solution along the experiment.

Select step WASH and wash the tips with PBS1× (volume of PBS required=200 µl).

Select the step CAPTURE 1 and aspirate the biotinylated TNF-alpha solution.

Select the step WASH and rinse the tips with PBS1× (volume of PBS required=200 µl).

Repeat this step twice.

Select the step CAPTURE 2 and aspirate the serum sample solution.

Select the step WASH and rinse the tips with Ammonium hydroxide solution (volume required=200 µl). Repeat this step and then WASH with 200 mM Ultrapure Water. Repeat this step twice.

Select the step ELUTE and elute with 30% Acetonitrile/0.05% formic acid solution (minimum volume required=100 µl).

Recover the eluate in a low-adsorption tube and dry the sample with a speed-vacuum.

A.3. Step of Enzyme Proteolysis

The step of enzyme proteolysis may be performed according to a plurality of embodiments. In some embodiments, enzyme proteolysis is performed through a method comprising two steps of trypsin digestion, (i) a step of trypsin digestion in denaturing conditions followed by (ii) a step of trypsin digestion in non-denaturing conditions, which method is referred as "Option 1" hereafter. In some other embodiments, enzyme proteolysis is performed through a method comprising a step of trypsin digestion in non-denaturing conditions, which method is referred as "option 2" hereafter. In still other embodiments, enzyme proteolysis is performed by using a hinge-targeting protease such as ideS (Immunoglobulin Degrading Enzyme form *Streptococcus*), which method is referred as "option 3" hereafter.

Option 1: Two-Step Trypsin Digestion

Trypsin Digestion in Denaturing Conditions

After complete dry, add 10 µl of 4M Urea solution in the tube and vortex. Check the pH of the sample that should be >6. If not, adjust the pH to 7-8 with 0.5M Tris Base solution.

Add 2 µg of EndolysC from the mix ENdolysC/Tryspine (the amount of EndolysC added may vary between 0.2 and 4 µg)

Process to predigestion at 37° C. during 2H.

Trypsin Digestion in Non-Denaturing Conditions

Add 190 µl of a 25 mM ammonium bicarbonate solution in the tube, mix and add 2 µg of trypsine from the mix EndolysC/trypsine (again the amount of EndolysC added may vary between 0.2 and 4 µg). Process to digestion at 37° C. during 2-4 h or overnight if preferred.

Desalt and concentrate the sample with a C18-ziptip (Proteabio), eluate the ziptip, dry the eluate.

Prior to injection, resuspend the sample in 20 µl of a 2% Acetonitrile, 0.1% formic acid solution.

Inject the sample on the LC-MS instrument.

Option 2: One-Step Trypsin Digestion

After complete dry, add 10 µl of 25 mM ammonium bicarbonate solution in the tube and vortex. Check the pH of the sample that should be >6. If not, adjust the pH to 7-8 with 0.5M Tris Base solution. Add 2 µg of trypsine from the mix EndolysC/trypsine (again the amount of EndolysC added may vary between 0.2 and 4 µg). Process to digestion at 37° C. during 2-4 h or overnight if preferred.

Add formic acid in the sample to stop the digestion to obtain a final concentration of 0.1%.

Inject the sample on the LC-MS instrument.

Option 3: Protease Digestion with ideS

After complete dry, resuspend the sample in 10 mM sodium phosphate, 150 mM NaCl, pH 7.4 or similar with pH ranging from 6.0-8.0 and check the pH (Adjust with Tris Base if necessary).

Break off the bottom seal of the FragIT™ column (save the cap) and slightly open the lid ~90° counter clockwise.

Place the column in a 1.5-2 ml collection tube and centrifuge the column at 200×g for 1 min to remove storage solution.

Equilibrate the column by adding 300 µl cleavage buffer and centrifuge the column at 200×g for 1 min.

Repeat steps 5 and 6 two times.

Put on the bottom cap on the column.

Immediately add the sample to be cleaved in a volume of 100 µl at a maximal concentration of 5 mg/ml IgG in cleavage buffer. Seal the column with the top lid. Take care to fully suspend the media manually and make sure it is flowing in the column. Incubate the column by end-over-end mixing for 15 min in room temperature. The incubation time can be increased without over digestion of the IgG.

Remove the top lid and the bottom cap. Place the column in a 1.5-2 ml collection tube. Centrifuge the column at 1000×g for 1 min to elute the sample. For maximum recovery of the sample, repeat twice this step using 100 µl cleavage buffer. Centrifuge the column at 1000×g for 1 min to elute the sample. Pool all the elution fractions.

If required, use a C4 ziptip to desalt the sample or precipitate with cold acetone, dry and resuspend in 2% ACN, 0.1% FA buffer.

A.4. LC-MS Analysis of Samples Treated with Option 1 or Option 2 (Trypsin Digestion)

The following peptides of sequences of SEQ ID NO. 1 to 37 should be monitored in the LC-SRM assay.

These peptides should be monitored in their labeled and non-labeled forms (mass increment will be calculated according to the stable-isotopically labeled amino acid present in the peptide sequence). Potential chemical modifications affecting amino acids should also be taken into account as these modifications will modify the m/z of peptide ions and corresponding fragments.

A.5. LC-MS Analysis of Samples Treated with Option 3 (IDES Digestion)

The following peptides of sequences SEQ ID NO. 38 to 46 should be monitored in the LC-SRM assay.

These peptides should be monitored in their labeled and non-labeled forms (mass increment will be calculated according to the stable-isotopically labeled amino acid present in the peptide sequence). Potential chemical modifications affecting amino acids should also be taken into account as these modifications will modify the m/z of peptide ions and corresponding fragments.

B. Materials End Methods (Example 3)

B.1. Test Sample Preparation

The test sample is a plasma sample or a serum sample that was previously collected from a patient to be tested.

Trastuzumab mAb PSAQ standard is spiked in the test sample at a final concentration which is preferably comprised between 5 µg/mL and 50 µg/ml, more preferably between 10 µg/mL and 25 µg/ml (ideally 20 µg/ml).

The sample volume used for the experiment is comprised between 5 µl and 1000 µl, more preferably between 10 µl and 100 µl, and ideally is 10 µl.

To 10 µl serum sample (up to 50 µl), add the labeled Infliximab standard at a concentration of 25 µg/ml (for example add 1 µl of a [250 ng/µl] solution). Add PBS 1× to obtain a final sample volume of 500 µl.

B.2. Albumin Depletion Using an Albumin-Affinity Resin

According to this embodiment, the sample is depleted from the albumin using an albumin affinity resin, which is commercially available (Cibacron-blue 3GA agarose, Sigma-Aldrich). More precisely, according to this method, the albumin present in the test sample is removed specifically, while the other proteins remain in the supernatant, which includes (i) the Stable Isotope Labeled (SIL) therapeutic antibodies used as Internal Standards and (ii) the other therapeutic antibodies that are eventually present in the test sample before spiking with the SIL therapeutic antibodies. The supernatant, depleted from albumin, is recovered and potentially subjected to a reduction/alkylation treatment (see section B.3). Before proceeding to digestion, the remaining proteins contained in the sample are precipitated using 10 volumes of cold acetone.

B.3. Reduction/Alkylation Step

The sample is first subjected to a reduction step, which aims at reducing a disulfide bonds. TCEP (Tris(2-carboxyethyl) phosphine) is added to the sample at a final concentration of 10 mM. The sample is incubated at room temperature during 20 min. Iodoacetamide (extemporaneously prepared) is then added in the sample at a final concentration of 100 mM. The sample is then incubated in the dark, at room temperature, during 45 min. Then, the sample is subjected to acetone precipitation. If not, the remaining Iodoacetamide present in the sample may be quenched by adding TCEP.

Reagents and Specific Instruments

Cibacron-blue 3GA Agarose resin (Sigma-Aldrich), Herceptin (Roche), Phosphate Buffered Saline (Gibco Life-Sciences), Tris(2-carboxyethyl)phosphine (SIGMA-Aldrich), Iodoacetamide (Sigma-Aldrich), Acetone (Sigma-Aldrich), Urea 8M solution (Sigma-Aldrich), Acetonitrile LC-MS Chromasolv (Sigma-Aldrich), Formic Acid Aristar (VWR), Mix EndoLysC/Trypsine PROMEGA.

B.3. Step of Enzyme Proteolysis

The step of enzyme proteolysis may be performed according to a plurality of embodiments. In some embodiments, enzyme proteolysis is performed through a method comprising two steps of trypsin digestion, (i) a step of trypsin digestion in denaturing conditions followed by (ii) a step of trypsin digestion in non-denaturing conditions, which method is referred as "Option 1" hereafter. In some other embodiments, enzyme proteolysis is performed through a method comprising a step of trypsin digestion in non-denaturing conditions, which method is referred as "option 2" hereafter.

Option 1: Two-Step Trypsin Digestion

Trypsin Digestion in Denaturing Conditions

After complete dry, add 10 µl of 4M Urea solution in the tube and vortex. Check the pH of the sample that should be >6. If not, adjust the pH to 7-8 with 0.5M Tris Base solution.

Add 2 µg of EndolysC from the mix ENdolysC/Tryspin (the amount of EndolysC added may vary between 0.2 and 4 µg)

Process to predigestion at 37° C. during 2H.

Trypsin Digestion in Non-Denaturing Conditions

Add 190 µl of a 25 mM ammonium bicarbonate solution in the tube, mix and add 2 µg of trypsine from the mix EndolysC/trypsine (again the amount of EndolysC added may vary between 0.2 and 4 µg). Process to digestion at 37° C. during 2-4 h or overnight if preferred.

Desalt and concentrate the sample with a C18-ziptip (Proteabio), eluate the ziptip, dry the eluate.

Prior to injection, resuspend the sample in 20 µl of a 2% Acetonitrile, 0.1% formic acid solution.

Inject the sample on the LC-MS instrument.

Option 2: One-Step Trypsin Digestion

After complete dry, add 10 µl of 25 mM ammonium bicarbonate solution in the tube and vortex. Check the pH of the sample that should be >6. If not, adjust the pH to 7-8 with 0.5M Tris Base solution. Add 2 µg of trypsine from the mix EndolysC/trypsine (again the amount of EndolysC added may vary between 0.2 and 4 µg). Process to digestion at 37° C. during 2-4 h or overnight if preferred.

Add formic acid in the sample to stop the digestion to obtain a final concentration of 0.1%.

Inject the sample on the LC-MS instrument.

B.4. LC-MS Analysis of Samples Treated with Option 1 or Option 2 (Trypsin Digestion)

The following peptides of sequences of SEQ ID NO. 48 to 73 should be monitored in the LC-SRM assay.

These peptides should be monitored in their labeled and non-labeled forms (mass increment will be calculated according to the stable-isotopically labeled amino acid present in the peptide sequence). Potential chemical modifications affecting amino acids should also be taken into account as these modifications will modify the m/z of peptide ions and corresponding fragments.

Example 1: Assessment of a Titration Curve for the Quantification in Human Serum Samples of the Therapeutic Antibody Infliximab in the Presence of Two Other Anti-TNF Antibodies, Using a Sample Preparation Based on Immunocapture (MSIA Technology)

The objective of this experiment was to perform a titration curve in order to assess the performances of the stable-isotopically labelled (SIL) antibody standards and of the LC-MS/MS method.

In Example 1, a titration curve was performed by using (i) non-labeled anti-TNF antibodies as Internal Standard Compounds and (ii) SIL Infliximab as the anti-TNF antibody to be quantified. Indeed, the same experiment may be performed by using (i) SIL anti-TNF antibodies as Internal Standard compounds and (ii) a non-labeled Infliximab as the anti-TNF antibody to be quantified.

A) Protocol

A titration curve was generated, according to the following protocol 1) adding to a serum sample defined amount of therapeutic anti-TNF antibodies, Infliximab, Adalimumab and Etanercept and 2) adding an increasing amount of SIL Infliximab. Thus, it is called a reverse titration curve because the SIL Infliximab is quantified using the therapeutic Infliximab.

Such an experiment mimics a situation where a patient would have been treated with Infliximab and whose serum will be analyzed using our LC-MS/MS method and three anti-TNF standards.

To perform this experiment, therapeutic antibodies Adalimumab, Etanercept and Infliximab were obtained from collaborators. The SIL Infliximab was produced and purified according to the method previously described (Lebert et al., Bioanalysis, 2015). Samples were treated using materials and methods described in Section A. Samples were treated following the option 1 described in the Section A. The peptides of sequences of SEQ ID NO. 1 to 23 were monitored in the LC-SRM assay, in their labelled and non-labelled forms.

TABLE 1

Samples constituted and analyzed to evaluate the accuracy and precision of our LC-MS/MS method in a context where multiple anti-TNF are present in the sample.

| Point | 1 | 2 | 3 | 4 | 5 | Zero |
|---|---|---|---|---|---|---|
| Human serum treated | 10 µl | 10 µl | 10 µl | 10 µl | 10 µl | 10 µl |
| Therapeutic Infliximab | 20 µg/ml | 20 µg/ml | 20 µg/ml | 20 µg/ml | 20 µg/ml | 20 µg/ml |
| Therapeutic Adalimumab | 20 µg/ml | 20 µg/ml | 20 µg/ml | 20 µg/ml | 20 µg/ml | 20 µg/ml |
| Therapeutic Etanercept | 20 µg/ml | 20 µg/ml | 20 µg/ml | 20 µg/ml | 20 µg/ml | 20 µg/ml |
| SIL Infliximab | 1 µg/ml | 10 µg/ml | 20 µg/ml | 50 µg/ml | 100 µg/ml | 0 µg/ml |
| Final volume of the sample | 30 µl | 30 µl | 30 µl | 30 µl | 30 µl | 30 µl |

B) Experimental Results

Figure 1:
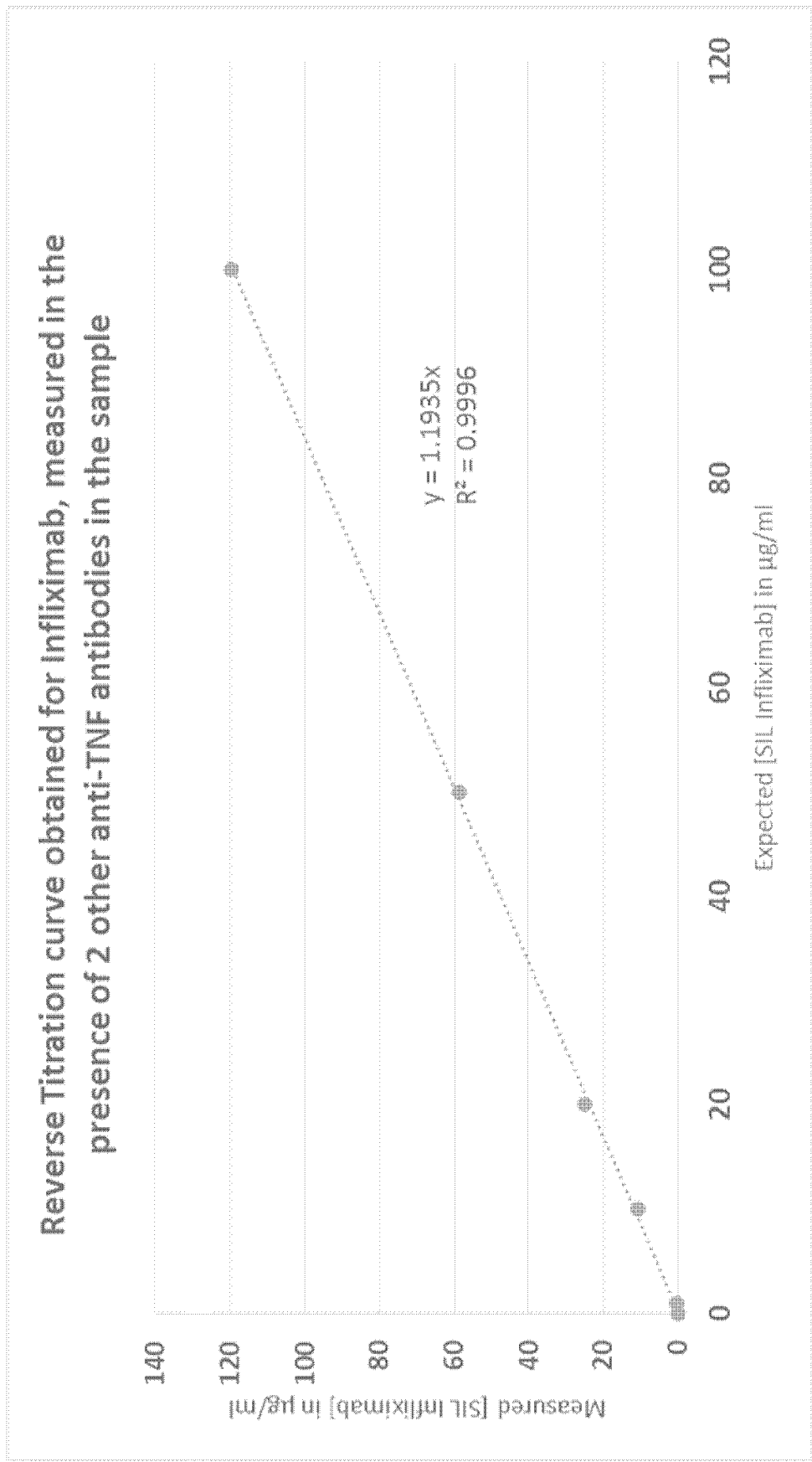
FIG. 1: Titration curve obtained for Infliximab, measured in the presence of two other anti-TNF antibodies in a test sample.

The quantification performances provided by our approach combining the use of mAb SIL standards and LC-MS/MS were assessed in a multiplex manner, where three different anti-TNF antibodies were simultaneously present in the human serum samples. For these tests, we have produced a reverse titration curve covering a concentration range between 1 µg/ml and 100 µg/ml. In this experiment, the accuracy obtained for 10 µg/ml and 100 µg/ml were below 20%. The results are depicted in FIG. 1. The mean regression equation was Y=1.19×X with a correlation coefficient $R^2$ of 0.999. For each concentration points, data obtained from the peptides monitored were consistent, indicating that our approach is robust. The accuracy was below 20% and fulfill the acceptance criteria. The high accuracy of the method demonstrates that it is possible to quantify with a high degree of precision a therapeutic anti-TNF antibody present in the blood of a patient using a generic and blinded approach, by combining the use of a SIL antibody standard and LC-MS.

Thus, the method can be applied for the personalized therapeutic follow-up of patients treated with anti-TNF therapeutic antibodies.

More interestingly, the experimental results show that the anti-TNF antibody quantification method described herein does not requires a selection of an antibody-specific quantification method as it is the case in the present usual practice. Moreover, the anti-TNF antibody quantification method allows correcting situations wherein a patient's treatment is erroneously documented, and also allows determining anti-TNF antibodies concentrations in test samples from patients which have undergone anti-TNF combination therapy treatments. Finally, the anti-TNF quantification method is not affected if the patient has received a first treatment with anti-TNF antibody and subsequently a second treatment with a second anti-TNF antibody distinct from the first antibody.

Example 2: Evaluation of the Maximum Concentration of Anti-TNF Antibodies which can be Present in the Sample without Affecting the Antigen-Capture Using MSIA The objective of this experiment was to evaluate using a single anti-TNF antibody Infliximab the maximum concentration which can be measured with accuracy using our anti-TNF quantification approach.

A) Protocol

To perform this experiment, therapeutic antibody Infliximab was obtained from collaborators. The SIL Infliximab was produced and purified according to the method previously described (Lebert et al., Bioanalysis, 2015). Samples were treated using materials and methods described in Section A. Samples were treated following the option 1 described in the Section A. The peptides of sequences of SEQ ID NO. 1 to 8 were monitored in the LC-SRM assay, in their labelled and non-labelled forms.

TABLE 2

Samples constituted and analyzed to evaluate saturation of the TNF alpha antigen using a MSIA technology approach.

| Point | 1 | 2 | 3 | 4 |
|---|---|---|---|---|
| Human serum | 10 µl | 10 µl | 10 µl | 10 µl |
| Therapeutic Infliximab | 20 µg/ml | 50 µg/ml | 100 µg/ml | 200 µg/ml |
| SIL Infliximab | 40 µg/ml | 40 µg/ml | 40 µg/ml | 40 µg/ml |
| Final volume of the sample | 50 µl | 50 µl | 50 µl | 50 µl |

B) Experimental Results

The experiment performed here aimed at evaluating the maximum concentration of anti-TNF which can be measured with accuracy using the anti-TNF antibody quantification method described herein. To limit the complexity, it was evaluated using a single anti-TNF antibody, Infliximab, which was spiked in human serum at different concentration covering a range between 20 µg/ml and 200 µg/ml, while the SIL Infliximab standard was spiked in the same sample at a relatively high concentration of 40 µg/ml. The results are depicted in FIG. 2. The results obtained show that the quantification of Infliximab in these conditions is accurate and remains linear when therapeutic Infliximab is present in the sample at a concentration of 100 µg/ml and when SIL Infliximab standard is spiked at a concentration of 40 µg/ml. With the linear curve obtained, we can even extrapolate that it would be linear and accurate when therapeutic Infliximab is present in the sample at a concentration of 150 µg/ml and when SIL Infliximab standard is spiked at a concentration of 40 µg/ml. However, a saturation phenomenon appears when therapeutic Infliximab is present in the sample at a concentration of 200 µg/ml and when SIL Infliximab standard is spiked at a concentration of 40 µg/ml. These results allows concluding that the MSIA protocol described for performing the anti-TNF antibody quantification method described herein with an MSIA technique allows measuring with accuracy an anti-TNF therapeutic antibody present in a human blood sample at a concentration equal or below 40 µg/ml using until 5 SIL anti-TNF antibodies, each one spiked at a concentration of 20 µg/ml (total=100 µg/ml) and even until 30 µg/ml (total=150 µg/ml). The results also show that the MSIA protocol, when used for performing the anti-TNF antibody quantification method described herein allows measuring with accuracy an anti-TNF therapeutic antibody present in a human blood sample at a concentration equal or below 150 µg/ml using until 2 SIL anti-TNF antibodies, each one spiked at a concentration of 20 µg/ml (total concentration of anti-TNF antibodies=40 µg/ml).

These results show that the mass spectrometry immunoaffinity protocol, which is an illustration of embodiments of anti-TNF antibody quantification method described herein, may be used for the quantification of an anti-TNF antibody by using multiple SIL anti-TNF antibody standards.

Example 3: Assessment of a Titration Curve for the Quantification in Human Serum Samples of the Therapeutic Antibody Trastuzumab in the Presence of Two Other Anti-Cancer Antibodies (Rituximab and Bevacizumab), Using a Sample Preparation Based on Depletion in Non-Antibody Proteins Cibacron®

The objective of this experiment was to perform a titration curve in order to assess the performances of the stable-isotopically labelled (SIL) antibody standards and of the LC-MS/MS method.

In Example 3, a titration curve was performed by using (i) the non-labeled anti-cancer antibodies Trastuzumab, Rituximab and Bevacizumab as Internal Standard Compounds and (ii) SIL Trastuzumab as the anti-cancer antibody to be quantified. Indeed, the same experiment may be performed by using (i) SIL anti-cancer antibodies as Internal Standard compounds and (ii) a non-labeled Trastuzumab as the anti-cancer antibody to be quantified.

A) Protocol

A titration curve was generated, according to the following protocol 1) adding to a serum sample defined amount of therapeutic antibodies, Trastuzumab, Rituximab and Bevacizumab and 2) adding an increasing amount of SIL Trastuzumab. Thus, it is called a reverse titration curve because the SIL Trastuzumab is quantified using the therapeutic Trastuzumab.

Such an experiment mimics a situation where a patient would have been treated with Trastuzumab and whose serum will be analyzed using our LC-MS/MS method and three therapeutic standards.

To perform this experiment, therapeutic antibodies Trastuzumab, Rituximab and Bevacizumab were obtained from collaborators. The SIL Trastuzumab was produced and purified according to the method previously described (Lebert et al., Bioanalysis, 2015). Samples were treated using materials and methods described in Section B. Samples were treated following the option 1 described in the Section B. The peptides of sequences of SEQ ID NO. 47 to 73 were monitored in the LC-SRM assay, in their labelled and non-labelled forms.

TABLE 3

Samples constituted and analyzed to evaluate the accuracy and precision of our LC-MS/MS method in a context where multiple therapeutic antibodies are present in the sample.

| Point de gamme | 0 | 1 | 2 | 3 | 4 | 5 |
|---|---|---|---|---|---|---|
| Human serum treated | 20 µl | 20 µl | 20 µl | 20 µl | 20 µl | 20 µl |
| SIL Trastuzumab | 0 | 0.5 µg/ml | 5 µg/ml | 10 µg/ml | 25 µg/ml | 50 µg/ml |
| Therapeutic Trastuzumab | 20 µg/ml | 20 µg/ml | 20 µg/ml | 20 µg/ml | 20 µg/ml | 20 µg/ml |
| Therapeutic Rituximab | 20 µg/ml | 20 µg/ml | 20 µg/ml | 20 µg/ml | 20 µg/ml | 20 µg/ml |
| Therapeutic Bevacizumab | 20 µg/ml | 20 µg/ml | 20 µg/ml | 20 µg/ml | 20 µg/ml | 20 µg/ml |
| Tris 20 mM, 20 mM NaCl | 247 µl | 246 µl | 246 µl | 245 µl | 242 µl | 237 µl |
| Final volume of the sample | 250 µl | 250 µl | 250 µl | 250 µl | 250 µl | 250 µl |

B) Experimental Results

The quantification performances provided by our approach combining the use of mAb SIL standards and LC-MS/MS were assessed in a multiplex manner, where three different anti-cancer antibodies were simultaneously present in the human serum samples. For these tests, we have produced a reverse titration curve covering a concentration range between 0.5 µg/ml and 50 µg/ml.

The results are depicted in FIG. 3. The mean regression equation was Y=1.243×X+2.05 with a correlation coefficient $R^2$ of 0.996. For each concentration points, data obtained from the peptides monitored were consistent, indicating that our approach is robust. For each concentration points, data obtained from the peptides monitored were consistent, indicating that our approach is robust. The high accuracy of the method demonstrates that it is possible to quantify with a high degree of precision a therapeutic anti-cancer antibody present in the blood of a patient using a generic and blinded approach, by combining the use of a SIL antibody standard and LC-MS.

Thus, the method can be applied for the personalized therapeutic follow-up of patients treated with anti-cancer therapeutic antibodies.

More interestingly, the experimental results show that the anti-cancer antibody quantification method described herein does not requires a selection of an antibody-specific quantification method as it is the case in the present usual practice. Moreover, the anti-cancer antibody quantification method allows correcting situations wherein a patient's treatment is erroneously documented, and also allows determining anti-cancer antibodies concentrations in test samples from patients which have undergone anti-cancer combination therapy treatments. Finally, the anti-cancer antibody quantification method is not affected if the patient has received a first treatment with anti-cancer antibody and subsequently a second treatment with a second anti-cancer antibody distinct from the first antibody.

TABLE 3

Sequences

| SEQ ID NO. | Type | Description |
|---|---|---|
| 1 | Amino acid | Infliximab tryptic peptide |
| 2 | Amino acid | Infliximab tryptic peptide |
| 3 | Amino acid | Infliximab tryptic peptide |
| 4 | Amino acid | Infliximab tryptic peptide |
| 5 | Amino acid | Infliximab tryptic peptide |
| 6 | Amino acid | Infliximab tryptic peptide |
| 7 | Amino acid | Infliximab tryptic peptide |
| 8 | Amino acid | Infliximab tryptic peptide |
| 9 | Amino acid | Etanercept tryptic peptide |
| 10 | Amino acid | Etanercept tryptic peptide |
| 11 | Amino acid | Etanercept tryptic peptide |
| 12 | Amino acid | Etanercept tryptic peptide |
| 13 | Amino acid | Etanercept tryptic peptide |
| 14 | Amino acid | Etanercept tryptic peptide |
| 15 | Amino acid | Etanercept tryptic peptide |
| 16 | Amino acid | Adalimumab tryptic peptide |
| 18 | Amino acid | Adalimumab tryptic peptide |
| 19 | Amino acid | Adalimumab tryptic peptide |
| 20 | Amino acid | Adalimumab tryptic peptide |
| 21 | Amino acid | Adalimumab tryptic peptide |
| 22 | Amino acid | Adalimumab tryptic peptide |
| 23 | Amino acid | Adalimumab tryptic peptide |
| 24 | Amino acid | Certolizumab tryptic peptide |
| 25 | Amino acid | Certolizumab tryptic peptide |
| 26 | Amino acid | Certolizumab tryptic peptide |
| 27 | Amino acid | Certolizumab tryptic peptide |
| 28 | Amino acid | Certolizumab tryptic peptide |
| 29 | Amino acid | Certolizumab tryptic peptide |
| 30 | Amino acid | Certolizumab tryptic peptide |
| 31 | Amino acid | Golimumab tryptic peptide |
| 32 | Amino acid | Golimumab tryptic peptide |
| 33 | Amino acid | Golimumab tryptic peptide |
| 34 | Amino acid | Golimumab tryptic peptide |
| 35 | Amino acid | Golimumab tryptic peptide |
| 36 | Amino acid | Golimumab tryptic peptide |

TABLE 3-continued

Sequences

| SEQ ID NO. | Type | Description |
|---|---|---|
| 37 | Amino acid | Golimumab tryptic peptide |
| 38 | Amino acid | Infliximab IdeS proteolytic peptide (VH + CH1) |
| 39 | Amino acid | Infliximab IdeS proteolytic peptide (VL + CL) |
| 40 | Amino acid | Etanercept IdeS proteolytic peptide |
| 41 | Amino acid | Adalimumab IdeS proteolytic peptide (VH + CH1) |
| 42 | Amino acid | Adalimumab IdeS proteolytic peptide(VL + CL) |
| 43 | Amino acid | Certolizumab IdeS proteolytic peptide (VH + CH1) |
| 44 | Amino acid | Certolizumab IdeS proteolytic peptide (VL + CL) |
| 45 | Amino acid | Golimumab IdeS proteolytic peptide (VH + CH1) |
| 46 | Amino acid | Golimumab IdeS proteolytic peptide (VL + CL) |
| 47 | Amino acid | Trastuzumab tryptic peptide |
| 48 | Amino acid | Trastuzumab tryptic peptide |
| 49 | Amino acid | Trastuzumab tryptic peptide |
| 50 | Amino acid | Trastuzumab tryptic peptide |
| 51 | Amino acid | Trastuzumab tryptic peptide |
| 52 | Amino acid | Trastuzumab tryptic peptide |
| 53 | Amino acid | Trastuzumab tryptic peptide |
| 54 | Amino acid | Rituximab tryptic peptide |
| 55 | Amino acid | Rituximab tryptic peptide |
| 56 | Amino acid | Rituximab tryptic peptide |
| 57 | Amino acid | Rituximab tryptic peptide |
| 58 | Amino acid | Rituximab tryptic peptide |
| 59 | Amino acid | Rituximab tryptic peptide |
| 60 | Amino acid | Rituximab tryptic peptide |
| 61 | Amino acid | Rituximab tryptic peptide |
| 62 | Amino acid | Rituximab tryptic peptide |
| 63 | Amino acid | Rituximab tryptic peptide |
| 64 | Amino acid | Rituximab tryptic peptide |
| 65 | Amino acid | Bevacizumab tryptic peptide |
| 66 | Amino acid | Bevacizumab tryptic peptide |
| 67 | Amino acid | Bevacizumab tryptic peptide |
| 68 | Amino acid | Bevacizumab tryptic peptide |
| 69 | Amino acid | Bevacizumab tryptic peptide |
| 70 | Amino acid | Bevacizumab tryptic peptide |
| 71 | Amino acid | Bevacizumab tryptic peptide |
| 72 | Amino acid | Bevacizumab tryptic peptide |
| 73 | Amino acid | Infliximab, heavy chain |
| 74 | Amino acid | Infliximab, light chain |
| 75 | Amino acid | Adalimumab, heavy chain |
| 76 | Amino acid | Adalimumab, light chain |
| 77 | Amino acid | Etanercept |
| 78 | Amino acid | Certolizumab, heavy chain |
| 79 | Amino acid | Certolizumab, light chain |
| 80 | Amino acid | Golimumab, heavy chain |
| 81 | Amino acid | Golimumab, light chain |
| 82 | Amino acid | Trastuzumab, heavy chain |
| 83 | Amino acid | Trastuzumab, light chain |
| 84 | Amino acid | Rituximab, heavy chain |
| 85 | Amino acid | Rituximab, light chain |
| 86 | Amino acid | Bevacizumab, heavy chain |
| 87 | Amino acid | Bevacizumab, light chain |

The invention claimed is:

1. A method for quantifying a therapeutic antibody in a sample of a human individual comprising:
   a) adding to a test sample which may contain therapeutic antibodies to be quantified a known amount of two or more labeled forms of said therapeutic antibodies, wherein the two or more labeled forms of said therapeutic antibodies are whole antibodies, whereby a pre-proteolysis sample is provided,
   b) subjecting the pre-proteolysis sample to an enzyme proteolysis, so as to provide a proteolysis sample comprising (i) proteolysis labeled peptides derived from the labeled whole therapeutic antibodies and (ii) proteolysis peptides derived from the therapeutic antibody contained in the test sample,
   c) determining by mass spectrometric analysis the ratio between (i) one or more selected proteolysis labeled peptides and (ii) one or more corresponding proteolysis peptides derived from the said therapeutic antibody,
   d) calculating from the ratio determined at c) the amount of the said therapeutic antibody in the test sample.

2. The method according to claim 1, further comprising quantifying at least another therapeutic antibody in said sample of the human individual.

3. The method according to claim 1, wherein the two or more labeled forms of said therapeutic antibodies are selected in a group comprising Infliximab, Etanercept, Adalimumab, Certolizumab and Golimumab.

4. The method according to claim 1, wherein the two or more labeled forms of said therapeutic antibodies are selected in a group comprising Trastuzumab, Rituximab and Bevacizumab.

5. The method according claim 1, wherein the enzyme proteolysis in b) comprises:
   b1) enzyme proteolysis in denaturing conditions, and
   b2) enzyme proteolysis in non-denaturing conditions.

6. The method according to claim 1, wherein enzyme proteolysis is performed at b) by using trypsin.

7. The method according to claim 1, wherein the one or more selected proteolysis labeled peptides are selected in a group comprising:
   for Infliximab: peptides of SEQ ID NO. 1-8,
   for Etanercept: peptides of SEQ ID NO. 9-15,
   for Adalimumab: peptides of SEQ ID NO. 16-23,
   for Certolizumab: peptides of SEQ ID NO. 24-30, and
   for Golimumab: peptides of SEQ ID NO. 31-37,
   for Trastuzumab: peptides of SEQ ID NO. 47-53,
   for Rituximab: peptides of SEQ ID NO. 54-64,
   for Bevacizumab: peptides of SEQ ID NO. 65-72.

8. The method according to claim 1, wherein proteolysis is performed at b) by incubating the pre-proteolysis sample with a hinge-targeting protease.

9. The method according to claim 8, wherein the hinge-targeting protease is selected in a group comprising Gelatinase A (MMP-2), Stromyelysin (MMP-3), Matrilysin (MMP-7), Gelatinase B (MMP-9), Macrophage metalloelastase (MMP-12), Collagenase-3 (MMP-13), Cathepsin G, Pseudolysin, Mirabilysin, Glutamyl endopeptidase I (GluV8), Streptopain (SpeB), Trepolisin and Immunoglobulin-degrading enzyme from *Streptococcus* (ideS).

10. The method according to claim 8, wherein the hinge-targeting protease is an Immunoglobulin-degrading enzyme from *Streptococcus* (ideS).

11. The method according to claim 8, wherein the one or more selected proteolysis labeled peptides are selected in a group comprising:
   for Infliximab: peptides of SEQ ID NO. 38-39,
   for Etanercept: peptide of SEQ ID NO. 40,
   for Adalimumab: peptides of SEQ ID NO. 41-42,
   for Certolizumab: peptides of SEQ ID NO. 43-44, and
   for Golimumab: peptides of SEQ ID NO. 45-46.

12. The method according to claim 1, wherein a) comprises:
   a1) the adding to the test sample, of the known amount of the two or more labeled forms of said therapeutic antibodies, wherein the two or more labeled forms of said therapeutic antibodies include two or more labeled anti-TNF antibodies selected in a group comprising Infliximab, Etanercept, Adalimumab, Certolizumab and Golimumab, whereby a non-concentrated pre-proteolysis sample is provided, and
   a2) enriching the non-concentrated pre-proteolysis sample in the therapeutic antibodies, whereby the pre-proteolysis sample is provided.

13. The method according to claim 12, wherein at a2), the non-concentrated proteolysis sample is subjected to protein depletion.

14. The method according to claim 12, wherein at a2), the non-concentrated proteolysis sample is subjected to immunocapture.

15. The method according to claim 1, wherein the test sample is a human sample from an individual who has been administered with an anti-TNF antibody selected in a group comprising Infliximab, Etanercept, Adalimumab, Certolizumab and Golimumab.

16. The method according to claim 12, wherein at a2), the non-concentrated proteolysis sample is subjected to albumin depletion.

17. The method according to claim 12, wherein at a2), the non-concentrated proteolysis sample is subjected to immunocapture using an affinity substrate onto which a therapeutic antibody target is immobilized.

* * * * *